US006444790B1

(12) United States Patent
Young et al.

(10) Patent No.: US 6,444,790 B1
(45) Date of Patent: Sep. 3, 2002

(54) PEPTIDOGLYCAN RECOGNITION PROTEINS

(75) Inventors: Paul E. Young, Gaithersburg; Steven M. Ruben, Olney; Craig A. Rosen, Laytonsville; Henrik S. Olsen, Gaithersburg, all of MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/469,242

(22) Filed: Dec. 22, 1999

Related U.S. Application Data

(60) Provisional application No. 60/113,809, filed on Dec. 23, 1998, now abandoned.

(51) Int. Cl.[7] .......................... C07K 1/00; A61K 38/00; C12P 21/06
(52) U.S. Cl. ................. 530/350; 530/300; 435/69.1
(58) Field of Search .................. 530/300, 350; 435/69.1

(56) References Cited

U.S. PATENT DOCUMENTS 6,034,217 A    3/2000   Ashida et al.

FOREIGN PATENT DOCUMENTS

| WO | WO97/29765 | 8/1997 |
| WO | 98/51790 | 11/1998 |
| WO | WO99/02686 | 1/1999 |
| WO | WO99/58660 | 11/1999 |
| WO | WO00/39327 | 7/2000 |

OTHER PUBLICATIONS

Bowie et al (Science, 1990, 257:1306–1310).*
Burgess et al (J of Cell Bio. 111:2129–2138, 1990).*
Scott et al (Nature Genetics, 1999, 21:440–443).*
Bork (Genome Research, 2000, 10:398–400).*
Reiger et al (Glossary of Genetics and Cytogenetics, Classical and Molecular, 4th Ed., Springer–Verlay, Berlin, 1976).*
Herbert et al. (The Dictionary of Immunology, Academic Press, 4th edition, 1995).*
Greenspan et al., (Nature Biotechnology 7:936–937 (1999).*
Lazar et al. Molecular and Cellular Biology 8:1247–1252, 1988.*
Labeit et al. (GENBANK™ Sequence Database (Accession Q15346), National Center for Biotechnology Information, National Library of Medicine, Bethesda, Maryland, publicly available Nov., 1996).*
TrEMBL Accession No. 075594 (Nov. 1, 1998).
Geneseq Database Accession No. Y00771 (Jan. 21, 1999).
GenBank Accession No. AI056693 (Jul. 20, 1998).
Geneseq Database Accession No. Y96963 (Jul. 6, 2000).
Geneseq Database Accession No. Y76124 (Nov. 18, 1999).
Geneseq Database Accession No. Y96962 (Jul. 6, 2000).
Geneseq Database Accession No. A51718 (Jul. 6, 2000).
Geneseq Database Accession No. A51717 (Jul. 6, 2000).
Geneseq Database Accession No. Z65250 (Nov 18, 1999).
NCBI Accession No. AAF99599 (Aug. 15, 2000).
NCBI Accession No. AF086392 (Aug. 29, 1998).
NCBI Accession No. AAC31822 (Dec. 14, 1998).
Kang et al, "A peptiodglycan recognition protein in innate immunity conserved from insects to humans," Proc. Natl. Acad. Sci. USA, 95:1078–1082 (Aug. 1998).

* cited by examiner

Primary Examiner—Anthony C. Caputa
Assistant Examiner—Gary B. Nickol
(74) Attorney, Agent, or Firm—Human Genome Sciences, Inc.

(57) ABSTRACT

The present invention relates to three novel peptidoglycan recognition binding proteins expressed by keratinocytes, wound-healing tissues and chondrosarcoma tissue. More specifically, isolated nucleic acid molecules are provided encoding human peptidoglycan recognition protein-related proteins, referred to herein as PGRP-K (Keratinocytes), PGRP-W (Wound-healing), and PGRP-C (Chondrosarcoma) of FIGS. 1A–B, FIGS. 2A–C, and FIG. 3, respectively, each having homology to both human peptidoglycan recognition protein (PGRP) as well as murine Tag-7. PGRP-K, PGRP-W, and PGRP-C polypeptides are also provided. Further provided are vectors, host cells and recombinant methods for producing the same. The invention also relates to both the inhibition and enhancement of activities of PGRP-K, PGRP-W, and PGRP-c polypeptides and diagnostic methods for detecting PGRP-K, PGRP-W, and PGRP-C gene expression.

79 Claims, 11 Drawing Sheets

Figure 1A

```
  1 CTGGGCTGGAACAGCACAGAACCCACAGGGCTGCCGTCCACACTCTCCCGGTCAGAGTCC    60

61 TGGGACCACATGGGGACGCTGCCATGGCTTCTTGCCTTCTTCATTCTGGGTCTCCAGGCT   120
  1             M   G   T   L   P   W   L   L   A   F   F   I   L   G   L   Q   A    17

121 TGGGATACTCCCACCATCGTCTCCCGCAAGGAGTGGGGGGCAAGACCGCTCGCCTGCAGG   180
 18  W   D   T   P   T   I   V   S   R   K   E   W   G   A   R   P   L   A   C   R    37

181 GCCCTGCTGACCCTGCCTGTGGCCTACATCATCACAGACCAGCTCCCAGGGATGCAGTGC   240
 38  A   L   L   T   L   P   V   A   Y   I   I   T   D   Q   L   P   G   M   Q   C    57

241 CAGCAGCAGAGCGTTTGCAGCCAGATGCTGCGGGGGTTGCAGTCCCATTCCGTCTACACC   300
 58  Q   Q   Q   S   V   C   S   Q   M   L   R   G   L   Q   S   H   S   V   Y   T    77

301 ATAGGCTGGTGCGACGTGGCGTACAACTTCCTGGTTGGGGATGATGGCAGGGTGTATGAA   360
 78  I   G   W   C   D   V   A   Y   N   F   L   V   G   D   D   G   R   V   Y   E    97

361 GGTGTTGGCTGGAACATCCAAGGCTTGCACACCCAGGGCTACAACAACATTTCCCTGGGC   420
 98  G   V   G   W   N   I   Q   G   L   H   T   Q   G   Y   N   N   I   S   L   G   117

421 ATCGCCTTCTTTGGCAATAAGATAAGCAGCAGTCCCAGCCCTGCTGCCTTATCAGCTGCA   480
118  I   A   F   F   G   N   K   I   S   S   S   P   S   P   A   A   L   S   A   A   137

481 GAGGGTCTGATCTCCTATGCCATCCAGAAGGGTCACCTGTCGCCCAGGTATATTCAGCCA   540
138  E   G   L   I   S   Y   A   I   Q   K   G   H   L   S   P   R   Y   I   Q   P   157

541 CTTCTTCTGAAAGAAGAGACCTGCCTGGACCCTCAACATCCAGTGATGCCCAGGAAGGTT   600
158  L   L   L   K   E   E   T   C   L   D   P   Q   H   P   V   M   P   R   K   V   177

601 TGCCCCAACATCATCAAACGATCTGCTTGGGAAGCCAGAGAGACACACTGCCCTAAAATG   660
178  C   P   N   I   I   K   R   S   A   W   E   A   R   E   T   H   C   P   K   M   197

661 AACCTCCCAGCCAAATATGTCATCATCATCCACACCGCTGGCACAAGCTGCACTGTATCC   720
198  N   L   P   A   K   Y   V   I   I   I   H   T   A   G   T   S   C   T   V   S   217

721 ACAGACTGCCAGACTGTCGTCCGAAACATACAGTCCTTTCACATGGACACACGGAACTTT   780
218  T   D   C   Q   T   V   V   R   N   I   Q   S   F   H   M   D   T   R   N   F   237

781 TGTGACATTGGATATCAATAAGGCCAGGCGTGGCGGCGATTACGTCTGTAATCCCAGGAC   840
238  C   D   I   G   Y   Q                                                           243

841 TTTGGGAGGCCAAGGCGGGCAGATCACTTCAGGCCAGGAATTCAAGAGCAGCCTGGCCAA   900
```

Figure 1B

```
 901  TATGGCGAAACTCTGTCTCTACTGAAAACAAACAAACAAACAAACAAACAAAGAAA   960

961  CAACAAAAATTAGCCGGGTGTGGTGGCACACGCCTGTAGTCCCAGCTACTCAGGAGGCTG  1020

1021  AGGCATAAGAATTGCTTGAACCCTGGAGGCGGAGGTTGCAGTGAGCTGAGATTGGGCCAC  1080

1081  CGCACTCCAGTCTGGGAGACAGAGTGAGACTGTCTCAAAACAACAACAAAAAAATCCCTA  1140

1141  ACATAATCTCAAAAAAAAAAAAAAAAAAAAAAAAAAAAAAAA  1182
```

Figure 2A

```
  1 GGGCAAGCTGACTGCACCCTGACCTGCTGGGCTGGGACAGCACAGGACCCACAGATATCT   60

61 GCTGCCATCCACACTCTCCAGATTGGTGTCCTGGGACCACGTGGGGATGCTGCTGTGGCT  120
  1                                                 M  L  L  W  L    5

121 TCTTGTCTTCTCTGCTCTGGGTATCCAGGCCTGGGGTGATTCCTCCTGGAACAAAACACA  180
  6  L  V  F  S  A  L  G  I  Q  A  W  G  D  S  S  W  N  K  T  Q    25

181 AGCTAAACAGGTATCAGAGGGGCTCCAGTACCTATTTGAGAACATCTCCCAGCTCACTGA  240
 26  A  K  Q  V  S  E  G  L  Q  Y  L  F  E  N  I  S  Q  L  T  E    45

241 AAAAGATGTCTCCACCACGGTCTCTCGCAAGGCATGGGGGGCAGAAGCTGTTGGCTGCAG  300
 46  K  D  V  S  T  T  V  S  R  K  A  W  G  A  E  A  V  G  C  S    65

301 TATTCAGCTGACCACGCCAGTGAATGTCCTTGTTATACACCATGTCCCTGGACTGGAGTG  360
 66  I  Q  L  T  T  P  V  N  V  L  V  I  H  H  V  P  G  L  E  C    85

361 TCACGACCAGACAGTCTGCAGCCAGAGACTGCGGGAACTGCAGGCCCATCATGTCCACAA  420
 86  H  D  Q  T  V  C  S  Q  R  L  R  E  L  Q  A  H  H  V  H  N   105

421 CAACAGTGGGTGTGATGTGGCCTACAACTTCCTGGTTGGGGATGATGGCAGGGTGTATGA  480
106  N  S  G  C  D  V  A  Y  N  F  L  V  G  D  D  G  R  V  Y  E   125

481 AGGTGTTGGCTGGAATATCCAAGGAGTGCACACCCAAGGCTACAACAACATCTCCCTGGG  540
126  G  V  G  W  N  I  Q  G  V  H  T  Q  G  Y  N  N  I  S  L  G   145

541 CTTTGCCTTCTTCGGCACTAAGAAAGGCCACAGTCCCAGCCCTGCTGCCCTGTCGGCCAT  600
146  F  A  F  F  G  T  K  K  G  H  S  P  S  P  A  A  L  S  A  M   165

601 GGAAAACCTAATCACCTATGCTGTCCAGAAGGGCCACCTGTCATCCAGTTATGTTCAGCC  660
166  E  N  L  I  T  Y  A  V  Q  K  G  H  L  S  S  S  Y  V  Q  P   185

661 ACTTCTTGGGAAAGGCGAGAACTGCCTGGCCCCTCGGCAGAAGACAAGCCTGAAGAAGCT  720
186  L  L  G  K  G  E  N  C  L  A  P  R  Q  K  T  S  L  K  K  L   205

721 TGCCCCGGCATTGTCCCACGGTCTGTGTGGGGAGCCAGGGAGACCACTGTCCAGGATGAC  780
206  A  P  A  L  S  H  G  L  C  G  E  P  G  R  P  L  S  R  M  T   225

781 TCTCCCAGCGAAGTATGGCATCATTATCCACACTGCCGGGAGGACCTGCAACATTTCTGA  840
226  L  P  A  K  Y  G  I  I  I  H  T  A  G  R  T  C  N  I  S  D   245
```

Figure 2B

```
 841  TGAGTGCCGCCTGCTGGTCCGGGACATCCAGTCTTTCTACATAGACAGGCTCAAGTCATG   900
 246   E  C  R  L  L  V  R  D  I  Q  S  F  Y  I  D  R  L  K  S  C    265

901  CGACATTGGTTATAACTTCCTGGTGGGCCAGGATGGCGCCATTTATGAAGGGGTGGGCTG   960
 266   D  I  G  Y  N  F  L  V  G  Q  D  G  A  I  Y  E  G  V  G  W    285

961  GAATGTCCAAGGCTCCTCCACCCCTGGCTACGATGACATTGCCCTGGGCATTACCTTCAT  1020
 286   N  V  Q  G  S  S  T  P  G  Y  D  D  I  A  L  G  I  T  F  M    305

1021  GGGCACCTTCACAGGTATACCACCCAATGCTGCAGCACTAGAGGCAGCCCAAGACCTGAT  1080
 306   G  T  F  T  G  I  P  P  N  A  A  A  L  E  A  A  Q  D  L  I    325

1081  CCAGTGTGCCATGGTCAAAGGGTACCTGACTCCCAACTACCTGCTGGTGGGCCACAGTGA  1140
 326   Q  C  A  M  V  K  G  Y  L  T  P  N  Y  L  L  V  G  H  S  D    345

1141  TGTGGCCCGAACCTTGTCTCCTGGGCAGGCTTTGTACAACATCATCAGCACCTGGCCTCA  1200
 346   V  A  R  T  L  S  P  G  Q  A  L  Y  N  I  I  S  T  W  P  H    365

1201  TTTCAAACACTGAGAGAAGCCCCAGGTCCTTCTGAGACTGCTTTCCCTCCCCTGTCAGGT  1260
 366   F  K  H                                                        368

1261  CTCTCCTGTCCTAACCATCCAGCTTGGCTCAACACCTTTTGCCCTCCTCCCTGCCACAC   1320

1321  AGTCCTGTGCCTCCTTTTTCAGGTTGGGATGATCATGCCTCTCCTGCCAACATCCTCCAA  1380

1381  GGGCCTCCAAACTCATAGCTGGACATTCACAGCCCTCTGAGTCTGAGTCCAGATTTCTTC  1440

1441  TCTCCTTACTTCCTCTCCCTTGGAAACCCAACTCCTCAGCCAGGTGAGACAATGGGCTGG  1500

1501  TTCTTGTTTCATTTCTCTCTCTCTCTCCATTCCCCTCTGCCTGGTGAGCCTTCCCCTGGT  1560

1561  GTCTGCCTGGCAGCCCCCACCACCCACCTATCACCCCTCACCCATAACTCAGGTCAACGT  1620

1621  GACCAACCTTCCTTGCTTACACATAAACTTGTATATATTTGGATGTAGCCCTTATTTAAT  1680

1681  GGCTGTCATTATTTATAGATATGTCTATCCTTGCTACTTGGTTGTGAGTTTCTCCAGGGG  1740

1741  AGGAACTGTGTTTTATTCATCTCTATGTCCTCTGTTTCTCAGCAGTGTCTGAAATTTAAT  1800

1801  GGGTTCTACTGATGTTTATTAGAGAAATGGATGAATAAATGAATGAAGAGATCCAAAAAA  1860
```

Figure 2C

1861 AAAAAAAAAAAAAAAA 1876

Figure 3

```
  1 GATCCCCCGGGCTGCAGGAATTCGGCACGAGCCGGACCCTGCCGCCCTGCCACTATGTCC   60
  1                                                           M  S   2

61 CGCCGCTCTATGCTGCTTGCCTGGGCTCTCCCCAGCCTCCTTCGACTCGGAGCGGCTCAG  120
  3  R  R  S  M  L  L  A  W  A  L  P  S  L  L  R  L  G  A  A  Q   22

121 GAGACAGAAGACCCGGCCTGCTGCAGCCCCATAGTGCCCCGGAACGAGTGGAAGGCCCTG  180
 23  E  T  E  D  P  A  C  C  S  P  I  V  P  R  N  E  W  K  A  L   42

181 GCATCAGAGTGCGCCCAGCACCTGAGCCTGCCCTTACGCTATGTGGTGGTATCGCACACG  240
 43  A  S  E  C  A  Q  H  L  S  L  P  L  R  Y  V  V  V  S  H  T   62

241 GCGGGCAGCAGCTGCAACACCCCCGCCTCGTGCCAGCAGCAGGCCCGGAATGTGCAGCAC  300
 63  A  G  S  S  C  N  T  P  A  S  C  Q  Q  Q  A  R  N  V  Q  H   82

301 TACCACATGAAGACACTGGGCTGGTGCGACGTGGGCTACAACTTCCTGATTGGAGAAGAC  360
 83  Y  H  M  K  T  L  G  W  C  D  V  G  Y  N  F  L  I  G  E  D  102

361 GGGCTCGTATACGAGGGCCGTGGCTGGAACTTCACGGGTGCCCACTCAGGTCACTTATGG  420
103  G  L  V  Y  E  G  R  G  W  N  F  T  G  A  H  S  G  H  L  W  122

421 AACCCCATGTCCATTGGCATCAGCTTCATGGGCAACTACATGGATCGGGTGCCCACACCC  480
123  N  P  M  S  I  G  I  S  F  M  G  N  Y  M  D  R  V  P  T  P  142

481 CAGGCCATCCGGGCAGCCCAGGGTCTACTGGCCTGCGGTGTGGCTCAGGGAGCCCTGAGG  540
143  Q  A  I  R  A  A  Q  G  L  L  A  C  G  V  A  Q  G  A  L  R  162

541 TCCAACTATGTGCTCAAAGGACACCGGGATGTGCAGCGTACACTCTCTCCAGGCAACCAG  600
163  S  N  Y  V  L  K  G  H  R  D  V  Q  R  T  L  S  P  G  N  Q  182

601 CTCTACCACCTCATCCAGAATTGGCCACACTACCGCTCCCCCTGAGGCCCTGCTGATCCG  660
183  L  Y  H  L  I  Q  N  W  P  H  Y  R  S  P                    196

661 CACCCCATTCCTCCCCTCCCATGGCCAAAAACCCCACTGTCTCCTTCTCCAATAAAGATG  720

721 TAGCTCAAAAAAAAAAAAAAAAAAAAAAAA  749
```

Figure 4A

```
                10                  20                  30                  40
  1  M G T L P W L L A F F - - - - - I L G L Q - - - - - - - - - A W - - - - - - - - - - -   PGRP-K (HKAEZ65)
  1  M - - L L W L L V F S - - - - - A L G I Q - - - - - - - - - A W G D S S W N K T Q       PGRP-W (HWHGB15)
  1  M - - S R R S M L L A W A L P S L I R L G A A Q E T E D P A - - - - - - - - - - - - -   PGRP-C (HCDDP40)
  1  M - - L F A C A L L A - - - - - L L G L A - - - - - - - - - T - - - - - - - - - - - -   Mouse Tag-7

50                  60                  70                  80
 19  - - - - - - - - - - - - - - - - - - D T P T I V S R K E W G A R P L A C R                PGRP-K (HKAEZ65)
 26  A K Q V S E G L Q Y L F E N I S Q L T E K D V S T T V S H K A W G A E A V G C S          PGRP-W (HWHGB15)
 29  - - - - - - - - - - - - - - - - - C C S P I V P H N E W K A L A S E C A                  PGRP-C (HCDDP40)
 16  - - - - - - - - - - - - - - - - - S C S F I V P R S E W R A L P S E C S                  Mouse Tag-7

90                 100                 110                 120
 38  A L L T L P V A Y I I T D Q L P G M Q C Q Q Q S V C S Q M L R G L Q S H S V Y T          PGRP-K (HKAEZ65)
 66  I Q L T T P V N V L V I H H V P G L E C H D Q T V C S Q R L R E L Q A H H V H N          PGRP-W (HWHGB15)
 48  Q H I S L P L R Y V V V S H T A G S S C N T P A S C Q Q Q A R N V Q H Y H M K T          PGRP-C (HCDDP40)
 35  S R L G H P V R Y V V I S H T A G S F C N S P D S C E Q Q A R N V Q H Y H K N E          Mouse Tag-7

130                 140                 150                 160
 78  I G W C D V A Y N F L V G D D G R V Y E G V G W N I Q G L H T Q G Y N N I S L G          PGRP-K (HKAEZ65)
106  N S G C D V A Y N F L V G D D G R V Y E G V G W N I Q G V H T Q G Y N N I S L G          PGRP-W (HWHGB15)
 88  L G W C D V G Y N F L I G E D G L V Y E G R G W N F T G A H S - - - - - - - - -          PGRP-C (HCDDP40)
 75  L G W C D V A Y N F L I G E D G H V Y E G R G W N I K G D H T - - - - - - - - -          Mouse Tag-7

170                 180                 190                 200
118  I A F F G N K I S S S P S P A A L S A A E G L I S Y A I Q K G H L S P R Y I Q P          PGRP-K (HKAEZ65)
146  F A F F G T K K G H S P S P A A L S A M E N L I T Y A V Q K G H L S S S Y V Q P          PGRP-W (HWHGB15)
119  - - - - - - - - - - - - - - - - - - - - - - - - - - - - - - - - - - - - - - - -        PGRP-C (HCDDP40)
106  - - - - - - - - - - - - - - - - - - - - - - - - - - - - - - - - - - - - - - - -        Mouse Tag-7

210                 220                 230                 240
158  L L L K E E T C L D P Q H P V M P R K V C P N I I K - - - - R S A W E A R E T H          PGRP-K (HKAEZ65)
186  L L G K G E N C L A P R Q K T S L K K L A P A L S H G L C G E P G R P L - - - -          PGRP-W (HWHGB15)
119  - - - - - - - - - - - - - - - - - - - - - - - - - - - - - - G H L W N P - - - -          PGRP-C (HCDDP40)
106  - - - - - - - - - - - - - - - - - - - - - - - - - - - - - - G P I W N P - - - -          Mouse Tag-7

250                 260                 270                 280
194  C P K M N L P A K Y V I I H T A G T S C T V S T D C Q T V V R N I Q S F H M D            PGRP-K (HKAEZ65)
222  - S R M T L P A K Y G I I I H T A G R T C N I S D E C R L L V R D I Q S F Y I D          PGRP-W (HWHGB15)
125  - - - - - - - - - - - - - - - - - - - - - - - - - - - - - - - - - - - - - - - -        PGRP-C (HCDDP40)
112  - - - - - - - - - - - - - - - - - - - - - - - - - - - - - - - - - - - - - - - -        Mouse Tag-7

290                 300                 310                 320
234  T R N F C D I G Y - - - - - - - - - - - - - - - - - - - - - - - - - - - - - - -        PGRP-K (HKAEZ65)
261  R L K S C D I G Y N F L V G Q D G A I Y E G V G W N V Q G S S T P G Y D D I A L          PGRP-W (HWHGB15)
125  - - - - - - - - - - - - - - - - - - - - - - - - - - - - - - - - - - - M S I            PGRP-C (HCDDP40)
112  - - - - - - - - - - - - - - - - - - - - - - - - - - - - - - - - - - - M S I            Mouse Tag-7
```

Figure 4B

```
                330              340              350              360
243 - - - - - - - - - - - - - - - - - - - - - - - - - - - - - - - - -   PGRP-K (HKABZ65)
301 G I T F M G T F T G I P - - - - - - - - P N A A A L E A A Q D L I Q C A M V K G   PGRP-W (HWHGB15)
128 G I S F M G N Y M D R V - - - - - - - - P T P Q A I R A A Q G L L A C G V A Q G   PGRP-C (HCDDP40)
115 G I T F M G N F M D R V R K A G P P C C P K S S G I W G V S G L - - - - - - - -   Mouse Tag-7

370              380              390
243 - - - - - - - - - - - - - - - - - - - - - - - - - - - Q   PGRP-K (HKABZ65)
333 Y L T P N Y L L V G H S D V A R T L S P G Q A L Y N I I S T W P H F K H   PGRP-W (HWHGB15)
160 A L R S N Y V L K G H R D V Q R T L S P G N Q L Y H L I Q N W P H Y R S P   PGRP-C (HCDDP40)
147 - - - - - - - - - - - - - - - - - P E I Q L   Mouse Tag-7
```

'Decoration 'Decoration#1': Shade (with solid black) residues that match
the consensus named 'Consensus #1' exactly.

PEPTIDOGLYCAN RECOGNITION PROTEINS

FIELD OF THE INVENTION

This application claims benefit under 35 U.S.C. §119(e) of the filing date of U.S. Provisional Application Serial No. 60/113,809, filed on Dec. 23, 1998, now abandoned, which is hereby incorporated by reference.

The present invention relates to three novel peptidoglycan recognition binding proteins expressed by keratinocytes, wound-healing tissues and chondrosarcoma tissue. More specifically, isolated nucleic acid molecules are provided encoding human peptidoglycan recognition protein-related proteins, referred to herein as PGRP-K (Keratinocytes), PGRP-W (Wound-healing), and PGRP-C (Chondrosarcoma) of FIGS. 1A–B, FIGS. 2A–C, and FIG. 3, respectively, each having homology to both human peptidoglycan recognition protein (PGRP) as well as murine Tag-7. PGRP-K, PGRP-W, and PGRP-C polypeptides are also provided. Further provided are vectors, host cells and recombinant methods for producing the same. The invention also relates to both the inhibition and enhancement of activities of PGRP-K, PGRP-W, and PGRP-C polypeptides and diagnostic methods for detecting PGRP-K, PGRP-W, and PGRP-C gene expression.

BACKGROUND OF THE INVENTION

Peptidoglycan, as well as Lipopolysaccharide (LPS), is a surface component of many bacteria which illicit a wide range of physiological and immune responses in humans. Specifically, peptidoglycan has been shown to manifest itself clinically by reproducing most of the symptoms of bacterial infection, including fever, acute-phase response, inflammation, septic shock, leukocytosis, sleepiness, malaise, abcess formation, and arthritis (see Dziarski et al., JBC, 273 (15): 8680 (1998)). Furthermore, the type of peptidoglycan (i.e.—the specific stereoisomers or analogs of muramyl dipeptide, N-acetylglucosaminyl-beta(1–4)-N-acteylmuramyl tetrapeptides, etc.), were shown to elicit a broad range of activities, including exhibiting greater pyrogenicity, inducing acute joint inflammation, stimulating macrophages, and causing hemorrhagic necrosis at a primed site (See Kotani et al., Fed Proc, 45(11): 2534 (1986)).

It has been demonstrated in humans that a lipopolysaccharide binding protein exists that was discovered as a trace plasma protein (See Schumann et al., Science, 249(4975) :1429 (1990)). It is thought that one of the modes of action by which this lipopolysaccharide binding protein functions is by forming high-affinity complexes with lipopolysaccharide, that then bind to macrophages and monocytes, inducing the secretion of tumor necrosis factor. Dziarski and Gupta (See Dziarski et al., JBC, 269(3): 2100 (1994)) demonstrated that a 70 kDa receptor protein present on the surface of mouse lymphocytes served to bind heparin, heparinoids, bacterial lipoteichoic acids, peptidoglycan, and lipopolysaccharides.

Recently, Dziarski et al. demonstrated that the CD14, a glycosylphosphatidylinositol-linked protein present on the surface of macrophage and polymorphonuclear leukocytes, bound peptidoglycan and lipopolysaccharide. Furthermore, the binding affinity of CD14 for lipopolysaccharide was significantly increased in the presence of a LPS-binding protein present in plasma. It is thought that the LPS-binding protein functions as a transfer molecule, whereby it binds LPS and presents it to the CD14 receptor (See Dziarski et al., JBC, 273(15): 8680 (1998)).

Yoshida et al. isolated a peptidoglycan binding protein from the hemolymph of the Silkworm, *Bombyx mori*, using column chromatography. This protein was found to have a very specific affinity for peptidoglycan (See Yoshida et al., JBC, 271(23): 13854 (1996)). Additionally, Kang et al. recently cloned a peptidoglycan binding protein from the moth Trichoplusia ni. The peptidoglycan binding protein was shown to bind strongly to insoluble peptidoglycan (See Kang et al., PNAS, 95(17): 10078 (1998)). In this study the peptidoglycan binding protein was upregulated by a bacterial infection in T. ni. The insect immune system is regarded as a model for innate immunity. Thus, Kang et al were able to clone both mouse and human homologs of the T. ni peptidoglycan binding protein. All of these peptidoglycan binding proteins shared regions of homolgy, as well as four conserved cysteine residues which may function in the tertiary structure of the protein, possibly in helping to form binding domains. Given that peptidoglycan is an integral component of bacterial cell walls, and that it induces many physiological responses from cytokine secretion to inflammation and macrophage activation, it appears as if this family of proteins may be a ubiquitous group involved in the binding and recognition of peptidoglycan, the presentation of antigens (e.g., cell wall components, etc.), and the activation of the immune system, such as the secretion of cytokines, such as TNF.

TNF is noted for its pro-inflammatory actions which result in tissue injury, such as induction of procoagulant activity on vascular endothelial cells (Pober, J. S. et al., *J. Immunol.* 136:1680 (1986)), increased adherence of neutrophils and lymphocytes (Pober, J. S. et al., *J. Immunol.* 138:3319 (1987)), and stimulation of the release of platelet activating factor from macrophages, neutrophils and vascular endothelial cells (Camussi, G. et al., *J. Exp. Med.* 166:1390 (1987)).

Recent evidence implicates TNF in the pathogenesis of many infections (Cerami, A. et al., *Immunol. Today* 9:28 (1988)), immune disorders, neoplastic pathology, e.g., in cachexia accompanying some malignancies (Oliff, A. et al., *Cell* 50:555 (1987)), and in autoimmune pathologies and graft-versus host pathology (Piguet, P.-F. et al., *J. Exp. Med.* 166:1280 (1987)). The association of TNF with cancer and infectious pathologies is often related to the host's catabolic state. A major problem in cancer patients is weight loss, usually associated with anorexia. The extensive wasting which results is known as "cachexia" (Kern, K. A. et al. *J. Parent. Enter. Nutr.* 12:286–298 (1988)). Cachexia includes progressive weight loss, anorexia, and persistent erosion of body mass in response to a malignant growth. The cachectic state is thus associated with significant morbidity and is responsible for the majority of cancer mortality. A number of studies have suggested that TNF is an important mediator of the cachexia in cancer, infectious pathology, and in other catabolic states.

TNF is thought to play a central role in the pathophysiological consequences of Gram-negative sepsis and endotoxic shock (Michie, H. R. et al., *Br. J Surg.* 76:670–671 (1989); Debets, J. M. H. et al., *Second Vienna Shock Forum*, p.463–466 (1989); Simpson, S. Q. et al., *Crit. Care Clin.* 5:27–47 (1989)), including fever, malaise, anorexia, and cachexia. Endotoxin is a potent monocyte/macrophage activator which stimulates production and secretion of TNF (Kombluth, S. K. et al, *J. Immunol.* 137:2585–2591 (1986)) and other cytokines. Because TNF could mimic many biological effects of endotoxin, it was concluded to be a central mediator responsible for the clinical manifestations of endotoxin-related illness. TNF and other monocyte-derived cytokines mediate the metabolic and neurohormonal responses to endotoxin (Michie, H. R. et al., *N. Eng. J. Med.* 318:1481–1486 (1988)). Endotoxin administration to human volunteers produces acute illness with flu-like symptoms including fever, tachycardia, increased metabolic rate and stress hormone release (Revhaug, A. et al., *Arch. Surg.* 123:162–170 (1988)). Elevated levels of circulating TNF have also been found in patients suffering from Gram-negative sepsis (Waage, A. et al., *Lancet* 1:355–357 (1987); Hammerle, A. F. et al., *Second Vienna Shock Forum* p. 715–718 (1989); Debets, J. M. H. et al., *Crit. Care Med.* 17:489–497 (1989); Calandra, T. et al., *J. Infec. Dis.* 161:982–987 (1990)).

Passive immunotherapy directed at neutralizing TNF may have a beneficial effect in Gram-negative sepsis and endotoxemia, based on the increased TNF production and elevated TNF levels in these pathology states, as discussed above. Antibodies to a "modulator" material which was characterized as cachectin (later found to be identical to TNF) were disclosed by Cerami et al. (EPO Patent Publication 0,212,489, Mar. 4, 1987). Such antibodies were said to be useful in diagnostic immunoassays and in therapy of shock in bacterial infections. Rubin et al. (EPO Patent Publication 0,218,868, Apr. 22, 1987) disclosed monoclonal antibodies to human TNF, the hybridomas secreting such antibodies, methods of producing such antibodies, and the use of such antibodies in immunoassay of TNF. Yone et al. (EPO Patent Publication 0,288,088, Oct. 26, 1988) disclosed anti-TNF antibodies, including mAbs, and their utility in immunoassay diagnosis of pathologies, in particular Kawasaki's pathology and bacterial infection. The body fluids of patients with Kawasaki's pathology (infantile acute febrile mucocutaneous lymph node syndrome; Kawasaki, T., *Allergy* 16:178 (1967); Kawasaki, T., *Shonica (Pediatrics)* 26:935 (1985)) were said to contain elevated TNF levels which were related to progress of the pathology (Yone et al., supra).

Accordingly, there is a need to provide molecules that are involved in pathological conditions. Such novel proteins could be useful in augmenting the immune system in such areas as immune recognition, antigen presentation, and immune system activation. Antibodies or antagonists directed against these proteins may be useful in reducing or eliminating disorders associated with TNF and TNF-like cytokines, such as endotoxic shock and auto-immune disorders, for example.

SUMMARY OF THE INVENTION

The present invention provides isolated nucleic acid molecules comprising polynucleotides encoding three novel proteins that are structurally similar to a human Peptidoglycan Recognition Protein and murine Tag-7, and are believed to have similar biological effects and activities. The cytokines are named PGRP-K, PGRP-W. and PGRP-C, and the invention includes PGRP-K, PGRP-W, and PGRP-C polypeptides having at least a portion of the amino acid sequence in FIGS. 1A–B (SEQ ID NO:2), in FIGS. 2A–C (SEQ ID NO:4), and/or FIG. 3 (SEQ ID NO:6) or amino acid sequence encoded by the cDNA clones deposited on Dec. 23, 1998, assigned ATCC number 203564; Dec. 23, 1998, assigned ATCC number 203563; and Mar. 20, 1998, assigned ATCC number 209683, respectively. The nucleotide sequence determined by sequencing the deposited PGRP-K clone, which is shown in FIGS. 1A–B (SEQ ID NO:1), contains an open reading frame encoding a complete polypeptide of 243 amino acid residues including an N-terminal methionine, a predicted PGRP-like domain of about 83 amino acid residues, and a deduced molecular weight for the complete protein of about 27 kDa.

The nucleotide sequence determined by sequencing the deposited PGRP-W clone, which is shown in FIGS. 2A–C (SEQ ID NO:3), contains an open reading frame encoding a complete polypeptide of 368 amino acid residues including an N-terminal methionine, a predicted PGRP-like domain of about 83 amino acid residues, and a deduced molecular weight for the complete protein of about 40 kDa.

The nucleotide sequence determined by sequencing the deposited PGRP-C clone, which is shown in FIG. 3 (SEQ ID NO:5), contains an open reading frame encoding a complete polypeptide of 196 amino acid residues including an N-terminal methionine, a predicted PGRP-like domain of about 83 amino acid residues, and a deduced molecular weight for the complete protein of about 21 kDa.

Thus, one aspect of the invention provides isolated nucleic acid molecules comprising polynucleotides having nucleotide sequences selected from the group consisting of: (a) a nucleotide sequence encoding a full-length PGRP-K, PGRP-W, or PGRP-C polypeptide having the complete amino acid sequence in FIGS. 1A–B (SEQ ID NO:2), in FIGS. 2A–C (SEQ ID NO:4), or in FIG. 3 (SEQ ID NO:6), respectively, or as encoded by the cDNA clones contained in the ATCC Deposit number 203564, deposited on Dec. 23, 1998; ATCC Deposit number 203563, deposited on Dec. 23, 1998; and ATCC Deposit number 209683, deposited Mar. 20, 1998, respectively.; (b) a nucleotide sequence encoding the predicted PGRP-like domain of the PGRP-K polypeptide having the amino acid sequence at positions 24 to 107 in FIGS. 1A–B (SEQ ID NO:2), the predicted PGRP-like domain of the PGRP-W polypeptide having the amino acid sequence at positions 52 to 135 in FIGS. 2A–C (SEQ ID NO:4), and/or the predicted PGRP-like domain of the PGRP-C polypeptide having the amino acid sequence at positions 34 to 117 in FIG. 3 (SEQ ID NO:6), or as encoded by the cDNA clones contained in ATCC Numbers 203564, 203563, and 209683, respectively, deposited on Dec. 23, 1998, and Mar. 20, 1998; or as encoded by the cDNA clones contained in ATCC Numbers 203564, 203563, and 209683, respectively, deposited on Dec. 23, 1998, and Mar. 20, 1998; (c) a nucleotide sequence encoding a soluble PGRP-K, PGRP-W, and/or PGRP-C polypeptide having the PGRP-like domain but lacking the leader sequence; and (d) a nucleotide sequence complementary to any of the nucleotide sequences in (a), (b), or (c) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), or (d) above, or a polynucleotide which hybridizes under stringent hybridization conditions to a polynucleotide in (a), (b), (c), or (d) above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a PGRP-K, a PGRP-W, or a PGRP-C polypeptide having an amino acid sequence in (a), (b), or above.

The present invention also relates to recombinant vectors, which include the isolated nucleic acid molecules of the present invention, and to host cells containing the recombinant vectors, as well as to methods of making such vectors and host cells and for using them for the production of PGRP-K, PGPR-W, and/or PGRP-C polypeptides or peptides by recombinant techniques.

The invention further provides isolated PGRP-K, PGRP-W, and PGRP-C polypeptides comprising amino acid sequences selected from the group consisting of: (a) the amino acid sequence of the full-length PGRP-K polypeptide having the complete amino acid sequence shown in FIGS. 1A–B (SEQ ID NO:2), the amino acid sequence of the full-length PGRP-W polypeptide having the complete amino acid sequence shown in FIGS. 2A–C (SEQ ID NO:4), the amino acid sequence of the full-length PGRP-C polypeptide having the complete amino acid sequence shown in FIG. 3 (SEQ ID NO:6), or as encoded by the cDNA clones contained in ATCC Numbers 203564, 203563, and 209683, respectively, deposited on Dec. 23, 1998, and Mar. 20, 1998; (b) the amino acid sequence of the predicted PGRP-like domain of the PGRP-K polypeptide having the amino acid sequence at positions 24 to 107 in FIGS. 1A–B (SEQ ID NO:2), the predicted PGRP-like domain of the PGRP-W polypeptide having the amino acid sequence at positions 52 to 135 in FIGS. 2A–C (SEQ ID NO:4), and/or the predicted PGRP-like domain of the PGRP-C polypeptide having the amino acid sequence at positions 34 to 117 in FIG. 3 (SEQ ID NO:6), or as encoded by the cDNA clones contained in ATCC Numbers 203564, 203563, and 209683, respectively, deposited on Dec. 23, 1998, and Mar. 20, 1998; (c) the amino acid sequence of the soluble PGRP-K, PGRP-W, and/or PGRP-C polypeptide having the PGRP-like domain but lacking the leader sequence, wherein each of these domains is defined below.

The polypeptides of the present invention also include polypeptides having an amino acid sequence with at least 90% similarity, and more preferably at least 95% similarity to those described in (a), (b), or (c) above, as well as polypeptides having an amino acid sequence at least 80% identical, more preferably at least 90% identical, and still more preferably 95%, 96%, 97%, 98% or 99% identical to those above.

An additional embodiment of this aspect of the invention relates to a peptide or polypeptide which has the amino acid sequence of an epitope-bearing portion of a PGRP-K, a PGRP-W, or a PGRP-C polypeptide having an amino acid sequence described in (a), (b), or (c) above. Peptides or polypeptides having the amino acid sequence of an epitope-bearing portion of a PGRP-K, a PGRP-W, or a PGRP-C polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention. In another embodiment, the invention provides an isolated antibody that binds specifically to a polypeptide having an amino acid sequence described in (a), (b), or (c) above.

The invention further provides methods for isolating antibodies that bind specifically to an PGRP-K, PGRP-W, or PGRP-C polypeptide having an amino acid sequence as described herein. Such antibodies are useful diagnostically or therapeutically as described below.

The invention also provides for pharmaceutical compositions comprising soluble PGRP-K, PGRP-W, and/or PGRP-C polypeptides, particularly human PGRP-K, PGRP-W, and/or PGRP-C polypeptides, which may be employed, for instance, to treat tumor and tumor metastasis, infections by bacteria, viruses and other parasites, immunodeficiencies, inflammatory diseases, regulate the apoptosis and/or proliferation of keratinocytes, epidermal cells, and epithelial cells, mediate antigen processing and presentation, mediate cell activation and proliferation, and are functionally linked as primary mediators of immune recognition and immune responses.

The invention further provides compositions comprising a PGRP-K, PGRP-W, or PGRP-C polynucleotide or a PGRP-K, PGRP-W, or PGRP-C polypeptide for administration to cells in vitro, to cells ex vivo and to cells in vivo, or to a multicellular organism. In certain particularly preferred embodiments of this aspect of the invention, the compositions comprise a PGRP-K, PGRP-W, or PGRP-C polynucleotide for expression of a PGRP-K, PGRP-W, or PGRP-C polypeptide in a host organism for treatment of disease. Particularly preferred in this regard is expression in a human patient for treatment of a dysfunction associated with aberrant endogenous activity of a PGRP-K, PGRP-W, or PGRP-C gene.

The present invention also provides a screening method for identifying compounds capable of enhancing or inhibiting a cellular response induced by PGRP-K, PGRP-W, or PGRP-C which involves contacting cells which express PGRP-K, PGRP-W, or PGRP-C with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

In another aspect, a method for identifying PGRP-K, PGRP-W, or PGRP-C receptors is provided, as well as a screening assay for agonists and antagonists using such receptors. This assay involves determining the effect a candidate compound has on PGRP-K, PGRP-W, or PGRP-C binding to the PGRP-K, PGRP-W, or PGRP-C receptor. In particular, the method involves contacting a PGRP-K, PGRP-W, or PGRP-C receptor with an PGRP-K, PGRP-W, or PGRP-C polypeptide and a candidate compound and determining whether PGRP-K, PGRP-W, or PGRP-C polypeptide binding to the PGRP-K, PGRP-W, or PGRP-C receptor is increased or decreased due to the presence of the candidate compound. The antagonists may be employed to prevent septic shock, inflammation, and to regulate the growth activity of keratinocytes.

The present inventors have discovered that PGRP-K, PGRP-W, and PGRP-C is expressed in keratinocytes, wound healing tissues, and chondrosarcomas, respectively. For a number of disorders of these tissues and cells, such as tumor and tumor metastasis, infection of bacteria, viruses and other parasites, immunodeficiencies, septic shock, apoptosis or proliferation of these tissues, and proper antigen processing and presentation, it is believed that significantly higher or lower levels of the PGRP-K, PGRP-W, or PGRP-C gene expression can be detected in certain tissues (e.g., keratinocytes, wound-healing tissues, and chondrosarcoma) or bodily fluids (e.g., serum, plasma, urine, synovial fluid or spinal fluid) taken from an individual having such a disorder, relative to a "standard" PGRP-K, PGRP-W, or PGRP-C gene expression level, i.e., the PGRP-K, PGRP-W, or PGRP-C expression level in tissue or bodily fluids from an individual not having the disorder. Thus, the invention provides a diagnostic method useful during diagnosis of a disorder, which involves: (a) assaying PGRP-K, PGRP-W, or PGRP-C gene expression levels in cells or body fluid of an individual; (b) comparing the PGRP-K, PGRP-W, or PGRP-C gene expression level with a standard PGRP-K, PGRP-W, or PGRP-C gene expression level, whereby an increase or decrease in the assayed PGRP-K, PGRP-W, or PGRP-C gene expression level compared to the standard expression level is indicative of a disorder.

An additional aspect of the invention is related to a method for treating an individual in need of an increased level of either PGRP-K, PGRP-W, or PGRP-C activity in the body comprising administering to such an individual a composition comprising a therapeutically effective amount of an isolated PGRP-K, PGRP-W, or PGRP-C polypeptide of the invention or an agonist thereof.

A still further aspect of the invention is related to a method for treating an individual in need of a decreased level of either PGRP-K, PGRP-W, or PGRP-C activity in the body comprising, administering to such an individual a composition comprising a therapeutically effective amount of a PGRP-K, PGRP-W, or PGRP-C antagonist. Preferred antagonists for use in the present invention are either PGRP-K, PGRP-W, or PGRP-C-specific antibodies.

BRIEF DESCRIPTION OF THE FIGURES

FIGS. 1A–B show the nucleotide sequence (SEQ ID NO:1) and deduced amino acid sequence (SEQ ID NO:2) of the PGRP-K. The deduced complete amino acid sequence includes 243 amino acid residues and has a deduced molecular weight of about 27,000 Da. The predicted domains of the PGRP-K are: signal sequence (amino acid residues Met-1 to about Ala-17 of SEQ ID NO:2) and PGRP-like domain (amino acid residues from about Val-24 to about His-107 of SEQ ID NO:2).

FIGS. 2A–C show the nucleotide sequence (SEQ ID NO:3) and deduced amino acid sequence (SEQ ID NO:4) of the PGRP-W. The deduced complete amino acid sequence includes 368 amino acid residues and has a deduced molecular weight of about 40,286 Da. The predicted domains of the PGRP-W are: signal sequence (amino acid residues Met-1 to about Gly-17 of SEQ ID NO:4) and PGRP-like domain (amino acid residues from about Val-52 to about His-135 of SEQ ID NO:4).

FIGS. 3 show the nucleotide sequence (SEQ ID NO:5) and deduced amino acid sequence (SEQ ID NO:6) of the PGRP-C. The deduced complete amino acid sequence includes 196 amino acid residues and has a deduced molecular weight of about 21,500 Da. The predicted domains of the PGRP-C are: signal sequence (amino acid residues Met-1 to about Ala-21 of SEQ ID NO:6) and PGRP-like domain (amino acid residues from about Val-34 to about His-117 of SEQ ID NO:6).

FIGS. 4A–B show the regions of similarity between the amino acid sequences of the PGRP-K protein of FIGS. 1A–B (labeled PGRP-K (HKABZ65); SEQ ID NO:2), the PGRP-W protein of FIGS. 2A–C (labeled PGRP-W (HWHGB15); SEQ ID NO:4), the PGRP-C protein of FIG. 3 (labeled PGRP-C (HCDDP40); SEQ ID NO:6), and the Mouse Tag-7 protein (SEQ ID NO:7) (GenBank Accession Number X86374), as determined by the "Megalign" routine which is part of the computer program called "DNAStar". Identical amino acid residues between these protein sequences are shaded.

DETAILED DESCRIPTION

Figure 2C:
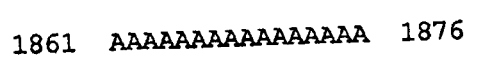
Figure 5:
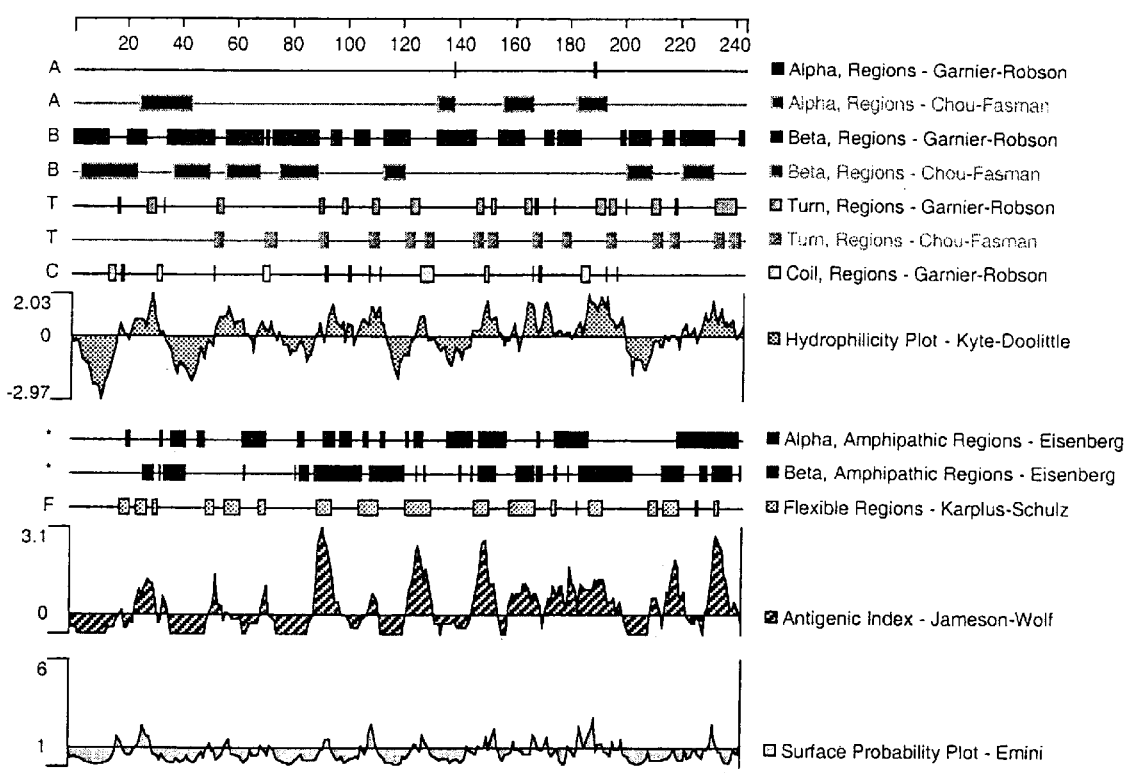
FIG. 5 and Table II show a structural analysis of the PGRP-K amino acid sequence of FIGS. 1A–B (SEQ ID NO:2), generated using the default parameters of the recited computer programs. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues: Val-24 to Ala-35; from Gln-51 to Gln-58; from Gly-69 to Ser-72; from Leu-88 to Gly-100; from His-107 to Tyr-111; from Gly-122 to Pro-131; from Gln-146 to Ile-155; from Leu-159 to His-170; from Val-172 to Pro-200; from Gly-211 to Val-223; and from Phe-230 to Tyr-242 as depicted in FIGS. 1A–B (SEQ ID NO:2) correspond to the shown highly antigenic regions of the PGRP-K protein.

The present invention provides isolated nucleic acid molecules comprising polynucleotides encoding a PGRP-K, a PGRP-W and a PGRP-C polypeptides (FIGS. 1A–B, 2A–C, and 3 (SEQ ID NO:1, SEQ ID NO:3, and SEQ ID NO:5, respectively), the amino acid sequences of which were determined by sequencing cloned cDNAs. The PGRP-K, PGRP-W, and PGRP-C proteins shown in FIGS. 1A–B, 2A–C, and 3, respectively, share sequence homology with the murine Tag-7 protein (FIGS. 4A–B (SEQ ID NO:7)). On Dec. 23, 1998, and Mar. 20, 1998, deposits of plasmid DNAs encoding PGRP-K, PGRP-W, and PGRP-C were made at the American Type Culture Collection, 10801 University Boulevard, Manassas, Va. 20110-2209, and given accession numbers 203564, 203563, and 209683, respectively. The nucleotide sequences shown in FIGS. 1, 2, and 3 (SEQ ID NO:1, SEQ ID NO:3, and SEQ ID NO:5, respectively) were obtained by sequencing cDNA clones (Clone ID HKABZ65, HWHGB15, and HCDDP40, respectively) containing the same amino acid coding sequences as the clones in ATCC Accession Nos. 203564, 203563, and 209683, respectively. The deposited clone encoding PGRP-K is contained in the pCMVSport2.0 plasmid (Life Technologies, Rockville, Md.), the deposited clone encoding PGRP-W is contained in the pCMVSport3.0 plasmid (Life Technologies, Rockville, Md.), and the deposited clone encoding the PGRP-C is contained in the Uni-Zap XR plasmid (Stratagene, La Jolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequences in FIGS. 1 or 2, a nucleic acid molecule of the present invention encoding a peptidoglycan recognition protein polypeptide may be obtained using standard cloning and screening procedures, such as those for cloning cDNAs using mRNA as starting material. Illustrative of the invention, the nucleic acid molecule described in FIG. 1 (SEQ ID NO:1) was discovered in a cDNA library derived from Human keratinocytes, the nucleic acid molecule described in FIG. 2 (SEQ ID NO:3) was discovered in cDNA libraries derived from Human keratinocytes and Human tissues undergoing wound-healing, and the nucleic acid molecule described in FIG. 3 (SEQ ID NO:5) was discovered in cDNA libraries derived from Human chondrosarcoma.

The PGRP-K gene contains an open reading frame encoding a protein of about 243 amino acid residues, a PGRP-like domain of about 137 amino acids (amino acid residues from about 18 to about 155 in FIGS. 1A–B (SEQ ID NO:2)), and a deduced molecular weight of about 27 kDa. The PGRP-K protein shown in FIGS. 1A–B (SEQ ID NO:2) is about 40% similar to the mouse Tag-7 protein which can be accessed on Genbank as Accession No. X86374.

The PGRP-W gene contains an open reading frame encoding a protein of about 368 amino acid residues, a PGRP-like domain of about 175 amino acids (amino acid residues from about 18 to about 193 in FIGS. 2A–C (SEQ ID NO:4)), and a deduced molecular weight of about 40.2 kDa. The PGRP-W protein shown in FIGS. 2A–C (SEQ ID NO:4) is about 32% similar to the mouse Tag-7 protein which can be accessed on Genbank as Accession No. X86374.

The PGRP-C gene contains an open reading frame encoding a protein of about 196 amino acid residues, a PGRP-like domain of about 98 amino acids (amino acid residues from about 23 to about 120 in FIG. 3 (SEQ ID NO:6)), and a deduced molecular weight of about 21.5 kDa. The PGRP-C protein shown in FIG. 3 (SEQ ID NO:6) is about 67% similar to the mouse Tag-7 protein which can be accessed on Genbank as Accession No. X86374.

Furthermore, PGRP-W is 59% homologous to PGRP-K, PGRP-W is 42% homologous to PGRP-C, and PGRP-K is 39% homologous to PGRP-C. More importantly, PGRP-K, PGRP-W, and PGRP-C share a conserved region of homology amongst the sequences, as well as with the murine Tag-7 protein. Also, four conserved cysteines are also homologous amongst all of these sequences, as can be seen in FIGS. 4A–B. Based upon alignments and sequence distances, it appears as if these three PGRPs constitute a novel class of peptidoglycan binding proteins, which share a conserved domain (PGRP-like domain), which may function in binding, while also having significantly diverging regions of homology as well. Thus, it appears as each of these PGRPs is a novel member of a family of peptidoglycan binding proteins thought to play an important role in immune recognition, immune surveilance, antigen presentation, and immune system activation.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically. Isolated nucleic acid molecules of the present invention include DNA molecules comprising an open reading frame (ORF) with an initiation codon starting at position 70 of the nucleotide sequence shown in FIGS. 1A–B (SEQ ID NO:1), an initiation codon starting at position 106 of the nucleotide sequence shown in FIGS. 2A–C (SEQ ID NO:3), and an initiation codon starting at position 55 of the nucleotide sequence shown in FIG. 3 (SEQ ID NO:5). As one of ordinary skill would appreciate, due to the possibilities of sequencing errors discussed above, the actual complete PGRP-C polypeptide encoded by the deposited cDNA, which comprises about 196 amino acids, may be somewhat shorter. In particular, the determined PGRP-C coding sequence contains a second methionine codon which may serve as an alternative start codon for translation of the open reading frame, at nucleotide positions 70–72 in FIG. 3 (SEQ ID NO:5). More generally, the actual open reading frame may be anywhere in the range of ±10 amino acids, more likely in the range of ±6 amino acids, of that predicted from either the first or second methionine codon from the N-terminus shown in FIG. 3 (SEQ ID NO:5). In addition, isolated nucleic acid molecules of the invention include DNA molecules which comprise a sequence substantially different from those described above but which, due to the degeneracy of the genetic code, still encode either the PGRP-K, PGRP-W, or PGRP-C proteins. Of course, the genetic code is well known in the art. Thus, it would be routine for one skilled in the art to generate the degenerate variants described above. In another aspect, the invention provides isolated nucleic acid molecules encoding the PGRP-K, PGRP-W, and PGRP-C polypeptides having amino acid sequences encoded by the cDNAs contained in the plasmids deposited on Dec. 23, 1998, and Mar. 20, 1998.

The invention further provides an isolated nucleic acid molecule having the nucleotide sequence shown in FIGS. 1A–B (SEQ ID NO:1) or the nucleotide sequence of the PGRP-K cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the PGRP-K gene in human tissue, for instance, by Northern blot analysis.

The invention further provides an isolated nucleic acid molecule having the nucleotide sequence shown in FIGS. 2A–C (SEQ ID NO:3) or the nucleotide sequence of the PGRP-W cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the PGRP-W gene in human tissue, for instance, by Northern blot analysis.

The invention further provides an isolated nucleic acid molecule having the nucleotide sequence shown in FIG. 3 (SEQ ID NO:5) or the nucleotide sequence of the PGRP-C cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the PGRP-C gene in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO:1 which consists of positions 1–534 of SEQ ID NO:1, a polynucleotide having a nucleotide sequence representing the portion of SEQ ID NO:1 which consists of positions 535–798 of SEQ ID NO:1, a polynucleotide having a nucleotide sequence representing the portion of SEQ ID NO:3 which consists of positions 1–685 of SEQ ID NO:3, a polynucleotide having a nucleotide sequence representing the portion of SEQ ID NO:3 which consists of positions 686–1210 of SEQ ID NO:3, a polynucleotide having a nucleotide sequence representing the portion of SEQ ID NO:5 which consists of positions 1–414 of SEQ ID NO:5, and a polynucleotide having a nucleotide sequence representing the portion of SEQ ID NO:5 which consists of positions 415–642 of SEQ ID NO:5.

Further, the invention includes a polynucleotide comprising a sequence at least 95% identical to any portion of at least about 30 contiguous nucleotides, preferably at least about 50 nucleotides, of the sequence from nucleotides 1 to nucleotide 1150 in FIGS. 1A–B (SEQ ID NO:1), from nucleotides 1 to nucleotide 1854 in FIGS. 2A–C (SEQ ID NO:3), and from nucleotides I to nucleotide 726 in FIG. 3 (SEQ ID NO:5).

More generally, by a fragment of an isolated nucleic acid molecule having the nucleotide sequence of the deposited cDNA or the nucleotide sequences shown in FIGS. 1A–B (SEQ ID NO:1), in FIGS. 2A–C (SEQ ID NO:3), or in FIG. 3 (SEQ ID NO:5) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–300 nt in length are also useful according to the present invention as are fragments corresponding to most, if not all, of the nucleotide sequence of the deposited cDNA or as shown in FIGS. 1A–B (SEQ ID NO:1), in FIGS. 2A–C (SEQ ID NO:3), and/or FIG. 3 (SEQ ID NO:5). By a fragment at least 20 nt in length, for example, is intended fragments which include 20 or more contiguous bases from the nucleotide sequences of the deposited cDNAs or the nucleotide sequences as shown in FIGS. 1A–B (SEQ ID NO:1), in FIGS. 2A–C (SEQ ID NO:3), or in FIG. 3 (SEQ ID NO:5). Preferred nucleic acid fragments of the present invention include nucleic acid molecules encoding epitope-bearing portions of the PGRP-K, PGRP-W, and/or PGRP-C polypeptides as identified in FIG. 5 and Table II, FIG. 6 and Table III, and FIG. 7 and Table IV, respectively, and described in more detail below.

In another aspect, the invention provides isolated nucleic acid molecules comprising polynucleotides which hybridizes under stringent hybridization conditions to a portion of the polynucleotide in a nucleic acid molecule of the invention described above, for instance, the cDNA clones contained in ATCC Deposit numbers 203564, 203563, or 209683, respectively, deposited on Dec. 23, 1998, and Mar. 20, 1998. By "stringent hybridization conditions" is intended overnight incubation at 42° C. in a solution comprising: 50% formamide, 5×SSC (750 mM NaCl, 75 mM trisodium citrate), 75 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 50) nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotides (e.g., the deposited cDNA or the nucleotide sequence as shown in FIGS. 1A–B (SEQ ID NO:1), in FIGS. 2A–C (SEQ ID NO:3), and/or in FIG. 3 (SEQ ID NO:5)). Of course, a polynucleotide which hybridizes only to a poly A sequence (such as the 3' terminal poly(A) tract of the PGRP-K, PGRP-W, or PGRP-C cDNA shown in FIGS. 1A–B (SEQ ID NO:1), in FIGS. 2A–C (SEQ ID NO:3), and/or FIG. 3 (SEQ ID NO:5)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a PGRP-K polypeptide may include, but are not limited to those encoding the amino acid sequence of the PGRP-like domain of the polypeptide, by itself; and the coding sequence for the PGRP-like domain of the polypeptide and additional sequences, such as a pre-, or pro- or prepro-protein sequence.

As indicated, nucleic acid molecules of the present invention which encode a PGRP-W polypeptide may include, but are not limited to those encoding the amino acid sequence of the PGRP-like domain of the polypeptide, by itself; and the coding sequence for the PGRP-like domain of the polypeptide and additional sequences, such as a pre-, or pro- or prepro-protein sequence.

As indicated, nucleic acid molecules of the present invention which encode a PGRP-C polypeptide may include, but are not limited to those encoding the amino acid sequence of the PGRP-like domain of the polypeptide, by itself; and the coding sequence for the PGRP-like domain of the polypeptide and additional sequences, such as a pre-, or pro or prepro-protein sequence.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include either the PGRP-K, PGRP-W, or the PGRP-C fused to Fc at the N- or C-terminus.

Variant and Mutant Polynucleotides

The present invention further relates to variants of the nucleic acid molecules of the present invention, which encode portions, analogs or derivatives of either the PGRP-K, PGRP-W, or PGRP-C proteins. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of either the PGRP-K, PGRP-W, and/or PGRP-C proteins or portions thereof. Also especially preferred in this regard are conservative substitutions.

Most highly preferred are nucleic acid molecules encoding the PGRP-like domain 1 of the protein having the amino acid sequence shown in FIGS. 1A–B (SEQ ID NO:2) or the PGRP-like domain of the PGRP-K amino acid sequence encoded by the deposited cDNA clone, the nucleic acid molecules encoding the PGRP-like domain of the protein having the amino acid sequence shown in FIGS. 2A–C (SEQ ID NO:4) or the PGRP-like domain of the PGRP-W amino acid sequence encoded by the deposited cDNA clone, or the nucleic acid molecules encoding the PGRP-like domain of the protein having the amino acid sequence shown in FIG. 3 (SEQ ID NO:6) or the PGRP-like domain of the PGRP-C amino acid sequence encoded by the deposited cDNA clone. Further embodiments include an isolated nucleic acid molecule comprising a polynucleotide having a nucleotide sequence at least 90% identical, and more preferably at least 95%, 96%, 97%, 98% or 99% identical to a polynucleotide selected from the group consisting of: (a) nucleotide sequences encoding either the PGRP-K, PGRP-W, or PGRP-C polypeptides having the complete amino acid sequences in FIGS. 1A–B (SEQ ID NO:2), in FIGS. 2A–C (SEQ ID NO:4), and/or in FIG. 3 (SEQ ID NO:6); (b) a nucleotide sequence encoding the predicted PGRP-like domain of the PGRP-K, PGRP-W, and PGRP-C polypeptides having the amino acid sequences at positions 72–323 in FIGS. 1A–B (SEQ ID NO:2), the amino acid sequences at positions 156–407 in FIGS. 2A–C (SEQ ID NO:4), and the amino acid sequence at positions 102–353 in FIG. 3 (SEQ ID NO:6), respectively; (c) a nucleotide sequence encoding the PGRP-K, PGRP-W, or PGRP-C polypeptides having the complete amino acid sequences encoded by the cDNA clones contained in ATCC Numbers 203564, 203563, and 209683, respectively, deposited on Dec. 23, 1998, and Mar. 20, 1998; (d) a nucleotide sequence encoding the PGRP-like domain of the PGRP-K, PGRP-W, or PGRP-C polypeptides having the amino acid sequences encoded by the cDNA clones contained in ATCC Numbers 203564, 203563, and 209683, respectively, deposited on Dec. 23, 1998, and Mar. 20, 1998; and (e) a nucleotide sequence complementary to any of the nucleotide sequences in (a), (b), (c) or (d) above.

By a polynucleotide having a nucleotide sequence at least, for example, 95% "identical" to a reference nucleotide sequence encoding a PGRP-K, a PGRP-W, or a PGRP-C polypeptide is intended that the nucleotide sequence of the polynucleotide is identical to the reference sequence(s) except that the polynucleotide sequence may include up to five point mutations per each 100 nucleotides of the reference nucleotide sequence encoding either the PGRP-K, PGRP-W, or PGRP-C polypeptides. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequences shown in FIGS. 1A–B, FIGS. 2A–C, and/or FIG. 3 or to the nucleotide sequences of the deposited cDNA clones can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482–489 (1981), to find the best segment of homology between two sequences. When using Bestfit or any other sequence aligument program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequences shown in FIGS. 1A–B (SEQ ID NO:1), FIGS. 2A–C (SEQ ID NO:3), and/or FIG. 3 (SEQ ID NO:5) or to the nucleic acid sequence(s) of the deposited cDNAs, irrespective of whether they encode a polypeptide having PGRP-K, PGRP-W, or PGRP-C activities, respectively. This is because even where a particular nucleic acid molecule does not encode a polypeptide having either PGRP-K, PGRP-W, or PGRP-C activities, one of skill in the art would still know how to use the nucleic acid molecules, for instance, as a hybridization probe or a polymerase chain reaction (PCR) primer. Uses of the nucleic acid molecules of the present invention that do not encode a polypeptide having either PGRP-K, PGRP-W, or PGRP-C activity include, inter alia, (1) isolating the PGRP-K, PGRP-W, or PGRP-C genes or allelic variants thereof in cDNA libraries; (2) in situ hybridization (e.g., "FISH") to metaphase chromosomal spreads to provide precise chromosomal location of the PGRP-K, PGRP-W, or PGRP-C genes, as described in Verma et al., *Human Chromosomes: A Manual of Basic Techniques*, Pergamon Press, New York (1988); and Northern Blot analysis for detecting either PGRP-K, PGRP-W, or PGRP-C mRNA expression in specific tissues.

Preferred, however, are nucleic acid molecules having sequences at least 90%, 95%, 96%, 97%, 98% or 99% identical to the nucleic acid sequences shown in FIGS. 1A–B (SEQ ID NO:1), FIGS. 2A–C (SEQ ID NO:3), and/or FIG. 3 (SEQ ID NO:5), or to the nucleic acid sequence of the deposited cDNAs which do, in fact, encode a polypeptide(s) having either PGRP-K, PGRP-W, or PGRP-C protein activity. By "a polypeptide having PGRP-K, PGRP-W, or PGRP-C activity" is intended polypeptides exhibiting activity similar, but not necessarily identical, to an activity of the PGRP-K, PGRP-W, or PGRP-C proteins of the invention, as measured in a particular biological assay. For example, the PGRP-K, PGRP-W, or PGRP-C proteins of the present invention bind insoluble peptidoglycan. An insoluble peptidoglycan binding assay for measuring the ability of a protein to bind to insoluble peptidoglycan can be performed by using reagents well known and commonly available in the art for detecting this binding ability. For instance, numerous such assays for peptidoglycan binding protein activities are described in the various references in the Background section of this disclosure, above, as well as in example 13. Briefly, such an assay involves collecting insoluble peptidoglycan from an appropriate source (e.g., *Micrococcus luteus*), mixing the insoluble peptidoglycan with a specified amount of the protein in question, and measuring the concentration of peptidoglycan bound by the protein over a certain period of time. Such insoluble peptidoglycan binding activities as can be measure in this type of assay are useful for identifying proteins that may have a immuno-modulatory effect in the body, and that may act to bind peptidoglycan and/or function in an immune recognition capacity during the infection process of certain bacterial species.

PGRP-K, PGRP-W, and/or PGRP-C proteins bind insoluble peptidoglycan, and are useful for identifying proteins that may have a immuno-modulatory effect in the body, and that may act to bind peptidoglycan and/or function in an immune recognition capacity during the infection process of certain bacterial species. Thus, "a polypeptide having PGRP-K, PGRP-W, and/or PGRP-C protein activity" includes polypeptides that also exhibit any of the same peptidoglycan binding activities in the above-described assays. Although the degree of peptidoglycan binding activity need not be identical to that of the PGRP-K, PGRP-W, and/or PGRP-C proteins, preferably, "a polypeptide having either PGRP-K, PGRP-W, and/or PGRP-C protein activity" will exhibit substantially similar peptidoglycan binding in a given activity as compared to the PGRP-K, PGRP-W, and/or PGRP-C proteins (i.e., the candidate polypeptide will exhibit greater activity or not more than about 25-fold less and, preferably, not more than about tenfold less activity relative to the reference PGRP-K, PGRP-W, and/or PGRP-C proteins). Assays for measuring such activity are known in the art. For example, see Yoshida et al., JBC, 271 (23): 13854 (1996); and Kang et al., PNAS (US), 95 (17): 10078 (1998).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequences of the deposited cDNAs or the nucleic acid sequences shown in FIGS. 1A–B (SEQ ID NO:1), in FIGS. 2A–C (SEQ ID NO:3), and/or FIG. 3 (SEQ ID NO:5) will encode a polypeptide "having PGRP-K, PGRP-W, and/or PGRP-C protein activity." In fact, since degenerate variants of these nucleotide sequences all encode the same polypeptides, respectively, this will be clear to the skilled artisan even without performing the above described comparison assay. It will be further recognized in the art that, for such nucleic acid molecules that are not degenerate variants, a reasonable number will also encode polypeptides having either PGRP-K, PGRP-W, and/or PGRP-C protein activity, respectively. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

The present invention also relates to vectors which include the isolated DNA molecules of the present invention, host cells which are genetically engineered with the recombinant vectors, and the production of either PGRP-K, PGRP-W, and/or PGRP-C polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells. The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert(s) should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the PGRP-K, PGRP-W, and/or PGRP-C transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS, 293 and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pHE4 (HGS Inc., Provisional Number: PCT/US98/20075); pA2, PO4, and pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Selection of appropriate vectors and promoters for expression in a host cell is a well known procedure and the requisite techniques for expression vector construction, introduction of the vector into the host and expression in the host are routine skills in the art.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., PGRP-K, PGRP-W, and/or PGRP-C coding sequences), and/or to include genetic material (e.g., heterologous polynucleotide sequences) that is operably associated with PGRP-K, PGRP-W, and/or PGRP-C polynucleotides of the invention, respectively, and which activates, alters, and/or amplifies endogenous PGRP-K, PGRP-W, and/or PGRP-C polynucleotides, respectively. For example, techniques known in the art may be used to operably associate heterologous control regions (e.g., promoter and/or enhancer) and endogenous PGRP-K, PGRP-W, and/or PGRP-C polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., glycosylation, phosphorylation, cleavage) of proteins. Appropriate cell lines can be chosen to ensure the desired modifications and processing of the foreign protein expressed.

Introduction of the construct into the host cell can be effected by calcium phosphate transfection, DEAE-dextran mediated transfection, cationic lipid-mediated transfection, electroporation, transduction infection or other methods. Such methods are described in many standard laboratory manuals, such as Davis et al., Basic Methods In Molecular Biology (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5 has been fused with Fc portions for the purpose of high-throughput screening assays to identify antagonists of hIL-5. See, D. Bennett et at., *J. Molecular Recognition* 8:52–58 (1995) and K. Johanson et al., *J. Biol. Chem.* 270:9459–9471 (1995).

The PGRP-K, PGRP-W, or PGRP-C protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

PGRP-K, PGRP-W, and PGRP-C Polypeptides and Fragments

The invention further provides an isolated PGRP-K polypeptide having the amino acid sequence encoded by the deposited cDNA, or the amino acid sequence in FIGS. 1A–B (SEQ ID NO:2), or a peptide or polypeptide comprising a portion of the above polypeptides.

The invention further provides an isolated PGRP-W polypeptide having the amino acid sequence encoded by the deposited cDNA, or the amino acid sequence in FIGS. 2A–C (SEQ ID NO:4), or a peptide or polypeptide comprising a portion of the above polypeptides.

The invention further provides an isolated PGRP-C polypeptide having the amino acid sequence encoded by the deposited cDNA, or the amino acid sequence in FIG. 3 (SEQ ID NO:6), or a peptide or polypeptide comprising a portion of the above polypeptides.

Variant and Mutant Polypeptides

To improve or alter the characteristics of either PGRP-K, PGRP-W, and/or PGRP-C polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

N-Terminal and C-Terminal Deletion Mutants

For instance, for many proteins, including the extracellular domain or the mature form(s) of a secreted protein, it is known in the art that one or more amino acids may be deleted from the N-terminus or C-terminus without substantial loss of biological function. For instance, Ron et al., *J. Biol. Chem.*, 268:2984–2988 (1993) reported modified KGF proteins that had heparin binding activity even if 3, 8, or 27 amino-terminal amino acid residues were missing.

In the present case, since the protein of the invention is related to Tag-7, deletions of N-terminal amino acids up to the Gly (G) residue at position 191 in FIG. 1 (SEQ ID NO:2) may retain some biological activity such as cytotoxicity to appropriate target cells. However, even if deletion of one or more amino acids from the N-terminus of a protein results in modification of loss of one or more biological functions of the protein, other biological activities may still be retained. Thus, the ability of the shortened protein to induce and/or bind to antibodies which recognize the complete PGRP-like domain of the protein generally will be retained when less than the majority of the residues of the complete PGRP domain of the protein are removed from the N-terminus. Whether a particular polypeptide lacking N-terminal residues of a complete protein retains such immunologic activities can readily be determined by routine methods described herein and otherwise known in the art.

In one embodiment, the present invention further provides polypeptides having one or more residues deleted from the amino terminus of the amino acid sequence of the PGRP-K polypeptide depicted in FIGS. 1A–B (SEQ ID NO:2) or encoded by the cDNA of the deposited clone. Particularly, in one embodiment, N-terminal deletions of the PGRP-K polypeptide can be described by the general formula m to 243, where m is an integer from 2 to 243 corresponding to the position of the amino acid identified in SEQ ID NO:2 and preferably, corresponds to one of the N-terminal amino acid residues identified in the N-terminal deletions specified herein. In specific embodiments, N-terminal deletions of the PGRP-K polypeptide of the invention comprise, or alternatively, consist of, amino acid residues: G-2 to Q-243; T-3 to Q-243; L-4 to Q-243; P-5 to Q-243; W-6 to Q-243; L-7 to Q-243; L-8 to Q-243; A-9 to Q-243; F-10 to Q-243; F-11 to Q-243; I-12 to Q-243; L-13 to Q-243; G-14 to Q-243; L-15 to Q-243; Q-16 to Q-243; A-17 to Q-243; W-18 to Q-243; D-19 to Q-243; T-20 to Q-243; P-21 to Q-243; T-22 to Q-243; I-23 to Q-243; V-24 to Q-243; S-25 to Q-243; R-26 to Q-243; K-27 to Q-243; E-28 to Q-243; W-29 to Q-243; G-30 to Q-243; A-31 to Q-243; R-32 to Q-243; P-33 to Q-243; L-34 to Q-243; A-35 to Q-243; C-36 to Q-243; R-37 to Q-243; A-38 to Q-243; L-39 to Q-243; L-40 to Q-243; T-41 to Q-243; L-42 to Q-243; P-43 to Q-243; V-44 to Q-243; A-45 to Q-243; Y-46 to Q-243; I-47 to Q-243; I-48 to Q-243; T-49 to Q-243; D-50 to Q-243; Q-51 to Q-243; L-52 to Q-243; P-53 to Q-243; G-54 to Q-243; M-55 to Q-243; Q-56 to Q-243; C-57 to Q-243; Q-58 to Q-243; Q-59 to Q-243; Q-60 to Q-243; S-61 to Q-243; V-62 to Q-243; C-63 to Q-243; S-64 to Q-243; Q-65 to Q-243; M-66 to Q-243; L-67 to Q-243; R-68 to Q-243; G-69 to Q-243; L-70 to Q-243; Q-71 to Q-243; S-72 to Q-243; H-73 to Q-243; S-74 to Q-243; V-75 to Q-243; Y-76 to Q-243; T-77 to Q-243; I-78 to Q-243; G-79 to Q-243; W-80 to Q-243; C-81 to Q-243; D-82 to Q-243; V-83 to Q-243; A-84 to Q-243; Y-85 to Q-243; N-86 to Q-243; F-87 to Q-243; L-88 to Q-243; V-89 to Q-243; G-90 to Q-243; D-91 to Q-243; D-92 to Q-243; G-93 to Q-243; R-94 to Q-243; V-95 to Q-243; Y-96 to Q-243; E-97 to Q-243; G-98 to Q-243; V-99 to Q-243; G-100 to Q-243; W-101 to Q-243; N-102 to Q-243; I-103 to Q-243; Q-104 to Q-243; G-105 to Q-243; L-106 to Q-243; H-107 to Q-243; T-108 to Q-243; Q-109 to Q-243; G-110 to Q-243; Y-111 to Q-243; N-112 to Q-243; N-113 to Q-243; I-114 to Q-243; S-115 to Q-243; L-116 to Q-243; G-117 to Q-243; I-118 to Q-243; A-119 to Q-243; F-120 to Q-243; F-121 to Q-243; G-122 to Q-243; N-123 to Q-243; K-124 to Q-243; I-125 to Q-243; S-126 to Q-243; S-127 to Q-243; S-128 to Q-243; P-129 to Q-243; S-130 to Q-243; P-131 to Q-243; A-132 to Q-243; A-133 to Q-243; L-134 to Q-243; S-135 to Q-243; A-136 to Q-243; A-137 to Q-243; E-138 to Q-243; G-139 to Q-243; L-140 to Q-243; I-141 to Q-243; S-142 to Q-243; Y-143 to Q-243; A-144 to Q-243; I-145 to Q-243; Q-146 to Q-243; K-147 to Q-243; G-148 to Q-243; H-149 to Q-243; L-150 to Q-243; S-151 to Q-243; P-152 to Q-243; R-153 to Q-243; Y-154 to Q-243; I-155 to Q-243; Q-156 to Q-243; P-157 to Q-243; L-158 to Q-243; L-159 to Q-243; L-160 to Q-243; K-161 to Q-243; E-162 to Q-243; E-163 to Q-243; T-164 to Q-243; C-165 to Q-243; L-166 to Q-243; D-167 to Q-243; P-168 to Q-243; Q-169 to Q-243; H-170 to Q-243; P-171 to Q-243; V-172 to Q-243; M-173 to Q-243; P-174 to Q-243; R-175 to Q-243; K-176 to Q-243; V-177 to Q-243; C-178 to Q-243; P-179 to Q-243; N-180 to Q-243; I-181 to Q-243; I-182 to Q-243; K-183 to Q-243; R-184 to Q-243; S-185 to Q-243; A-186 to Q-243; W-187 to Q-243; E-188 to Q-243; A-189 to Q-243; R-190 to Q-243; E-191 to Q-243; T-192 to Q-243; H-193 to Q-243;

C-194 to Q-243; P-195 to Q-243; K-196 to Q-243; M-197 to Q-243; N-198 to Q-243; L-199 to Q-243; P-200 to Q-243; A-201 to Q-243; K-202 to Q-243; Y-203 to Q-243; V-204 to Q-243; I-205 to Q-243; I-206 to Q-243; I-207 to Q-243; H-208 to Q-243; T-209 to Q-243; A-210 to Q-243; G-211 to Q-243; T-212 to Q-243; S-213 to Q-243; C-214 to Q-243; T-215 to Q-243; V-216 to Q-243; S-217 to Q-243; T-218 to Q-243; D-219 to Q-243; C-220 to Q-243; Q-221 to Q-243; T-222 to Q-243; V-223 to Q-243; V-224 to Q-243; R-225 to Q-243; N-226 to Q-243; I-227 to Q-243; Q-228 to Q-243; S-229 to Q-243; F-230 to Q-243; H-231 to Q-243; M-232 to Q-243; D-233 to Q-243; T-234 to Q-243; R-235 to Q-243; N-236 to Q-243; F-237 to Q-243; C-238 to Q-243; of SEQ ID NO:2. Polynucleotides encoding these polypeptides also are provided.

In one embodiment, the present invention further provides polypeptides having one or more residues deleted from the amino terminus of the amino acid sequence of the PGRP-W polypeptide depicted in FIGS. 2A–C (SEQ ID NO:4) or encoded by the cDNA of the deposited clone. Particularly, in one embodiment, N-terminal deletions of the PGRP-W polypeptide can be described by the general formula m to 368, where m is an integer from 2 to 368 corresponding to the position of the amino acid identified in SEQ ID NO:4 and preferably, corresponds to one of the N-terminal amino acid residues identified in the N-terminal deletions specified herein. In specific embodiments, N-terminal deletions of the PGRP-W polypeptide of the invention comprise, or alternatively, consist of, amino acid residues: L-2 to H-368; L-3 to H-368; W-4 to H-368; L-5 to H-368; L-6 to H-368; V-7 to H-368; F-8 to H-368; S-9 to H-368; A-10 to H-368; L-11 to H-368; G-12 to H-368; I-13 to H-368; Q-14 to H-368; A-15 to H-368; W-16 to H-368; G-17 to H-368; D-18 to H-368; S-19 to H-368; S-20 to H-368; W-21 to H-368; N-22 to H-368; K-23 to H-368; T-24 to H-368; Q-25 to H-368; A-26 to H-368; K-27 to H-368; Q-28 to H-368; V-29 to H-368; S-30 to H-368; E-31 to H-368; G-32 to H-368; L-33 to H-368; Q-34 to H-368; Y-35 to H-368; L-36 to H-368; F-37 to H-368; E-38 to H-368; N-39 to H-368; I-40 to H-368; S-41 to H-368; Q-42 to H-368; L-43 to H-368; T-44 to H-368; E-45 to H-368; K-46 to H-368; D-47 to H-368; V-48 to H-368; S-49 to H-368; T-50 to H-368; T-51 to H-368; V-52 to H-368; S-53 to H-368; R-54 to H-368; K-55 to H-368; A-56 to H-368; W-57 to H-368; G-58 to H-368; A-59 to H-368; E-60 to H-368; A-61 to H-368; V-62 to H-368; G-63 to H-368; C-64 to H-368; S-65 to H-368; I-66 to H-368; Q-67 to H-368; L-68 to H-368; T-69 to H-368; T-70 to H-368; P-71 to H-368; V-72 to H-368; N-73 to H-368; V-74 to H-368; L-75 to H-368; V-76 to H-368; I-77 to H-368; H-78 to H-368; H-79 to H-368; V-80 to H-368; P-81 to H-368; G-82 to H-368; L-83 to H-368; E-84 to H-368; C-85 to H-368; H-86 to H-368; D-87 to H-368; Q-88 to H-368; T-89 to H-368; V-90 to H-368; C-91 to H-368; S-92 to H-368; Q-93 to H-368; R-94 to H-368; L-95 to H-368; R-96 to H-368; E-97 to H-368; L-98 to H-368; Q-99 to H-368; A-100 to H-368; H-101 to H-368; H-102 to H-368; V-103 to H-368; H-104 to H-368; N-105 to H-368; N-106 to H-368; S-107 to H-368; G-108 to H-368; C-109 to H-368; D-110 to H-368; V-111 to H-368; A-112 to H-368; Y-113 to H-368; N-114 to H-368; F-115 to H-368; L-116 to H-368; V-117 to H-368; G-118 to H-368; D-119 to H-368; D-120 to H-368; G-121 to H-368; R-122 to H-368; V-123 to H-368; Y-124 to H-368; E-125 to H-368; G-126 to H-368; V-127 to H-368; G-128 to H-368; W-129 to H-368; N-130 to H-368; I-131 to H-368; Q-132 to H-368; G-133 to H-368; V-134 to H-368; H-135 to H-368; T-136 to H-368; Q-137 to H-368; G-138 to H-368; Y-139 to H-368; N-140 to H-368; N-141 to H-368; I-142 to H-368; S-143 to H-368; L-144 to H-368; G-145 to H-368; F-146 to H-368; A-147 to H-368; F-148 to H-368; F-149 to H-368; G-150 to H-368; T-151 to H-368; K-152 to H-368; K-153 to H-368; G-154 to H-368; H-155 to H-368; S-156 to H-368; P-157 to H-368; S-158 to H-368; P-159 to H-368; A-160 to H-368; A-161 to H-368; L-162 to H-368; S-163 to H-368; A-164 to H-368; M-165 to H-368; E-166 to H-368; N-167 to H-368; L-168 to H-368; I-169 to H-368; T-170 to H-368; Y-171 to H-368; A-172 to H-368; V-173 to H-368; Q-174 to H-368; K-175 to H-368; G-176 to H-368; H-177 to H-368; L-178 to H-368; S-179 to H-368; S-180 to H-368; S-181 to H-368; Y-182 to H-368; V-183 to H-368; Q-184 to H-368; P-185 to H-368; L-186 to H-368; L-187 to H-368; G-188 to H-368; K-189 to H-368; G-190 to H-368; E-191 to H-368; N-192 to H-368; C-193 to H-368; L-194 to H-368; A-195 to H-368; P-196 to H-368; R-197 to H-368; Q-198 to H-368; K-199 to H-368; T-200 to H-368; S-201 to H-368; L-202 to H-368; K-203 to H-368; K-204 to H-368; L-205 to H-368; A-206 to H-368; P-207 to H-368; A-208 to H-368; L-209 to H-368; S-210 to H-368; H-211 to H-368; G-212 to H-368; L-213 to H-368; C-214 to H-368; G-215 to H-368; E-216 to H-368; P-217 to H-368; G-218 to H-368; R-219 to H-368; P-220 to H-368; L-221 to H-368; S-222 to H-368; R-223 to H-368; M-224 to H-368; T-225 to H-368; L-226 to H-368; P-227 to H-368; A-228 to H-368; K-229 to H-368; Y-230 to H-368; G-231 to H-368; I-232 to H-368; I-233 to H-368; I-234 to H-368; H-235 to H-368; T-236 to H-368; A-237 to H-368; G-238 to H-368; R-239 to H-368; T-240 to H-368; C-241 to H-368; N-242 to H-368; I-243 to H-368; S-244 to H-368; D-245 to H-368; E-246 to H-368; C-247 to H-368; R-248 to H-368; L-249 to H-368; L-250 to H-368; V-251 to H-368; R-252 to H-368; D-253 to H-368; I-254 to H-368; Q-255 to H-368; S-256 to H-368; F-257 to H-368; Y-258 to H-368; I-259 to H-368; D-260 to H-368; R-261 to H-368; L-262 to H-368; K-263 to H-368; S-264 to H-368; C-265 to H-368; D-266 to H-368; I-267 to H-368; G-268 to H-368; Y-269 to H-368; N-270 to H-368; F-271 to H-368; L-272 to H-368; V-273 to H-368; G-274 to H-368; Q-275 to H-368; D-276 to H-368; G-277 to H-368; A-278 to H-368; I-279 to H-368; Y-280 to H-368; E-281 to H-368; G-282 to H-368; V-283 to H-368; G-284 to H-368; W-285 to H-368; N-286 to H-368; V-287 to H-368; Q-288 to H-368; G-289 to H-368; S-290 to H-368; S-291 to H-368; T-292 to H-368; P-293 to H-368; G-294 to H-368; Y-295 to H-368; D-296 to H-368; D-297 to H-368; I-298 to H-368; A-299 to H-368; L-300 to H-368; G-301 to H-368; I-302 to H-368; T-303 to H-368; F-304 to H-368; M-305 to H-368; G-306 to H-368; T-307 to H-368; F-308 to H-368; T-309 to H-368; G-310 to H-368; I-311 to H-368; P-312 to H-368; P-313 to H-368; N-314 to H-368; A-315 to H-368; A-316 to H-368; A-317 to H-368; L-318 to H-368; E-319 to H-368; A-320 to H-368; A-321 to H-368; Q-322 to H-368; D-323 to H-368; L-324 to H-368; I-325 to H-368; Q-326 to H-368; C-327 to H-368; A-328 to H-368; M-329 to H-368; V-330 to H-368; K-331 to H-368; G-332 to H-368; Y-333 to H-368; L-334 to H-368; T-335 to H-368; P-336 to H-368; N-337 to H-368; Y-338 to H-368; L-339 to H-368; L-340 to H-368; V-341 to H-368; G-342 to H-368; H-343 to H-368; S-344 to H-368; D-345 to H-368; V-346 to H-368; A-347 to H-368; R-348 to H-368; T-349 to H-368; L-350 to H-368; S-351 to H-368; P-352 to H-368; G-353 to H-368; Q-354 to H-368; A-355 to H-368; L-356 to H-368; Y-357 to H-368; N-358 to H-368; I-359 to H-368; I-360 to H-368; S-361 to H-368; T-362 to H-368; W-363 to H-368; of SEQ ID NO:4. Polynucleotides encoding these polypeptides also are provided.

In one embodiment, the present invention further provides polypeptides having one or more residues deleted from the amino terminus of the amino acid sequence of the PGRP-C polypeptide depicted in FIG. 3 (SEQ ID NO:6) or encoded by the cDNA of the deposited clone. Particularly, in one embodiment, N-terminal deletions of the PGRP-C polypeptide can be described by the general formula m to 196, where m is an integer from 2 to 196 corresponding to the position of the amino acid identified in SEQ ID NO:6 and preferably, corresponds to one of the N-terminal amino acid residues identified in the N-terminal deletions specified herein. In specific embodiments, N-terminal deletions of the PGRP-C polypeptide of the invention comprise, or alternatively, consist of, amino acid residues: S-2 to P-196; R-3 to P-196; R-4 to P-196; S-5 to P-196; M-6 to P-196; L-7 to P-196; L-8 to P-196; A-9 to P-196; W-10 to P-196; A-11 to P-196; L-12 to P-196; P-13 to P-196; S-14 to P-196; L-15 to P-196; L-16 to P-196; R-17 to P-196; L-18 to P-196; G-19 to P-196; A-20 to P-196; A-21 to P-196; Q-22 to P-196; E-23 to P-196; T-24 to P-196; E-25 to P-196; D-26 to P-196; P-27 to P-196; A-28 to P-196; C-29 to P-196; C-30 to P-196; S-31 to P-196; P-32 to P-196; I-33 to P-196; V-34 to P-196; P-35 to P-196; R-36 to P-196; N-37 to P-196; E-38 to P-196; W-39 to P-196; K-40 to P-196; A-41 to P-196; L-42 to P-196; A-43 to P-196; S-44 to P-196; E-45 to P-196; C-46 to P-196; A-47 to P-196; Q-48 to P-196; H-49 to P-196; L-50 to P-196; S-51 to P-196; L-52 to P-196; P-53 to P-196; L-54 to P-196; R-55 to P-196; Y-56 to P-196; V-57 to P-196; V-58 to P-196; V-59 to P-196; S-60 to P-196; H-61 to P-196; T-62 to P-196; A-63 to P-196; G-64 to P-196; S-65 to P-196; S-66 to P-196; C-67 to P-196; N-68 to P-196; T-69 to P-196; P-70 to P-196; A-71 to P-196; S-72 to P-196; C-73 to P-196; Q-74 to P-196; Q-75 to P-196; Q-76 to P-196; A-77 to P-196; R-78 to P-196; N-79 to P-196; V-80 to P-196; Q-81 to P-196; H-82 to P-196; Y-83 to P-196; H-84 to P-196; M-85 to P-196; K-86 to P-196; T-87 to P-196; L-88 to P-196; G-89 to P-196; W-90 to P-196; C-91 to P-196; D-92 to P-196; V-93 to P-196; G-94 to P-196; Y-95 to P-196; N-96 to P-196; F-97 to P-196; L-98 to P-196; I-99 to P-196; G-100 to P-196; E-101 to P-196; D-102 to P-196; G-103 to P-196; L-104 to P-196; V-105 to P-196; Y-106 to P-196; E-107 to P-196; G-108 to P-196; R-109 to P-196; G-110 to P-196; W-111 to P-196; N-112 to P-196; F-113 to P-196; T-114 to P-196; G-115 to P-196; A-116 to P-196; H-117 to P-196; S-118 to P-196; G-119 to P-196; H-120 to P-196; L-121 to P-196; W-122 to P-196; N-123 to P-196; P-124 to P-196; M-125 to P-196; S-126 to P-196; I-127 to P-196; G-128 to P-196; I-129 to P-196; S-130 to P-196; F-131 to P-196; M-132 to P-196; G-133 to P-196; N-134 to P-196; Y-135 to P-196; M-136 to P-196; D-137 to P-196; R-138 to P-196; V-139 to P-196; P-140 to P-196; T-141 to P-196; P-142 to P-196; Q-143 to P-196; A-144 to P-196; I-145 to P-196; R-146 to P-196; A-147 to P-196; A-148 to P-196; Q-149 to P-196; G-150 to P-196; L-151 to P-196; L-152 to P-196; A-153 to P,196; C-154 to P-196; G-155 to P-196; V-156 to P-196; A-157 to P-196; Q-158 to P-196; G-159 to P-196; A-160 to P-196; L-161 to P-196; R-162 to P-196; S-163 to P-196; N-164 to P-196; Y-165 to P-196; L-166 to P-196; L-167 to P-196; K-168 to P-196; G-169 to P-196; H-170 to P-196; R-171 to P-196; D-172 to P-196; V-173 to P-196; Q-174 to P-196; R-175 to P-196; T-176 to P-196; L-177 to P-196; S-178 to P-196; P-179 to P-196; G-180 to P-196; N-181 to P-196; Q-182 to P-196; L-183 to P-196; Y-184 to P-196; H-185 to P-196; L-186 to P-196; I-187 to P-196; Q-188 to P-196; N-189 to P-196; W-190 to P-196; P-191 to P-196; of SEQ ID NO:6. Polynucleotides encoding these polypeptides also are provided.

Further embodiments of the invention are directed to C-terminal deletions of the PGRP-K polypeptide described by the general formula 1 to n, where n is an integer from 7–242 corresponding to the position of amino acid residues identified in SEQ ID NO:2 and preferably, corresponds to one of the C-terminal amino acid residues identified in the C-terminal deletions specified herein. In specific embodiments, C terminal deletions of the PGRP-K polypeptide of the invention comprise, or alternatively, consist of, amino acid residues: M-1 to Y-242; M-1 to G-241; M-1 to I-240; M-1 to D-239; M-1 to C-238; M-1 to F-237; M-1 to N-236; M-1 to R-235; M-1 to T-234; M-1 to D-233; M-1 to M-232; M-1 to H-231; M-1 to F-230; M-1 to S-229; M-1 to Q-228; M-1 to I-227; M-1 to N-226; M-1 to R-225; M-1 to V-224; M-1 to V-223; M-1 to T-222; M-1 to Q-221; M-1 to C-220; M-1 to D-219; M-1 to T-218; M-1 to S-217; M-1 to V-216; M-1 to T-215; M-1 to C-214; M-1 to S-213; M-1 to T-212; M-1 to G-211; M-1 to A-210; M-1 to T-209; M-1 to H-208; M-1 to I-207; M-1 to I-206; M-1 to I-205; M-1 to V-204; M-1 to Y-203; M-1 to K-202; M-1 to A-201; M-1 to P-200; M-1 to L-199; M-1 to N-198; M-1 to M-197; M-1 to K-196; M-1 to P-195; M-1 to C-194; M-1 to H-193; M-1 to T-192; M-1 to E-191; M-1 to R-190; M-1 to A-189; M-1 to E-188; M-1 to W-187; M-1 to A-186; M-1 to S-185; M-1 to R-184; M-1 to K-183; M-1 to I-182; M-1 to I-181; M-1 to N-180; M-1 to P-179; M-1 to C-178; M-1 to V-177; M-1 to K-176; M-1 to R-175; M-1 to P-174; M-1 to M-173; M-1 to V-172; M-1 to P-171; M-1 to H-170; M-1 to Q-169; M-1 to P-168; M-1 to D-167; M-1 to L-166; M-1 to C-165; M-1 to T-164; M-1 to E-163; M-1 to E-162; M-1 to K-161; M-1 to L-160; M-1 to L-159; M-1 to L-158; M-1 to P-157; M-1 to Q-156; M-1 to I-155; M-1 to Y-154; M-1 to R-153; M-1 to P-152; M-1 to S-151; M-1 to L-150; M-1 to H-149; M-1 to G-148; M-1 to K-147; M-1 to Q-146; M-1 to I-145; M-1 to A-144; M-1 to Y-143; M-1 to S-142; M-1 to I-141; M-1 to L-140; M-1 to G-139; M-1 to E-138; M-1 to A-137; M-1 to A-136; M-1 to S-135; M-1 to L-134; M-1 to A-133; M-1 to A-132; M-1 to P-131; M-1 to S-130; M-1 to P-129; M-1 to S-128; M-1 to S-127; M-1 to S-126; M-1 to I-125; M-1 to K-124; M-1 to N-123; M-1 to G-122; M-1 to F-121; M-1 to F-120; M-1 to A-119; M-1 to I-118; M-1 to G-117; M-1 to L-116; M-1 to S-115; M-1 to I-114; M-1 to N-113; M-1 to N-112; M-1 to Y-111; M-1 to G-110; M-1 to Q-109; M-1 to T-108; M-1 to H-107; M-1 to L-106; M-1 to G-105; M-1 to Q-104; M-1 to I-103; M-1 to N-102; M-1 to W-101; M-1 to G-100; M-1 to V-99; M-1 to G-98; M-1 to E-97; M-1 to Y-96; M-1 to V-95; M-1 to R-94; M-1 to G-93; M-1 to D-92; M-1 to D-91; M-1 to G-90; M-1 to V-89; M-1 to L-88; M-1 to F-87; M-1 to N-86; M-1 to Y-85; M-1 to A-84; M-1 to V-83; M-1 to D-82; M-1 to C-81; M-1 to W-80; M-1 to G-79; M-1 to I-78; M-1 to T-77; M-1 to Y-76; M-1 to V-75; M-1 to S-74; M-1 to H-73; M-1 to S-72; M-1 to Q-71; M-1 to L-70; M-1 to G-69; M-1 to R-68; M-1 to L-67; M-1 to M-66; M-1 to Q-65; M-1 to S-64; M-1 to C-63; M-1 to V-62; M-1 to S-61; M-1 to Q-60; M-1 to Q-59; M-1 to Q-58; M-1 to C-57; M-1 to Q-56; M-1 to M-55; M-1 to G-54; M-1 to P-53; M-1 to L-52; M-1 to Q-51; M-1 to D-50; M-1 to T-49; M-1 to I-48; M-1 to I-47; M-1 to Y-46; M-1 to A-45; M-1 to V-44; M-1 to P-43; M-1 to L-42; M-1 to T-41; M-1 to L-40; M-1 to L-39; M-1 to A-38; M-1 to R-37; M-1 to C-36; M-1 to A-35; M-1 to L-34; M-1 to P-33; M-1 to R-32; M-1 to A-31; M-1 to G-30; M-1 to W-29; M-1 to E-28; M-1 to K-27; M-1 to R-26; M-1 to S-25; M-1 to V-24; M-1 to I-23; M-1 to T-22; M-1 to P-21; M-1 to T-20; M-1 to D-19; M-1 to W-18; M-1 to A-17; M-1 to Q-16; M-1 to L-15; M-1 to G-14; M-1 to L-13; M-1 to I-12; M-1 to F-11; M-1 to F-10; M-1 to A-9; M-1 to L-8; M-1 to L-7; SEQ ID NO:2. Polynucleotides encoding these polypeptides are also encompassed by the invention.

Further embodiments of the invention are directed to C-terminal deletions of the PGRP-W polypeptide described by the general formula 1 to n, where n is an integer from 7–367 corresponding to the position of amino acid residues identified in SEQ ID NO:4 and preferably, corresponds to one of the C-terminal amino acid residues identified in the C-terminal deletions specified herein. In specific embodiments, C terminal deletions of the PGRP-W polypeptide of the invention comprise, or alternatively, consist of, amino acid residues: M-1 to K-367; M-1 to F-366; M-1 to H-365; M-1 to P-364; M-1 to W-363; M-1 to T-362; M-1 to S-361; M-1 to I-360; M-1 to I-359; M-1 to N-358; M-1 to Y-357; M-1 to L-356; M-1 to A-355; M-1 to Q-354; M-1 to G-353; M-1 to P-352; M-1 to S-351; M-1 to L-350; M-1 to T-349; M-1 to R-348; M-1 to A-347; M-1 to V-346; M-1 to D-345; M-1 to S-344; M-1 to H-343; M-1 to G-342; M-1 to V-341; M-1 to L-340; M-1 to L-339; M-1 to Y-338; M-1 to N-337; M-1 to P-336; M-1 to T-335; M-1 to L-334; M-1 to Y-333; M-1 to G-332; M-1 to K-331; M-1 to V-330; M-1 to M-329; M-1 to A-328; M-1 to C-327; M-1 to Q-326; M-1 to I-325; M-1 to L-324; M-1 to D-323; M-1 to Q-322; M-1 to A-321; M-1 to A-320; M-1 to E-321; M-1 to L-318; M-1 to A-317; M-1 to A-316; M-1 to A-315; M-1 to N-314; M-1 to P-313; M-1 to P-312; M-1 to I-311; M-1 to G-310; M-1 to T-309; M-1 to F-308; M-1 to T-307; M-1 to G-306; M-1 to M-305; M-1 to F-304; M-1 to T-303; M-1 to I-302; M-1 to G-301; M-1 to L-300; M-1 to A-299; M-1 to I-298; M-1 to D-297; M-1 to D-296; M-1 to Y-295; M-1 to G-294; M-1 to P-293; M-1 to T-292; M-1 to S-291; M-1 to S-290; M-1 to G-289; M-1 to Q-288; M-1 to V-287; M-1 to N-286; M-1 to W-285; M-1 to G-284; M-1 to V-283; M-1 to G-282; M-1 to E-281; M-1 to Y-280; M-1 to I-279; M-1 to A-278; M-1 to G-277; M-1 to D-276; M-1 to Q-275; M-1 to G-274; M-1 to V-273; M-1 to L-272; M-1 to F-271; M-1 to N-270; M-1 to Y-269; M-1 to G-268; M-1 to I-267; M-1 to D-266; M-1 to C-265; M-1 to S-264; M-1 to K-263; M-1 to L-262; M-1 to R-261; M-1 to D-260; M-1 to I-259; M-1 to Y-258; M-1 to F-257; M-1 to S-256; M-1 to Q-255; M-1 to I-254; M-1 to D-253; M-1 to R-252; M-1 to V-251; M-1 to L-250; M-1 to L-249; M-1 to R-248; M-1 to C-247; M-1 to E-246; M-1 to D-245; M-1 to S-244; M-1 to I-243; M-1 to N-242; M-1 to C-241; M-1 to T-240; M-1 to R-239; M-1 to G-238; M-1 to A-237; M-1 to T-236; M-1 to H-235; M-1 to I-234; M-1 to I-233; M-1 to I-232; M-1 to G-231; M-1 to Y-230; M-1 to K-229; M-1 to A-228; M-1 to P-227; M-1 to L-226; M-1 to T-225; M-1 to M-224; M-1 to R-223; M-1 to S-222; M-1 to L-221; M-1 to P-220; M-1 to R-219; M-1 to G-218; M-1 to P-217; M-1 to E-216; M-1 to G-215; M-1 to C-214; M-1 to L-213; M-1 to G-212; M-1 to H-211; M-1 to S-210; M-1 to L-209; M-1 to A-208; M-1 to P-207; M-1 to A-206; M-1 to L-205; M-1 to K-204; M-1 to K-203; M-1 to L-202; M-1 to S-201; M-1 to T-200; M-1 to K-199; M-1 to Q-198; M-1 to R-197; M-1 to P-196; M-1 to A-195; M-1 to L-194; M-1 to C-193; M-1 to N-192; M-1 to E-191; M-1 to G-190; M-1 to K-189; M-1 to G-188; M-1 to L-187; M-1 to L-186; M-1 to P-185; M-1 to Q-184; M-1 to V-183; M-1 to Y-182; M-1 to S-181; M-1 to S-180; M-1 to S-179; M-1 to L-178; M-1 to H-177; M-1 to G-176; M-1 to K-175; M-1 to Q-174; M-1 to V-173; M-1 to A-172; M-1 to Y-171; M-1 to T-170; M-1 to I-169; M-1 to L-168; M-1 to N-167; M-1 to E-166; M-1 to M-165; M-1 to A-164; M-1 to S-163; M-1 to L-162; M-1 to A-161; M-1 to A-160; M-1 to P-159; M-1 to S-158; M-1 to P-157; M-1 to S-156; M-1 to H-155; M-1 to G-154; M-1 to K-153; M-1 to K-152; M-1 to T-151; M-1 to G-150; M-1 to F-149; M-1 to F-148; M-1 to A-147; M-1 to F-146; M-1 to G-145; M-1 to L-144; M-1 to S-143; M-1 to I-142; M-1 to N-141; M-1 to N-140; M-1 to Y-139; M-1 to G-138; M-1 to Q-137; M-1 to T-136; M-1 to H-135; M-1 to V-134; M-1 to G-133; M-1 to Q-132; M-1 to I-131; M-1 to N-130; M-1 to W-129; M-1 to G-128; M-1 to V-127; M-1 to G-126; M-1 to E-125; M-1 to Y-124; M-1 to V-123; M-1 to R-122; M-1 to G-121; M-1 to D-120; M-1 to D-119; M-1 to G-118; M-1 to V-117; M-1 to L-116; M-1 to F-115; M-1 to N-114; M-1 to Y-113; M-1 to A-112; M-1 to V-111; M-1 to D-110; M-1 to C-109; M-1 to G-108; M-1 to S-107; M-1 to N-106; M-1 to N-105; M-1 to H-104; M-1 to V-103; M-1 to H-102; M-1 to H-101; M-1 to A-100; M-1 to Q-99; M-1 to L-98; M-1 to E-97; M-1 to R-96; M-1 to L-95; M-1 to R-94; M-1 to Q-93; M-1 to S-92; M-1 to C-91; M-1 to V-90; M-1 to T-89; M-1 to Q-88; M-1 to D-87; M-1 to H-86; M-1 to C-85; M-1 to E-84; M-1 to L-83; M-1 to G-82; M-1 to P-81; M-1 to V-80; M-1 to H-79; M-1 to H-78; M-1 to I-77; M-1 to V-76; M-1 to L-75; M-1 to V-74; M-1 to N-73; M-1 to V-72; M-1 to P-71; M-1 to T-70; M-1 to T-69; M-1 to L-68; M-1 to Q-67; M-1 to I-66; M-1 to S-65; M-1 to C-64; M-1 to G-63; M-1 to V-62; M-1 to A-61; M-1 to E-60; M-1 to A-59; M-1 to G-58; M-1 to W-57; M-1 to A-56; M-1 to K-55; M-1 to R-54; M-1 to S-53; M-1 to V-52; M-1 to T-51; M-1 to T-50; M-1 to S-49; M-1 to V-48; M-1 to D-47; M-1 to K-46; M-1 to E-45; M-1 to T-44; M-1 to L-43; M-1 to Q-42; M-1 to S-41; M-1 to I-40; M-1 to N-39; M-1 to E-38; M-1 to F-37; M-1 to L-36; M-1 to Y-35; M-1 to Q-34; M-1 to L-33; M-1 to G-32; M-1 to E-31; M-1 to S-30; M-1 to V-29; M-1 to Q-28; M-1 to K-27; M-1 to A-26; M-1 to Q-25; M-1 to T-24; M-1 to K-23; M-1 to N-22; M-1 to W-21; M-1 to S-20; M-1 to S-19; M-1 to D-18; M-1 to G-17; M-1 to W-16; M-1 to A-15; M-1 to Q-14; M-1 to I-13; M-1 to G-12; M-1 to L-11; M-1 to A-10; M-1 to S-9; M-1 to F-8; M-1 to V-7; of SEQ ID NO:4. Polynucleotides encoding these polypeptides are also encompassed by the invention.

Further embodiments of the invention are directed to C-terminal deletions of the PGRP-C polypeptide described by the general formula 1 to n, where n is an integer from 7–196 corresponding to the position of amino acid residues identified in SEQ ID NO:6 and preferably, corresponds to one of the C-terminal amino acid residues identified in the C-terminal deletions specified herein. In specific embodiments, C terminal deletions of the PGRP-C polypeptide of the invention comprise, or alternatively, consist of, amino acid residues: M-1 to S-195; M-1 to R-194; M-1 to Y-193; M-1 to H-192; M-1 to P-191; M-1 to W-190; M-1 to N-189; M-1 to Q-188; M-1 to I-187; M-1 to L-186; M-1 to H-185; M-1 to Y-184; M-1 to L-183; M-1 to Q-182; M-1 to N-181; M-1 to G-180; M-1 to P-179; M-1 to S-178; M-1 to L-177; M-1 to T-176; M-1 to R-175; M-1 to Q-174; M-1 to V-173; M-1 to D-172; M-1 to R-171; M-1 to H-170; M-1 to G-169; M-1 to K-168; M-1 to L-167; M-1 to V-166; M-1 to Y-165; M-1 to N-164; M-1 to S-163; M-1 to R-162; M-1 to L-161; M-1 to A-160; M-1 to G-159; M-1 to Q-158; M-1 to A-157; M-1 to V-156; M-1 to G-155; M-1 to C-154; M-1 to A-153; M-1 to L-152; M-1 to L-151; M-1 to G-150; M-1 to Q-149; M-1 to A-148; M-1 to A-147; M-1 to R-146; M-1 to I-145; M-1 to A-144; M-1 to Q-143; M-1 to P-142; M-1 to T-141; M-1 to P-140; M-1 to V-139; M-1 to R-138; M-1 to D-137; M-1 to M-136; M-1 to Y-135; M-1 to N-134; M-1 to G-133; M-1 to M-132; M-1 to F-131; M-1 to S-130; M-1 to I-129; M-1 to G-128; M-1 to I-127; M-1 to S-126; M-1 to M-125; M-1 to P-124; M-1 to N-123; M-1 to W-122; M-1 to L-121; M-1 to H-120; M-1 to G-119; M-1 to S-118; M-1 to H-117; M-1 to A-116; M-1 to G-115; M-1 to T-114; M-1 to F-113; M-1 to N-112; M-1 to W-111; M-1 to G-110; M-1 to R-109; M-1 to G-108; M-1 to E-107; M-1 to Y-106; M-1 to V-105; M-1 to L-104; M-1 to G-103; M-1 to D-102; M-1 to E-101; M-1 to G-100; M-1 to I-99; M-1 to L-98; M-1 to F-97; M-1 to N-96; M-1 to Y-95; M-1 to G-94; M-1 to V-93; M-1 to D-92; M-1 to C-91; M-1 to W-90; M-1 to G-89; M-1 to L-88; M-1 to T-87; M-1 to K-86; M-1 to M-85; M-1 to H-84; M-1 to Y-83; M-1 to H-82; M-1 to Q-81; M-1 to V-80; M-1 to N-79; M-1 to R-78; M-1 to A-77; M-1 to Q-76; M-1 to Q-75; M-1 to Q-74; M-1 to C-73; M-1 to S-72; M-1 to A-71; M-1 to P-70; M-1 to T-69; M-1 to N-68; M-1 to C-67; M-1 to S-66; M-1 to S-65; M-1 to G-64; M-1 to A-63; M-1 to T-62; M-1 to H-61; M-1 to S-60; M-1 to V-59; M-1 to V-58; M-1 to V-57; M-1 to Y-56; M-1 to R-55; M-1 to L-54; M-1 to P-53; M-1 to L-52; M-1 to S-51; M-1 to L-50; M-1 to H-49; M-1 to Q-48; M-1 to A-47; M-1 to C-46; M-1 to E-45; M-1 to S-44; M-1 to A-43; M-1 to L-42; M-1 to A-41; M-1 to K-40; M-1 to W-39; M-1 to E-38; M-1 to N-37; M-1 to R-36; M-1 to P-35; M-1 to V-34; M-1 to I-33; M-1 to P-32; M-1 to S-31; M-1 to C-30; M-1 to C-29; M-1 to A-28; M-1 to P-27; M-1 to D-26; M-1 to E-25; M-1 to T-24; M-1 to E-23; M-1 to Q-22; M-1 to A-21; M-1 to A-20; M-1 to G-19; M-1 to L-18; M-1 to R-17; M-1 to L-16; M-1 to L-15; M-1 to S-14; M-1 to P-13; M-1 to L-12; M-1 to A-11; M-1 to W-10; M-1 to A-9; M-1 to L-8; M-1 to L-7; of SEQ ID NO:6. Polynucleotides encoding these polypeptides are also encompassed by the invention.

Further embodiments of the invention are directed to polypeptide fragments comprising, or alternatively, consisting of, amino acids described by the general formula m to n, where m and n are integers corresponding to any one of the amino acid residues specified above for these symbols, respectively. Polynucleotides encoding such polypeptides are also provided.

It will be recognized in the art that some amino acid sequences of the PGRP-K, the PGRP-W, and/or the PGRP-C proteins can be varied without significant effect to the structure or function of the protein. If such differences in sequence are contemplated, it should be remembered that there will be critical areas on each protein which determine activity. Thus, the invention further includes variations of the PGRP-K protein, the PGRP-W protein, and/or the PGRP-C protein which show substantial PGRP-like activity or which include regions of either the PGRP-K protein, the PGRP-W protein, and/or the PGRP-C protein such as the polypeptide portions discussed below. Such mutants include deletions, insertions, inversions, repeats, and type substitutions. For example, guidance concerning how to make phenotypically silent amino acid substitutions is provided in Bowie et al., "Deciphering the Message in Protein Sequences: Tolerance to Amino Acid Substitutions," Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues is Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

The resulting constructs can be routinely screened for activities or functions described throughout the specification and known in the art. Preferably, the resulting constructs have an increased and/or a decreased PGRP activity or function, while the remaining activities or functions are maintained. More preferably, the resulting constructs have more than one increased and/or decreased PGRP activity or function, while the remaining activities or functions are maintained.

Besides conservative amino acid substitution, variants of PGRP-K, PGRP-W, or PGRP-C include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, PGRP-K, PGRP-W, or PGRP-C polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

The resulting constructs can be routinely screened for activities or functions described throughout the specification and known in the art. Preferably, the resulting constructs have an increased and/or decreased PGRP activity or function, while the remaining activities or functions are maintained. More preferably, the resulting constructs have more than one increased and/or decreased PGRP activity or function, while the remaining activities or functions are maintained.

Additionally, more than one amino acid (e.g., 2, 3, 4, 5, 6, 7, 8, 9 and 10) can be replaced with the substituted amino acids as described above (either conservative or nonconservative). The substituted amino acids can occur in the full length, mature, or proprotein form of the PGRP-K, PGRP-W, or PGRP-C proteins, respectively, as well as the N- and C-terminal deletion mutants, having the general formula m-n, as discussed above.

A further embodiment of the invention relates to a polypeptide which comprises the amino acid sequence of a PGRP-K, PGRP-W, or PGRP-C polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polypeptide to have an amino acid sequence which comprises the amino acid sequence of a PGRP-K, PGRP-W, or PGRP-C polypeptide, which contains at least one, but not more than 10, 9, 8, 7, 6, 5, 4, 3, 2 or 1 amino acid substitutions. In specific embodiments, the number of additions, substitutions, and/or deletions in the amino acid sequence of FIG. 1 or fragments thereof (e.g., the mature form and/or other fragments described herein), is 1–5, 5–10, 5–25, 5–50, 10–50 or 50–150, conservative amino acid substitutions are preferable.

Thus, the fragment, derivative or analog of the polypeptides of FIGS. 1A–B (SEQ ID NO:2), FIGS. 2A–C (SEQ ID NO:4), and/or FIG. 3 (SEQ ID NO:6) or that are encoded by the deposited cDNAs, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the either the PGRP-K, PGRP-W, and/or PGRP-C polypeptides are fused with another compound, such as a compound to increase the half-life of the polypeptide (for example, polyethylene glycol), or (iv) one in which the additional amino acids are fused to the full length polypeptide, such as an IgG Fc fusion region peptide or leader or secretory sequence or a sequence which is employed for purification of the either the PGRP-K, PGRP-W, and/or PGRP-C polypeptides or proprotein sequences. Such fragments, derivatives and analogs are deemed to be within the scope of those skilled in the art from the teachings herein.

Of particular interest are substitutions of charged amino acids with another charged amino acid and with neutral or negatively charged amino acids. The latter results in polypeptides with reduced positive charge to improve the characteristics of either the PGRP-K, PGRP-W, and/or PGRP-C polypeptides. The prevention of aggregation is highly desirable. Aggregation of polypeptides not only results in a loss of activity but can also be problematic when preparing pharmaceutical formulations, because they can be immunogenic. (Pinckard et al., Clin. Exp. Immunol. 2:331–340 (1967); Robbins et al., Diabetes 36:838–845 (1987); Cleland et al., Crit. Rev. Therapeutic Drug Carrier Systems 10:307–377 (1993)).

The replacement of amino acids can also change the selectivity of binding to cell surface receptors. For example, Ostade et al. (Nature 361:266–268 (1993)) describes certain mutations resulting in selective binding of TNF-a to only one of the two known types of TNF receptors. Thus, the PGRP-K, PGRP-W, and/or PGRP-C proteins of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In specific embodiments, the number of substitutions, additions or deletions in the amino acid sequence of FIGS. 1A–B (SEQ ID NO:2), FIGS. 2A–C (SEQ ID NO:4), and/or FIG. 3 (SEQ ID NO:6), and/or any of the polypeptide fragments described herein (e.g., PGRP-like domain) is 100, 90, 80, 75, 70, 60, 50, 40, 35, 30, 25, 20, 15, 10, 9, 8, 7, 6, 5, 4, 3, 2, 1 or 150–100, 100–50, 50–20, 20–10, 5–10, 1–5, 1–3 or 1–2.

Amino acids in the PGRP-K, PGRP-W, and/or PGRP-C polypeptides of the present invention that are essential for function can be identified by methods known in the art, such as site-directed mutagenesis or alanine-scanning mutagenesis (Cunningham and Wells, Science 244:1081–1085 (1989)). The latter procedure introduces single alanine mutations at every residue in the molecule. The resulting mutant molecules are then tested for biological activity such as receptor binding in vitro. Sites that are critical for ligand-receptor binding can also be determined by structural analysis such as crystallization, nuclear magnetic resonance or photoaffinity labeling (Smith et al., J. Mol. Biol. 224:899–904 (1992) and de Vos et al., Science 255:306–312 (1992)).

The polypeptides of the present invention also include the polypeptides encoded by the deposited cDNAs; the polypeptide of FIGS. 1A–B (SEQ ID NO:2), the polypeptides of FIGS. 2A–C (SEQ ID NO:4), and/or the polypeptides of FIG. 3 (SEQ ID NO:6); the polypeptide sequence of any of the PGRP-like domains described herein; the polypeptide sequences of FIGS. 1A–B (SEQ ID NO:2), FIGS. 2A–C, and/or FIG. 3 (SEQ ID NO:6), minus a portion, or all of, one or more of the PGRP-like domains described supra; and polypeptides which are at least 80% identical, more preferably at least 85%, 90% or 95% identical, still more preferably at least 96%, 97%, 98% or 99% identical to the polypeptides described above, and also include portions of such polypeptides with at least 30 amino acids and more preferably at least 50 amino acids.

By a polypeptide having an amino acid sequence at least, for example, 95% "identical" to a reference amino acid sequence of either a PGRP-K, PGRP-W, and/or PGRP-C polypeptide is intended that the amino acid sequence of the polypeptide is identical to the reference sequence except that the polypeptide sequence may include up to five amino acid alterations per each 100 amino acids of the reference amino acids of either the PGRP-K, PGRP-W, and/or PGRP-C proteins. In other words, to obtain a polypeptide having an amino acid sequence at least 95% identical to one of the reference amino acid sequences, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequences shown in FIGS. 1A–B (SEQ ID NO:2), FIGS. 2A–C (SEQ ID NO:4), and/or FIG. 3 (SEQ ID NO:6), the amino acid sequence encoded by the deposited cDNA clones, respectively, or fragments thereof, can be determined conventionally using known computer programs such the MegAlign program, which is included in the suite of computer applications contained within the DNASTAR program. When using MegAlign or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty= 0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

Polynucleotides encoding polypeptides that are 80%, 85%, 90%, 95%, 96%, 97%, 98%, or 99% identical to either the PGRP-K, PGRP-W, and/or PGRP-C polypeptides described herein are also provided.

Among the especially preferred fragments of the invention are fragments characterized by structural or functional attributes of PGRP-K, PGRP-W, and/or PGRP-C. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) PGRP-K (SEQ ID NO:2), PGRP-W (SEQ ID NO:4), and/or PGRP-C (SEQ ID NO:6). Certain preferred regions are those set out in FIG. 5, FIG. 6, or FIG. 7, and include, but are not limited to, regions of the aforementioned types identified by analysis of the amino acid sequence depicted in FIGS. 1A–1B (SEQ ID NO:2), FIGS. 2A–2C (SEQ ID NO:4), and FIG. 3 (SEQ ID NO:6), such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In additional embodiments, the polynucleotides of the invention encode functional attributes of PGRP-K (SEQ ID NO:2), PGRP-W (SEQ ID NO:4), and/or PGRP-C (SEQ ID NO:6). Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of PGRP-K (SEQ ID NO:2), PGRP-W (SEQ ID NO:4), and/or PGRP-C (SEQ ID NO:6).

The data representing the structural or functional attributes of PGRP-K (SEQ ID NO:2) set forth in FIG. 5 and/or Table II, as described above, was generated using the various modules and algorithms of the DNA*STAR set on default parameters. The data representing the structural or functional attributes of PGRP-W (SEQ ID NO:4) set forth in FIG. 6 and/or Table III, as described above, was generated using the various modules and algorithms of the DNA*STAR set on default parameters. The data representing the structural or functional attributes of PGRP-C (SEQ ID NO:6) set forth in FIG. 7 and/or Table IV, as described above, was generated using the various modules and algorithms of the DNA*STAR set on default parameters. In a preferred embodiment, the data presented in columns VIII, IX, XIII, and XIV of Tables II, III, and IV can be used to determine regions of PGRP-K, PGRP-W, and PGRP-C, respectively, which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Figure 6:
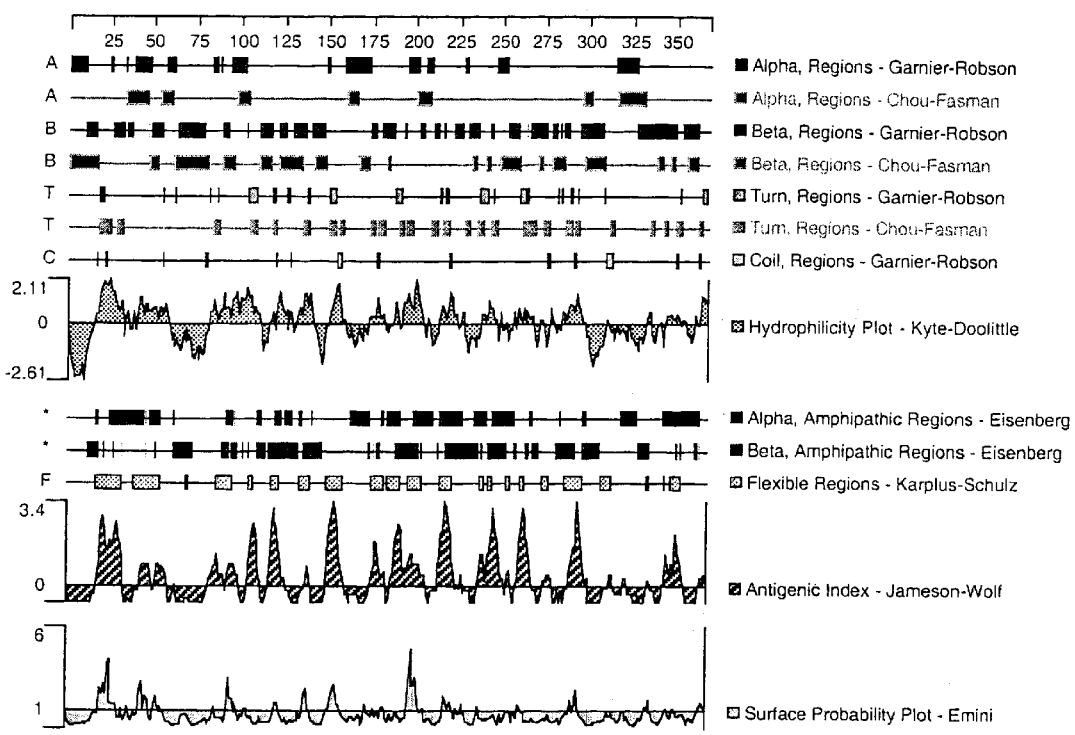
FIG. 6 and Table III show a structural analysis of the PGRP-W amino acid sequence of FIGS. 2A–C (SEQ ID NO:4), generated using the default parameters of the recited computer programs. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues: Gly-17 to Gly-32; from Ile-40 to Gly-58; from Gly-82 to Gln-99; from His-104 to Val-111; from Leu-116 to Glu-125; from Gly-150 to Pro-159; from Gln-174 to Tyr-182; from Leu-186 to Pro-207; from Val-214 to Met-225; from Thr-237 to Val-252; from Tyr-259 to Ile-268; from Gly-290 to Ala-300; from His-344 to Gln-355; and from Trp-364 to His-368 as depicted in FIGS. 2A–C (SEQ ID NO:4) correspond to the shown highly antigenic regions of the PGRP-W protein.
Figure 7:
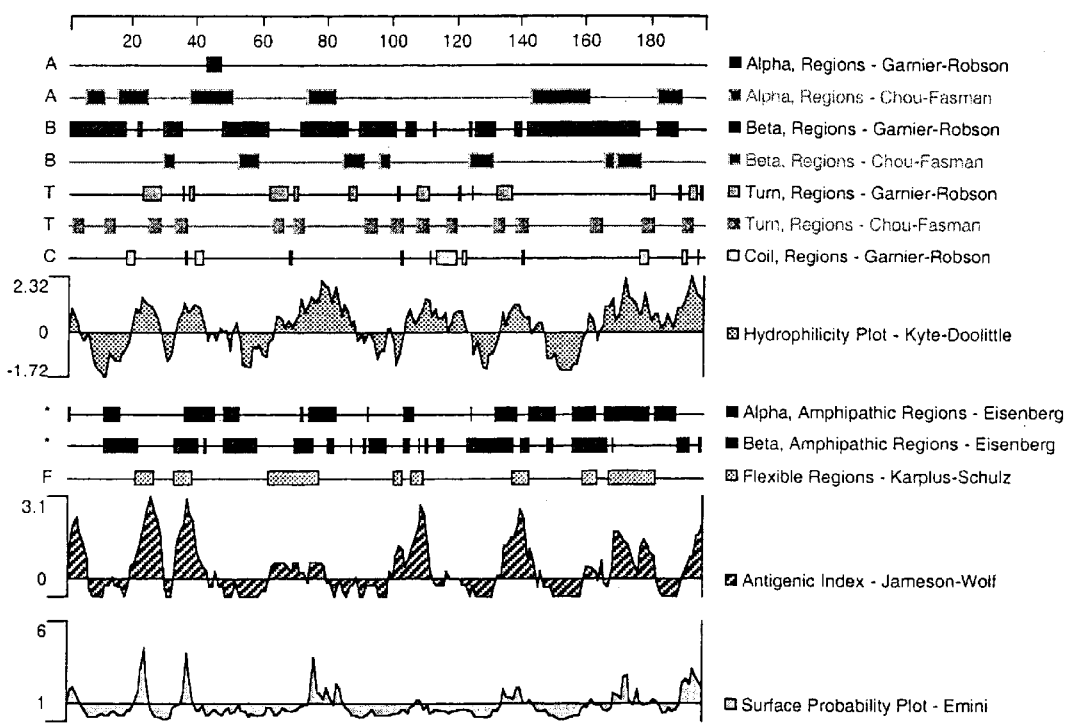
FIG. 7 and Table IV show a structural analysis of the PGRP-C amino acid sequence of FIG. 3 (SEQ ID NO:6), generated using the default parameters of the recited computer programs. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues: Met-1 to Met-6; from Ala-20 to Cys-29; from Ile-33 to Ala-43; from Ala-63 to Asn-79; from Ile-99 to Asn-112; from Gly-133 to Arg-146; from Ala-160 to Tyr-165; from Lys-168 to Asn-181; and from Trp-190 to Pro-196 as depicted in FIG. 3 (SEQ ID NO:6) correspond to the shown highly antigenic regions of the PGRP-C protein.

Certain preferred regions in these regards are set out in FIGS. 5, 6, and 7, but may, as shown in Tables II, III, and IV, be represented or identified by using tabular representations of the data presented in FIGS. 5, 6, and 7, respectively. The DNA*STAR computer algorithm used to generate FIGS. 5, 6, and 7 (set on the original default parameters) was used to present the data in FIGS. 5, 6, and 7 in a tabular format (See Tables II, III, and IV). The tabular format of the data in FIGS. 5, 6, and 7 may be used to easily determine specific boundaries of a preferred region.

The above-mentioned preferred regions set out in FIGS. 5, 6, and 7, and in Tables II, III, and IV include, but are not limited to, regions of the aforementioned types identified by analysis of the amino acid sequence set out in FIGS. 1A–1B, FIGS. 2A–2C, and FIG. 3. As set out in FIGS. 5, 6, and 7, and in Tables II, III, and IV, respectively, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

TABLE II (PGRP-K)

| Res | | I | II | III | IV | V | VI | VII | VIII | IX | X | XI | XII | XIII | XIV |
|---|---|---|---|---|---|---|---|---|---|---|---|---|---|---|---|
| Met | 1 | . | . | . | B | . | . | . | . | −0.33 | . | . | . | −0.40 | 0.44 |
| Gly | 2 | . | . | . | B | . | . | . | . | −0.23 | . | . | . | −0.40 | 0.53 |
| Thr | 3 | . | . | . | B | B | . | . | . | −0.66 | . | . | . | −0.60 | 0.43 |
| Leu | 4 | . | . | . | B | B | . | . | . | −1.08 | . | . | . | −0.60 | 0.36 |
| Pro | 5 | . | . | . | B | B | . | . | . | −1.28 | . | . | . | −0.60 | 0.30 |
| Trp | 6 | . | . | . | B | B | . | . | . | −1.38 | . | . | . | −0.60 | 0.21 |
| Leu | 7 | . | . | . | B | B | . | . | . | −1.73 | . | . | . | −0.60 | 0.22 |
| Leu | 8 | . | . | . | B | B | . | . | . | −2.31 | . | . | . | −0.60 | 0.12 |
| Ala | 9 | . | . | . | B | B | . | . | . | −2.31 | . | . | . | −0.60 | 0.08 |
| Phe | 10 | . | . | . | B | B | . | . | . | −2.44 | . | . | . | −0.60 | 0.08 |
| Phe | 11 | . | . | . | B | B | . | . | . | −2.97 | . | . | . | −0.60 | 0.10 |
| Ile | 12 | . | . | . | B | B | . | . | . | −2.16 | . | . | . | −0.60 | 0.08 |
| Leu | 13 | . | . | . | B | B | . | . | . | −1.93 | . | . | . | −0.60 | 0.16 |
| Gly | 14 | . | . | . | . | B | . | . | C | −1.63 | . | . | . | −0.40 | 0.19 |
| Leu | 15 | . | . | . | . | B | . | . | C | −0.93 | . | . | . | −0.40 | 0.28 |
| Gln | 16 | . | . | . | . | B | . | . | C | −0.54 | . | . | . | −0.40 | 0.57 |
| Ala | 17 | . | . | . | . | B | T | . | . | 0.13 | . | . | . | −0.20 | 0.84 |
| Trp | 18 | . | . | . | . | B | T | . | . | 0.63 | . | . | . | −0.05 | 1.57 |
| Asp | 19 | . | . | . | . | B | . | . | C | 0.09 | . | . | F | 0.20 | 1.31 |
| Thr | 20 | . | . | . | B | B | . | . | . | 0.04 | . | . | F | −0.45 | 0.91 |
| Pro | 21 | . | . | . | B | B | . | . | . | −0.26 | * | . | F | −0.45 | 0.64 |
| Thr | 22 | . | . | . | B | B | . | . | . | 0.44 | * | . | F | −0.15 | 0.51 |
| Ile | 23 | . | . | . | B | B | . | . | . | 0.78 | . | . | . | −0.30 | 0.70 |
| Val | 24 | . | . | . | B | B | . | . | . | 0.78 | . | . | . | 0.30 | 0.90 |
| Ser | 25 | . | . | A | B | . | . | . | . | 0.80 | . | . | F | 0.90 | 1.08 |
| Arg | 26 | . | . | A | B | . | . | . | . | 0.67 | . | . | F | 0.60 | 1.63 |
| Lys | 27 | . | . | A | B | . | . | . | . | 0.39 | . | * | F | 0.90 | 2.17 |
| Glu | 28 | . | . | A | . | . | T | . | . | 1.39 | . | * | F | 1.30 | 1.63 |
| Trp | 29 | . | . | A | . | . | T | . | . | 2.03 | . | * | . | 1.15 | 1.63 |
| Gly | 30 | . | . | A | . | . | T | . | . | 1.52 | . | * | . | 1.15 | 1.26 |
| Ala | 31 | . | . | A | . | . | T | . | . | 0.82 | . | * | F | 0.85 | 0.60 |
| Arg | 32 | . | . | A | . | . | . | . | C | 0.11 | . | . | F | −0.25 | 0.58 |
| Pro | 33 | . | . | A | . | . | . | . | C | 0.22 | * | * | . | −0.10 | 0.31 |
| Leu | 34 | . | . | A | . | . | T | . | . | −0.08 | * | . | . | 0.70 | 0.61 |
| Ala | 35 | . | . | A | B | . | . | . | . | −0.54 | . | * | . | 0.30 | 0.31 |
| Cys | 36 | . | . | A | B | . | . | . | . | −0.77 | . | * | . | −0.30 | 0.17 |
| Arg | 37 | . | . | A | B | B | . | . | . | −1.19 | * | * | . | −0.60 | 0.17 |
| Ala | 38 | . | . | A | B | B | . | . | . | −1.79 | * | * | . | −0.60 | 0.24 |
| Leu | 39 | . | . | A | B | B | . | . | . | −1.19 | * | * | . | −0.60 | 0.37 |
| Leu | 40 | . | . | A | B | B | . | . | . | −1.46 | * | * | . | −0.60 | 0.29 |
| Thr | 41 | . | . | A | B | B | . | . | . | −1.38 | * | * | . | −0.60 | 0.21 |

TABLE II-continued (PGRP-K)

| Res | I | II | III | IV | V | VI | VII | VIII | IX | X | XI | XII | XIII | XIV |
|---|---|---|---|---|---|---|---|---|---|---|---|---|---|---|
| Leu | 42 | . | A | B | B | . | . | . | −1.73 | * | * | . | −0.60 | 0.26 |
| Pro | 43 | . | A | B | B | . | . | . | −2.03 | . | . | . | −0.60 | 0.50 |
| Val | 44 | . | . | B | B | . | . | . | −2.11 | . | . | . | −0.60 | 0.24 |
| Ala | 45 | . | . | B | B | . | . | . | −1.61 | . | . | . | −0.60 | 0.20 |
| Tyr | 46 | . | . | B | B | . | . | . | −1.30 | . | . | . | −0.60 | 0.19 |
| Ile | 47 | . | . | B | B | . | . | . | −0.49 | * | . | . | −0.60 | 0.43 |
| Ile | 48 | . | . | B | B | . | . | . | −1.09 | * | . | . | −0.60 | 0.74 |
| Thr | 49 | . | . | B | B | . | . | . | −0.44 | * | . | . | −0.60 | 0.39 |
| Asp | 50 | . | . | B | B | . | . | . | −0.20 | . | . | F | −0.11 | 0.86 |
| Gln | 51 | . | . | . | B | . | . | . | −0.56 | . | . | F | 0.28 | 1.21 |
| Leu | 52 | . | . | . | . | . | T | C | 0.33 | . | . | F | 0.57 | 0.83 |
| Pro | 53 | . | . | . | . | T | T | . | 0.56 | . | . | F | 1.41 | 0.86 |
| Gly | 54 | . | . | . | . | T | T | . | 0.87 | . | . | . | 0.40 | 0.27 |
| Met | 55 | . | . | . | . | T | T | . | 0.87 | . | . | . | 0.36 | 0.56 |
| Gln | 56 | . | . | B | B | . | . | . | 0.87 | . | . | . | −0.18 | 0.63 |
| Cys | 57 | . | . | B | B | . | . | . | 1.38 | . | . | F | 0.08 | 1.09 |
| Gln | 58 | . | . | B | B | . | . | . | 0.73 | . | . | F | 0.04 | 1.48 |
| Gln | 59 | . | . | B | B | . | . | . | 0.41 | . | . | F | −0.15 | 0.63 |
| Gln | 60 | . | . | B | B | . | . | . | 0.71 | . | . | F | −0.15 | 0.63 |
| Ser | 61 | . | . | B | B | . | . | . | 0.71 | . | . | F | −0.15 | 0.49 |
| Val | 62 | . | . | B | B | . | . | . | 0.78 | . | . | F | −0.15 | 0.49 |
| Cys | 63 | . | . | B | B | . | . | . | −0.03 | * | . | . | −0.60 | 0.28 |
| Ser | 64 | . | . | B | B | . | . | . | 0.08 | * | * | . | −0.60 | 0.17 |
| Gln | 65 | . | . | B | B | . | . | . | −0.27 | * | . | . | −0.30 | 0.46 |
| Met | 66 | . | . | B | B | . | . | . | −0.78 | * | . | . | −0.30 | 0.84 |
| Leu | 67 | . | . | B | B | . | . | . | 0.08 | * | . | . | −0.30 | 0.52 |
| Arg | 68 | . | . | B | B | . | . | . | 0.44 | * | . | . | −0.30 | 0.52 |
| Gly | 69 | . | . | B | . | . | . | . | 0.71 | * | . | F | 0.05 | 0.70 |
| Leu | 70 | . | . | . | . | . | . | C | 0.41 | * | . | F | 0.40 | 1.16 |
| Gln | 71 | . | . | B | . | . | T | C | 0.16 | * | . | F | 1.05 | 0.79 |
| Ser | 72 | . | . | . | . | . | T | C | 0.72 | . | . | . | 0.00 | 0.59 |
| His | 73 | . | . | B | . | . | T | . | 0.30 | . | . | . | −0.05 | 1.13 |
| Ser | 74 | . | . | B | . | . | T | . | −0.24 | . | . | . | −0.20 | 0.94 |
| Val | 75 | . | . | B | B | . | . | . | 0.22 | . | . | . | −0.60 | 0.49 |
| Tyr | 76 | . | . | B | B | . | . | . | −0.07 | . | . | . | −0.60 | 0.36 |
| Thr | 77 | . | . | B | B | . | . | . | −0.43 | . | . | . | −0.60 | 0.28 |
| Ile | 78 | . | . | B | B | . | . | . | −0.40 | . | . | . | −0.60 | 0.20 |
| Gly | 79 | . | . | B | B | . | . | . | −0.96 | . | . | . | −0.60 | 0.22 |
| Trp | 80 | . | . | B | B | . | . | . | −0.69 | . | . | . | −0.60 | 0.11 |
| Cys | 81 | . | . | B | B | . | . | . | −0.69 | . | . | . | −0.60 | 0.16 |
| Asp | 82 | . | . | B | B | . | . | . | −0.38 | . | * | . | −0.60 | 0.25 |
| Val | 83 | . | . | B | B | . | . | . | −0.19 | * | . | . | −0.60 | 0.39 |
| Ala | 84 | . | . | B | B | . | . | . | −0.66 | * | * | . | −0.60 | 0.63 |
| Tyr | 85 | . | . | B | B | . | . | . | −1.22 | * | * | . | −0.60 | 0.31 |
| Asn | 86 | . | . | B | B | . | . | . | −0.90 | . | * | . | −0.60 | 0.31 |
| Phe | 87 | . | . | B | B | . | . | . | −0.90 | . | * | . | −0.29 | 0.30 |
| Leu | 88 | . | . | B | B | . | . | . | −0.04 | . | . | . | 0.02 | 0.32 |
| Val | 89 | . | . | B | B | . | . | . | 0.20 | . | * | . | 1.23 | 0.34 |
| Gly | 90 | . | . | . | . | T | T | . | 0.56 | . | * | F | 2.49 | 0.38 |
| Asp | 91 | . | . | . | . | T | T | . | −0.30 | . | * | F | 3.10 | 0.91 |
| Asp | 92 | . | . | . | . | . | T | C | 0.16 | . | * | F | 2.59 | 0.91 |
| Gly | 93 | . | . | . | . | . | T | C | 0.97 | * | * | F | 2.43 | 1.44 |
| Arg | 94 | . | . | B | . | . | . | . | 1.48 | * | * | F | 1.72 | 1.49 |
| Val | 95 | . | . | B | . | . | . | . | 0.97 | * | * | F | 1.26 | 0.89 |
| Tyr | 96 | . | . | B | . | . | . | . | 0.62 | * | * | . | 0.50 | 0.66 |
| Glu | 97 | . | . | B | . | . | . | . | 0.33 | . | * | . | 0.50 | 0.34 |
| Gly | 98 | . | . | . | . | T | . | . | 0.68 | * | * | . | 0.00 | 0.48 |
| Val | 99 | . | . | . | . | T | . | . | −0.32 | * | * | . | 0.00 | 0.49 |
| Gly | 100 | . | . | . | . | T | . | . | 0.53 | * | * | . | 0.00 | 0.20 |
| Trp | 101 | . | . | . | . | . | . | C | 0.43 | * | * | . | −0.20 | 0.35 |
| Asn | 102 | . | . | B | . | . | . | . | −0.38 | * | * | . | −0.40 | 0.46 |
| Ile | 103 | . | . | B | . | . | . | . | −0.07 | . | * | . | −0.40 | 0.38 |
| Gln | 104 | . | . | B | . | . | . | . | 0.48 | . | * | . | −0.40 | 0.50 |
| Gly | 105 | . | . | B | . | . | . | . | 0.82 | * | * | F | −0.25 | 0.45 |
| Leu | 106 | . | . | B | . | . | . | . | 0.77 | * | * | F | −0.10 | 1.10 |
| His | 107 | . | . | B | . | . | . | . | 0.52 | * | . | F | 0.05 | 0.63 |
| Thr | 108 | . | . | . | . | . | T | C | 1.41 | * | . | F | 0.15 | 1.00 |
| Gln | 109 | . | . | . | . | . | T | . | 1.41 | . | * | F | 0.50 | 1.94 |
| Gly | 110 | . | . | . | . | T | T | . | 0.87 | . | * | F | 0.80 | 2.30 |
| Tyr | 111 | . | . | . | . | T | T | . | 1.38 | . | * | F | 0.50 | 1.12 |
| Asn | 112 | . | . | . | . | . | . | C | 0.60 | . | * | F | −0.05 | 0.86 |
| Asn | 113 | . | . | B | B | . | . | . | 0.57 | * | * | . | −0.60 | 0.72 |
| Ile | 114 | . | . | B | B | . | . | . | −0.32 | * | * | . | −0.60 | 0.45 |

TABLE II-continued (PGRP-K)

| Res | I | II | III | IV | V | VI | VII | VIII | IX | X | XI | XII | XIII | XIV |
|---|---|---|---|---|---|---|---|---|---|---|---|---|---|---|
| Ser | 115 | . | . | B | B | . | . | . | −0.57 | . | * | . | −0.60 | 0.20 |
| Leu | 116 | . | . | B | B | . | . | . | −1.02 | . | * | . | −0.60 | 0.12 |
| Gly | 117 | . | . | B | B | . | . | . | −1.72 | . | * | . | −0.60 | 0.15 |
| Ile | 118 | . | . | B | B | . | . | . | −2.07 | . | * | . | 0.60 | 0.10 |
| Ala | 119 | . | . | B | B | . | . | . | −1.18 | . | * | . | 0.60 | 0.12 |
| Phe | 120 | . | . | B | B | . | . | . | −0.83 | . | * | . | −0.60 | 0.19 |
| Phe | 121 | . | . | B | . | . | T | . | −0.91 | . | * | . | −0.20 | 0.55 |
| Gly | 122 | . | . | B | . | . | T | . | −0.87 | * | . | F | 0.19 | 0.38 |
| Asn | 123 | . | . | . | . | T | T | . | −0.28 | * | . | F | 0.83 | 0.59 |
| Lys | 124 | . | . | . | . | T | T | . | 0.01 | . | . | F | 1.37 | 0.92 |
| Ile | 125 | . | . | . | . | T | . | . | 0.50 | * | . | F | 2.16 | 1.24 |
| Ser | 126 | . | . | . | . | T | . | . | 0.90 | * | * | F | 2.40 | 1.20 |
| Ser | 127 | . | . | . | . | . | . | C | 1.03 | * | . | F | 1.81 | 0.80 |
| Ser | 128 | . | . | . | . | . | T | C | 0.44 | * | . | F | 1.32 | 1.77 |
| Pro | 129 | . | . | . | . | . | T | C | −0.19 | . | * | F | 1.68 | 1.33 |
| Ser | 130 | . | . | . | . | . | T | C | −0.11 | . | . | F | 0.84 | 1.00 |
| Pro | 131 | . | . | . | . | . | T | C | −0.11 | . | . | F | 0.45 | 0.62 |
| Ala | 132 | . | A | B | . | . | . | . | −0.40 | . | . | . | −0.30 | 0.54 |
| Ala | 133 | . | A | B | . | . | . | . | −0.69 | . | . | . | −0.30 | 0.40 |
| Leu | 134 | . | A | B | . | . | . | . | −0.48 | . | . | . | −0.60 | 0.26 |
| Ser | 135 | . | A | B | . | . | . | . | −0.52 | . | . | . | −0.30 | 0.45 |
| Ala | 136 | . | A | B | . | . | . | . | −1.12 | . | . | . | −0.30 | 0.44 |
| Ala | 137 | . | A | B | . | . | . | . | −1.42 | * | . | . | −0.30 | 0.44 |
| Glu | 138 | A | A | B | . | . | . | . | −1.13 | * | . | . | −0.30 | 0.23 |
| Gly | 139 | . | . | B | . | . | . | . | −0.57 | * | . | . | −0.10 | 0.31 |
| Leu | 140 | . | . | B | . | . | . | . | −0.86 | * | . | . | −0.40 | 0.48 |
| Ile | 141 | . | . | B | . | . | . | . | −1.16 | * | * | . | −0.40 | 0.28 |
| Ser | 142 | . | . | B | . | . | . | . | −0.57 | * | * | . | −0.40 | 0.20 |
| Tyr | 143 | . | . | B | . | . | . | . | −0.52 | * | . | . | −0.40 | 0.41 |
| Ala | 144 | . | . | B | . | . | . | . | −0.52 | * | . | . | −0.25 | 1.18 |
| Ile | 145 | . | . | B | . | . | . | . | 0.26 | * | . | . | −0.10 | 0.87 |
| Gln | 146 | . | . | B | . | . | T | . | 0.33 | * | * | . | 0.36 | 0.76 |
| Lys | 147 | . | . | . | . | T | T | . | 0.33 | . | . | F | 1.17 | 0.62 |
| Gly | 148 | . | . | . | . | T | T | . | 0.37 | * | * | F | 1.58 | 1.18 |
| His | 149 | . | . | . | . | T | T | . | 1.07 | * | * | F | 2.44 | 1.05 |
| Leu | 150 | . | . | . | . | . | . | C | 1.71 | * | * | F | 2.60 | 1.03 |
| Ser | 151 | . | . | . | . | . | T | C | 0.82 | * | * | F | 1.64 | 1.64 |
| Pro | 152 | . | . | . | . | . | T | . | 0.78 | * | * | F | 1.13 | 0.84 |
| Arg | 153 | . | . | . | . | . | T | . | 0.91 | * | * | . | 1.17 | 1.77 |
| Tyr | 154 | . | . | B | . | . | T | . | 0.13 | * | * | . | 0.51 | 2.04 |
| Ile | 155 | . | . | B | . | . | . | . | 0.13 | * | . | . | 0.05 | 1.09 |
| Gln | 156 | . | A | B | . | . | . | . | −0.38 | * | . | . | −0.60 | 0.46 |
| Pro | 157 | . | A | B | . | . | . | . | −0.12 | * | . | . | −0.60 | 0.24 |
| Leu | 158 | . | A | B | . | . | . | . | −0.23 | * | . | . | −0.60 | 0.69 |
| Leu | 159 | . | A | B | . | . | . | . | 0.01 | . | . | . | 0.30 | 0.69 |
| Leu | 160 | . | A | B | . | . | . | . | 0.59 | . | . | F | 0.75 | 0.77 |
| Lys | 161 | . | A | B | . | . | . | . | −0.08 | . | . | F | 0.60 | 1.35 |
| Glu | 162 | . | A | B | . | . | . | . | −0.68 | . | * | F | 0.75 | 0.88 |
| Glu | 163 | . | A | B | . | . | . | . | 0.13 | . | * | F | 0.75 | 0.88 |
| Thr | 164 | . | A | . | . | T | . | . | 0.73 | . | * | F | 1.15 | 0.73 |
| Cys | 165 | . | A | . | . | T | . | . | 1.54 | . | * | F | 1.15 | 0.65 |
| Leu | 166 | . | A | . | . | T | . | . | 1.47 | . | * | F | 0.85 | 0.65 |
| Asp | 167 | . | . | . | . | . | T | C | 1.26 | . | * | F | 0.45 | 0.62 |
| Pro | 168 | . | . | . | . | T | T | . | 0.40 | . | * | F | 0.80 | 1.78 |
| Gln | 169 | . | . | . | . | T | T | . | 0.11 | . | * | F | 0.80 | 1.60 |
| His | 170 | . | . | . | . | . | T | C | 0.57 | * | * | . | 0.30 | 0.95 |
| Pro | 171 | . | . | B | . | . | . | . | 1.49 | * | . | . | −0.40 | 0.95 |
| Val | 172 | . | . | B | . | . | . | . | 1.53 | . | . | . | 0.05 | 1.07 |
| Met | 173 | . | . | B | . | . | . | . | 0.89 | . | . | . | 0.65 | 1.58 |
| Pro | 174 | . | . | B | . | . | . | . | 0.22 | . | . | . | 0.50 | 0.76 |
| Arg | 175 | . | . | . | T | . | . | . | 0.04 | . | . | F | 1.05 | 0.55 |
| Lys | 176 | . | . | B | . | . | . | . | 0.26 | * | * | F | 0.65 | 0.85 |
| Val | 177 | . | . | B | . | . | . | . | 0.22 | * | . | . | 0.97 | 0.89 |
| Cys | 178 | . | . | B | . | . | T | . | −0.07 | * | . | . | 1.04 | 0.32 |
| Pro | 179 | . | . | B | . | . | T | . | 0.19 | * | . | . | 0.31 | 0.11 |
| Asn | 180 | . | . | B | . | . | T | . | 0.19 | * | . | . | 0.48 | 0.30 |
| Ile | 181 | . | . | B | . | . | T | . | −0.16 | * | * | . | 1.70 | 1.10 |
| Ile | 182 | . | . | B | . | . | . | . | 0.11 | * | . | . | 1.18 | 0.95 |
| Lys | 183 | . | A | B | . | . | . | . | 0.49 | * | . | . | 0.81 | 0.60 |
| Arg | 184 | . | A | B | . | . | . | . | 0.70 | * | . | F | 0.19 | 0.90 |
| Ser | 185 | . | A | . | . | . | . | C | 0.11 | * | * | . | 1.12 | 2.21 |
| Ala | 186 | . | A | . | . | . | . | C | 1.11 | * | * | . | 0.95 | 1.12 |
| Trp | 187 | . | A | . | . | . | . | C | 2.00 | * | * | . | 0.95 | 1.12 |

TABLE II-continued (PGRP-K)

| Res | | Pos. | | | | | | | | | | | | |
|---|---|---|---|---|---|---|---|---|---|---|---|---|---|---|
| | | I | II | III | IV | V | VI | VII | VIII | IX | X | XI | XII | XIII | XIV |
| Glu | 188 | . | A | . | . | . | . | . | C | 1.64 | * | * | . | 0.95 | 1.45 |
| Ala | 189 | A | A | . | . | . | . | . | . | 1.50 | . | * | F | 0.90 | 2.06 |
| Arg | 190 | . | A | . | . | . | T | . | . | 1.13 | . | * | F | 1.30 | 2.67 |
| Glu | 191 | . | A | . | . | . | T | . | . | 1.51 | . | * | F | 1.15 | 0.83 |
| Thr | 192 | . | A | . | . | . | T | . | . | 1.84 | . | * | F | 1.30 | 1.27 |
| His | 193 | . | A | . | . | . | T | . | . | 1.24 | . | * | F | 1.30 | 1.29 |
| Cys | 194 | . | . | . | . | . | . | T | C | 1.83 | . | * | . | 0.90 | 0.74 |
| Pro | 195 | . | . | . | . | . | T | T | . | 0.91 | . | * | . | 0.50 | 0.82 |
| Lys | 196 | . | . | . | . | . | T | T | . | 0.70 | . | * | . | 0.50 | 0.50 |
| Met | 197 | . | . | . | . | . | T | T | . | 0.42 | . | * | . | 0.65 | 1.44 |
| Asn | 198 | . | . | . | . | . | . | . | C | 0.50 | . | * | . | 0.10 | 0.94 |
| Leu | 199 | . | . | . | B | . | . | . | . | 0.92 | . | * | . | 0.50 | 0.94 |
| Pro | 200 | . | . | . | B | . | . | . | . | 0.28 | . | * | . | 0.05 | 1.49 |
| Ala | 201 | . | . | . | . | B | T | . | . | −0.66 | * | * | . | −0.20 | 0.69 |
| Lys | 202 | . | . | . | B | B | . | . | . | −0.94 | * | * | . | −0.60 | 0.58 |
| Tyr | 203 | . | . | . | B | B | . | . | . | −1.83 | . | * | . | −0.60 | 0.26 |
| Val | 204 | . | . | . | B | B | . | . | . | −1.06 | . | * | . | −0.60 | 0.18 |
| Ile | 205 | . | . | . | B | B | . | . | . | −1.16 | . | . | . | −0.60 | 0.12 |
| Ile | 206 | . | . | . | B | B | . | . | . | −1.16 | . | . | . | −0.60 | 0.12 |
| Ile | 207 | . | . | . | B | B | . | . | . | −1.54 | . | . | . | −0.60 | 0.16 |
| His | 208 | . | . | . | B | B | . | . | . | −1.61 | . | . | . | −0.60 | 0.22 |
| Thr | 209 | . | . | . | B | B | . | . | . | −1.06 | . | . | . | −0.60 | 0.46 |
| Ala | 210 | . | . | . | . | B | T | . | . | −0.83 | . | . | F | −0.05 | 0.87 |
| Gly | 211 | . | . | . | . | . | T | T | . | −0.26 | . | . | F | 0.65 | 0.34 |
| Thr | 212 | . | . | . | . | . | T | T | . | −0.22 | . | . | F | 0.65 | 0.34 |
| Ser | 213 | . | . | . | . | . | T | T | . | −0.49 | . | . | F | 0.35 | 0.25 |
| Cys | 214 | . | . | . | B | . | . | T | . | −0.49 | . | . | . | 0.10 | 0.34 |
| Thr | 215 | . | . | . | B | . | . | . | . | 0.10 | . | * | . | −0.40 | 0.34 |
| Val | 216 | . | . | . | B | . | . | . | . | −0.22 | . | * | F | 0.82 | 0.43 |
| Ser | 217 | . | . | . | B | . | . | T | . | 0.09 | . | * | F | 0.59 | 0.43 |
| Thr | 218 | . | . | . | B | . | . | T | . | 0.08 | . | * | F | 1.36 | 0.51 |
| Asp | 219 | . | . | . | . | . | T | T | . | −0.11 | . | * | F | 1.93 | 0.99 |
| Cys | 220 | . | . | . | B | . | . | T | . | −0.66 | * | * | F | 1.70 | 0.55 |
| Gln | 221 | . | . | . | B | B | . | . | . | 0.31 | * | * | F | 0.53 | 0.28 |
| Thr | 222 | . | . | . | B | B | . | . | . | 0.61 | * | * | . | 0.81 | 0.33 |
| Val | 223 | . | . | . | B | B | . | . | . | 0.03 | * | . | . | 0.04 | 0.99 |
| Val | 224 | . | . | . | B | B | . | . | . | 0.03 | * | . | . | −0.13 | 0.40 |
| Arg | 225 | . | . | . | B | B | . | . | . | 0.40 | * | . | . | −0.30 | 0.48 |
| Asn | 226 | . | . | . | B | B | . | . | . | −0.30 | * | . | . | −0.30 | 0.87 |
| Ile | 227 | . | . | . | B | B | . | . | . | −0.02 | * | . | F | 0.00 | 1.02 |
| Gln | 228 | . | . | . | B | B | . | . | . | 0.23 | * | . | F | −0.15 | 0.71 |
| Ser | 229 | . | . | . | B | B | . | . | . | 1.09 | * | * | . | −0.60 | 0.43 |
| Phe | 230 | . | . | . | B | B | . | . | . | 0.67 | * | * | . | 0.13 | 1.04 |
| His | 231 | . | . | . | B | B | . | . | . | 0.78 | * | * | . | 0.26 | 0.86 |
| Met | 232 | . | . | . | B | B | . | . | . | 1.67 | * | . | . | 1.29 | 1.26 |
| Asp | 233 | . | . | . | . | . | T | T | . | 0.97 | * | * | . | 2.37 | 2.34 |
| Thr | 234 | . | . | . | . | . | T | T | . | 0.60 | * | * | F | 2.80 | 1.49 |
| Arg | 235 | . | . | . | . | . | T | T | . | 1.30 | * | * | F | 2.37 | 0.81 |
| Asn | 236 | . | . | . | . | . | T | T | . | 0.44 | * | * | . | 2.24 | 0.81 |
| Phe | 237 | . | . | . | . | . | T | . | . | 0.70 | * | * | . | 1.46 | 0.39 |
| Cys | 238 | . | . | . | . | . | T | . | . | 0.46 | * | * | . | 1.18 | 0.20 |
| Asp | 239 | . | . | . | . | . | T | T | . | 0.77 | * | * | . | 0.20 | 0.19 |
| Ile | 240 | . | . | . | . | . | T | T | . | 0.27 | * | * | . | 0.20 | 0.39 |
| Gly | 241 | . | . | . | . | . | T | T | . | −0.12 | * | . | . | 0.50 | 0.92 |
| Tyr | 242 | . | . | . | B | . | . | T | . | 0.19 | * | . | . | 0.10 | 0.71 |
| Gln | 243 | . | . | . | B | . | . | . | . | 0.47 | . | * | . | −0.25 | 1.29 |

TABLE III (PGRP-W)

| Res | | Pos. | | | | | | | | | | | | |
|---|---|---|---|---|---|---|---|---|---|---|---|---|---|---|
| | | I | II | III | IV | V | VI | VII | VIII | IX | X | XI | XII | XIII | XIV |
| Met | 1 | . | . | . | . | B | . | . | . | −1.38 | . | . | . | −0.60 | 0.27 |
| Leu | 2 | A | . | . | . | B | . | . | . | −1.80 | . | . | . | −0.60 | 0.17 |
| Leu | 3 | A | . | . | . | B | . | . | . | −2.27 | . | . | . | −0.60 | 0.11 |
| Trp | 4 | A | . | . | . | B | . | . | . | −2.58 | . | . | . | −0.60 | 0.08 |
| Leu | 5 | A | . | . | . | B | . | . | . | −2.49 | . | . | . | −0.60 | 0.09 |

TABLE III-continued (PGRP-W)

| Res | | | | | | | | Pos. | | | | | | |
|---|---|---|---|---|---|---|---|---|---|---|---|---|---|---|
| | I | II | III | IV | V | VI | VII | VIII | IX | X | XI | XII | XIII | XIV |
| Leu | 6 | A | . | . | B | . | . | . | −2.48 | . | . | . | −0.60 | 0.14 |
| Val | 7 | A | . | . | B | . | . | . | −2.48 | . | . | . | −0.60 | 0.14 |
| Phe | 8 | A | . | . | B | . | . | . | −2.01 | . | . | . | −0.60 | 0.14 |
| Ser | 9 | A | . | . | B | . | . | . | −2.61 | . | . | . | −0.60 | 0.16 |
| Ala | 10 | A | . | B | B | . | . | . | −1.80 | . | . | . | −0.60 | 0.15 |
| Leu | 11 | . | . | B | B | . | . | . | −1.58 | . | . | . | −0.60 | 0.31 |
| Gly | 12 | . | . | B | B | . | . | . | −1.01 | . | . | . | −0.60 | 0.23 |
| Ile | 13 | . | . | B | B | . | . | . | −0.66 | . | * | . | −0.60 | 0.24 |
| Gln | 14 | . | . | B | B | . | . | . | −0.36 | . | * | . | −0.60 | 0.29 |
| Ala | 15 | . | . | B | B | . | . | . | −0.07 | . | * | . | −0.30 | 0.49 |
| Trp | 16 | . | . | B | B | . | . | . | 0.44 | . | * | . | −0.30 | 0.93 |
| Gly | 17 | . | . | . | B | . | . | C | 0.50 | * | * | F | 0.33 | 0.72 |
| Asp | 18 | . | . | . | . | T | T | . | 1.39 | * | * | F | 0.91 | 0.75 |
| Ser | 19 | . | . | . | . | . | T | C | 1.43 | . | . | F | 1.14 | 1.15 |
| Ser | 20 | . | . | . | . | T | T | . | 1.71 | . | . | F | 2.52 | 2.32 |
| Trp | 21 | . | . | . | . | T | T | . | 2.00 | . | . | F | 2.80 | 2.01 |
| Asn | 22 | . | . | . | . | . | T | C | 1.76 | . | * | F | 2.32 | 2.60 |
| Lys | 23 | . | . | . | . | . | T | C | 1.80 | . | . | F | 1.44 | 1.96 |
| Thr | 24 | A | . | . | . | . | T | . | 2.10 | . | . | F | 1.56 | 3.72 |
| Gln | 25 | A | . | . | . | . | T | . | 1.54 | * | . | F | 1.84 | 4.01 |
| Ala | 26 | . | . | B | . | . | . | . | 1.53 | * | . | F | 1.62 | 1.49 |
| Lys | 27 | . | . | B | . | . | . | . | 1.53 | * | . | F | 1.58 | 1.38 |
| Gln | 28 | . | . | B | . | . | . | . | 1.14 | * | * | F | 2.14 | 1.38 |
| Val | 29 | . | . | B | . | . | T | . | 0.64 | * | . | F | 2.60 | 1.35 |
| Ser | 30 | . | . | B | . | . | T | . | 0.64 | * | . | F | 1.89 | 0.56 |
| Glu | 31 | . | . | B | . | . | T | . | 0.99 | * | . | F | 1.63 | 0.56 |
| Gly | 32 | . | . | B | . | . | T | . | 0.13 | * | . | F | 0.92 | 1.18 |
| Leu | 33 | . | A | B | . | . | . | . | −0.57 | * | * | . | −0.04 | 0.73 |
| Gln | 34 | A | A | . | . | . | . | . | 0.29 | * | . | . | −0.60 | 0.36 |
| Tyr | 35 | . | A | B | . | . | . | . | 0.59 | * | . | . | −0.60 | 0.63 |
| Leu | 36 | . | A | B | . | . | . | . | −0.30 | * | . | . | −0.45 | 1.24 |
| Phe | 37 | . | A | B | . | . | . | . | −0.26 | * | . | . | −0.60 | 0.50 |
| Glu | 38 | A | A | . | . | . | . | . | 0.56 | * | . | . | −0.60 | 0.43 |
| Asn | 39 | A | A | . | . | . | . | . | −0.26 | * | . | F | −0.15 | 0.90 |
| Ile | 40 | A | A | . | . | . | . | . | −0.32 | * | . | F | −0.15 | 0.86 |
| Ser | 41 | A | A | . | . | . | . | . | 0.49 | * | . | F | −0.15 | 0.71 |
| Gln | 42 | A | A | . | . | . | . | . | 1.23 | * | . | F | −0.15 | 0.77 |
| Leu | 43 | A | A | . | . | . | . | . | 1.23 | * | . | F | 0.60 | 2.19 |
| Thr | 44 | A | A | . | . | . | . | . | 0.38 | * | . | F | 0.90 | 2.73 |
| Glu | 45 | A | A | . | . | . | . | . | 0.97 | * | . | F | 0.90 | 1.17 |
| Lys | 46 | A | A | . | . | . | . | . | 0.96 | . | . | F | 0.90 | 1.90 |
| Asp | 47 | . | . | B | B | . | . | . | 0.64 | * | * | F | 0.90 | 1.90 |
| Val | 48 | A | . | . | B | . | . | . | 0.60 | . | . | F | 0.90 | 1.59 |
| Ser | 49 | . | . | B | B | . | . | . | 0.61 | * | . | F | 0.45 | 0.59 |
| Thr | 50 | . | . | B | B | . | . | . | 0.72 | * | . | F | −0.15 | 0.47 |
| Thr | 51 | . | . | B | B | . | . | . | 0.72 | * | . | F | 0.00 | 1.25 |
| Val | 52 | . | . | B | B | . | . | . | 0.13 | * | * | F | 0.90 | 1.86 |
| Ser | 53 | . | A | B | . | . | . | . | 0.70 | * | . | F | 0.90 | 1.30 |
| Arg | 54 | . | A | B | . | . | . | . | 0.66 | * | . | F | 0.45 | 0.95 |
| Lys | 55 | . | A | . | . | . | . | C | 0.38 | * | . | F | 0.80 | 1.26 |
| Ala | 56 | . | A | . | . | T | . | C | 0.69 | . | . | . | 0.70 | 0.95 |
| Trp | 57 | A | A | . | . | . | . | . | 0.96 | . | . | . | 0.60 | 0.84 |
| Gly | 58 | A | A | . | . | . | . | . | 0.40 | . | . | . | 0.30 | 0.43 |
| Ala | 59 | A | A | . | . | . | . | . | −0.06 | . | . | . | −0.60 | 0.31 |
| Glu | 60 | A | A | . | . | . | . | . | −0.77 | . | . | . | −0.60 | 0.29 |
| Ala | 61 | A | . | . | B | . | . | . | −0.48 | . | . | . | −0.30 | 0.16 |
| Val | 62 | A | . | . | B | . | . | . | −1.08 | * | * | . | −0.30 | 0.21 |
| Gly | 63 | . | . | . | B | T | . | . | −0.73 | * | * | . | 0.10 | 0.09 |
| Cys | 64 | . | . | B | B | . | . | . | −0.96 | . | * | . | −0.60 | 0.15 |
| Ser | 65 | . | . | B | B | . | . | . | −1.27 | . | * | . | −0.60 | 0.16 |
| Ile | 66 | . | . | B | B | . | . | . | −0.99 | . | * | . | −0.60 | 0.24 |
| Gln | 67 | . | . | B | B | . | . | . | −0.34 | . | * | . | −0.60 | 0.64 |
| Leu | 68 | . | . | B | B | . | . | . | −0.86 | . | * | . | −0.60 | 0.74 |
| Thr | 69 | . | . | B | B | . | . | . | −0.19 | . | * | F | −0.45 | 0.78 |
| Thr | 70 | . | . | B | B | . | . | . | −0.74 | . | * | F | −0.45 | 0.73 |
| Pro | 71 | . | . | B | B | . | . | . | −0.67 | . | * | F | −0.45 | 0.65 |
| Val | 72 | . | . | B | B | . | . | . | −1.52 | . | * | . | −0.60 | 0.37 |
| Asn | 73 | . | . | B | B | . | . | . | −1.60 | . | * | . | −0.60 | 0.19 |
| Val | 74 | . | . | B | B | . | . | . | −1.32 | . | . | . | −0.60 | 0.09 |
| Leu | 75 | . | . | B | B | . | . | . | −1.04 | . | . | . | −0.60 | 0.16 |
| Val | 76 | . | . | B | B | . | . | . | −1.69 | . | . | . | −0.60 | 0.14 |
| Ile | 77 | . | . | B | B | . | . | . | −1.04 | . | . | . | −0.60 | 0.14 |
| His | 78 | . | . | B | B | . | . | . | −1.39 | . | . | . | −0.60 | 0.25 |

TABLE III-continued (PGRP-W)

| Res | | Pos. | | | | | | | | | | | | |
|---|---|---|---|---|---|---|---|---|---|---|---|---|---|---|
| | I | II | III | IV | V | VI | VII | VIII | IX | X | XI | XII | XIII | XIV |
| His | 79 | . | . | B | B | . | . | . | −1.34 | . | . | . | −0.60 | 0.34 |
| Val | 80 | . | . | . | B | . | . | C | −0.53 | . | . | . | −0.40 | 0.40 |
| Pro | 81 | . | . | . | B | . | . | C | −0.34 | . | . | . | −0.10 | 0.51 |
| Gly | 82 | . | . | . | . | T | . | . | 0.51 | . | . | . | 0.30 | 0.20 |
| Leu | 63 | . | . | . | . | T | . | . | 0.54 | . | . | . | 0.30 | 0.37 |
| Glu | 84 | A | . | . | . | . | . | . | 0.58 | . | . | . | 0.50 | 0.39 |
| Cys | 85 | A | . | . | . | . | T | . | 1.12 | . | . | . | 0.70 | 0.69 |
| His | 86 | A | . | . | . | . | T | . | 0.48 | . | . | . | 0.85 | 1.21 |
| Asp | 87 | . | . | . | . | T | T | . | 0.16 | . | . | F | 1.25 | 0.52 |
| Gln | 88 | A | . | . | . | . | T | . | 0.67 | . | . | F | 0.25 | 0.52 |
| Thr | 89 | . | . | B | B | . | . | . | 0.67 | . | . | F | 0.45 | 0.51 |
| Val | 90 | . | . | B | B | . | . | . | 1.44 | . | * | F | 0.45 | 0.53 |
| Cys | 91 | . | . | B | B | . | . | . | 0.67 | . | * | F | 0.45 | 0.60 |
| Ser | 92 | . | . | B | B | . | . | . | 0.78 | . | * | F | −0.15 | 0.34 |
| Gln | 93 | . | . | B | B | . | . | . | 0.78 | * | * | F | 0.45 | 0.90 |
| Arg | 94 | A | . | . | B | . | . | . | 0.28 | * | * | F | 0.90 | 2.91 |
| Leu | 95 | A | . | . | B | . | . | . | 1.13 | * | * | F | 0.90 | 1.79 |
| Arg | 96 | A | . | . | B | . | . | . | 1.21 | * | * | F | 0.90 | 1.79 |
| Glu | 97 | A | A | . | . | . | . | . | 1.48 | . | * | . | 0.60 | 0.93 |
| Leu | 98 | A | A | . | . | . | . | . | 1.44 | * | * | . | 0.45 | 1.53 |
| Gln | 99 | A | A | . | . | . | . | . | 0.48 | . | * | . | 0.45 | 1.06 |
| Ala | 100 | A | A | . | . | . | . | . | 1.26 | . | . | . | −0.30 | 0.45 |
| His | 101 | A | A | . | . | . | . | . | 1.14 | . | . | . | −0.60 | 0.75 |
| His | 102 | A | A | . | . | . | . | . | 1.14 | . | * | . | −0.60 | 0.70 |
| Val | 103 | . | A | B | . | . | . | . | 1.66 | . | . | . | −0.45 | 1.11 |
| His | 104 | . | A | . | . | T | . | . | 1.31 | . | . | . | 0.50 | 1.09 |
| Asn | 105 | . | A | . | . | T | . | . | 1.23 | . | . | F | 0.75 | 0.79 |
| Asn | 106 | . | . | . | . | T | T | . | 1.27 | . | * | F | 1.40 | 0.57 |
| Ser | 107 | . | . | . | . | T | T | . | 0.44 | . | . | F | 2.25 | 0.70 |
| Gly | 108 | . | . | . | . | T | T | . | 0.71 | . | . | F | 2.50 | 0.32 |
| Cys | 109 | . | . | . | . | T | T | . | 0.50 | . | . | . | 2.10 | 0.20 |
| Asp | 110 | . | . | B | B | . | . | . | 0.50 | * | * | . | 0.45 | 0.24 |
| Val | 111 | . | . | B | B | . | . | . | −0.20 | * | * | . | 0.20 | 0.39 |
| Ala | 112 | . | . | B | B | . | . | . | −0.71 | * | * | . | −0.35 | 0.63 |
| Tyr | 113 | . | . | B | B | . | . | . | −1.22 | * | * | . | −0.60 | 0.31 |
| Asn | 114 | . | . | B | B | . | . | . | −0.90 | . | * | . | −0.60 | 0.31 |
| Phe | 115 | . | . | B | B | . | . | . | −0.90 | . | * | . | −0.29 | 0.30 |
| Leu | 116 | . | . | B | B | . | . | . | −0.04 | . | . | . | 0.02 | 0.32 |
| Val | 117 | . | . | B | B | . | . | . | 0.20 | . | * | . | 1.23 | 0.34 |
| Gly | 118 | . | . | . | . | T | T | . | 0.56 | . | * | F | 2.49 | 0.38 |
| Asp | 119 | . | . | . | . | T | T | . | −0.30 | . | * | F | 3.10 | 0.91 |
| Asp | 120 | . | . | . | . | . | T | C | 0.16 | * | * | F | 2.59 | 0.91 |
| Gly | 121 | . | . | . | . | . | T | C | 0.97 | * | * | F | 2.43 | 1.44 |
| Arg | 122 | . | . | B | B | . | . | . | 1.48 | * | * | F | 1.52 | 1.49 |
| Val | 123 | . | . | B | B | . | . | . | 0.97 | * | * | F | 1.06 | 0.89 |
| Tyr | 124 | . | . | B | B | . | . | . | 0.62 | * | * | . | 0.30 | 0.66 |
| Glu | 125 | . | . | B | B | . | . | . | 0.33 | . | * | . | 0.30 | 0.34 |
| Gly | 126 | . | . | . | B | T | . | . | 0.68 | * | * | . | −0.20 | 0.48 |
| Val | 127 | . | . | . | B | T | . | . | −0.32 | * | * | . | −0.20 | 0.49 |
| Gly | 128 | . | . | . | B | T | . | . | 0.53 | * | * | . | −0.20 | 0.20 |
| Trp | 129 | . | . | . | B | . | . | C | 0.43 | * | * | . | −0.40 | 0.35 |
| Asn | 130 | . | . | B | B | . | . | . | −0.42 | * | * | . | −0.60 | 0.46 |
| Ile | 131 | . | . | B | B | . | . | . | −0.11 | . | * | . | −0.60 | 0.35 |
| Gln | 132 | . | . | B | B | . | . | . | 0.43 | . | . | . | −0.60 | 0.45 |
| Gly | 133 | . | . | B | B | . | . | . | 0.78 | . | * | . | −0.60 | 0.40 |
| Val | 134 | . | . | B | B | . | . | . | 0.72 | . | * | F | −0.45 | 0.99 |
| His | 135 | . | . | B | B | . | . | . | 0.48 | * | . | F | −0.15 | 0.57 |
| Thr | 136 | . | . | B | . | . | T | . | 1.37 | * | . | F | −0.05 | 0.90 |
| Gln | 137 | . | . | B | . | . | T | . | 1.37 | . | * | F | 0.10 | 1.94 |
| Gly | 138 | . | . | . | . | T | T | . | 0.82 | . | * | F | 0.80 | 2.30 |
| Tyr | 139 | . | . | . | . | T | T | . | 1.38 | . | * | F | 0.50 | 1.12 |
| Asn | 140 | . | . | B | . | . | . | . | 0.60 | . | * | F | −0.25 | 0.86 |
| Asn | 141 | . | . | B | B | . | . | . | 0.57 | * | * | . | −0.60 | 0.72 |
| Ile | 142 | . | . | B | B | . | . | . | −0.13 | * | * | . | −0.60 | 0.45 |
| Ser | 143 | . | . | B | B | . | . | . | −0.38 | . | * | . | −0.60 | 0.24 |
| Leu | 144 | . | . | B | B | . | . | . | −0.83 | . | * | . | −0.60 | 0.15 |
| Gly | 145 | . | . | B | B | . | . | . | −1.53 | . | * | . | −0.60 | 0.19 |
| Phe | 146 | . | . | B | B | . | . | . | −1.88 | . | * | . | −0.60 | 0.12 |
| Ala | 147 | . | . | B | B | . | . | . | −1.30 | . | * | . | −0.60 | 0.15 |
| Phe | 148 | A | . | . | B | . | . | . | −0.96 | . | . | . | −0.60 | 0.21 |
| Phe | 149 | A | . | . | B | . | . | . | −0.10 | . | . | . | −0.26 | 0.50 |
| Gly | 150 | A | . | . | . | . | . | . | −0.10 | . | . | F | 1.33 | 0.98 |
| Thr | 151 | . | . | . | . | T | T | . | 0.57 | . | . | F | 2.42 | 1.12 |

TABLE III-continued (PGRP-W)

| Res | I | II | III | IV | V | VI | VII | VIII | IX | X | XI | XII | XIII | XIV |
|---|---|---|---|---|---|---|---|---|---|---|---|---|---|---|
| | | | | | | | | | Pos. | | | | | |
| Lys | 152 | . | . | . | . | . | T | T | . | 0.86 | . | . | F | 2.76 | 1.76 |
| Lys | 153 | . | . | . | . | . | T | T | . | 1.34 | . | . | F | 3.40 | 2.39 |
| Gly | 154 | . | . | . | . | . | T | T | . | 1.74 | . | . | F | 3.06 | 2.56 |
| His | 155 | . | . | . | . | . | . | . | C | 1.88 | . | . | F | 2.32 | 1.71 |
| Ser | 156 | . | . | . | . | . | T | . | C | 1.60 | . | . | F | 1.88 | 1.33 |
| Pro | 157 | . | . | . | . | . | . | T | C | 0.97 | . | . | F | 0.94 | 1.35 |
| Ser | 158 | . | . | . | . | . | . | T | C | 0.11 | . | . | F | 0.60 | 1.00 |
| Pro | 159 | A | . | . | . | . | . | T | . | 0.16 | . | . | F | 0.25 | 0.62 |
| Ala | 160 | A | A | . | . | . | . | . | . | −0.40 | . | . | . | −0.30 | 0.54 |
| Ala | 161 | A | A | . | . | . | . | . | . | −0.70 | . | . | . | −0.30 | 0.40 |
| Leu | 162 | A | A | . | . | . | . | . | . | −0.49 | . | . | . | −0.60 | 0.26 |
| Ser | 163 | A | A | . | . | . | . | . | . | −0.19 | * | . | . | −0.30 | 0.44 |
| Ala | 164 | A | A | . | . | . | . | . | . | −0.79 | * | . | . | −0.30 | 0.71 |
| Met | 165 | A | A | . | . | . | . | . | . | −1.09 | * | . | . | −0.30 | 0.71 |
| Glu | 166 | A | A | . | . | . | . | . | . | −0.81 | * | . | . | −0.30 | 0.37 |
| Asn | 167 | A | . | . | B | . | . | . | . | −0.24 | * | . | . | −0.30 | 0.53 |
| Leu | 168 | A | . | . | B | . | . | . | . | −0.53 | * | . | . | −0.60 | 0.83 |
| Ile | 169 | A | . | . | B | . | . | . | . | −0.80 | * | . | . | −0.60 | 0.49 |
| Thr | 170 | A | . | . | B | . | . | . | . | −0.20 | * | . | . | −0.60 | 0.22 |
| Tyr | 171 | A | . | . | B | . | . | . | . | −0.16 | * | . | . | −0.60 | 0.47 |
| Ala | 172 | A | . | . | B | . | . | . | . | −0.50 | * | . | . | −0.45 | 1.35 |
| Val | 173 | A | . | . | B | . | . | . | . | 0.28 | * | . | . | −0.30 | 0.92 |
| Gln | 174 | . | . | B | . | . | T | . | . | 0.36 | * | * | . | 0.27 | 0.80 |
| Lys | 175 | . | . | B | . | . | T | . | . | 0.37 | . | . | F | 0.59 | 0.65 |
| Gly | 176 | . | . | B | . | . | T | . | . | 0.31 | . | . | F | 0.91 | 1.18 |
| His | 177 | . | . | . | . | . | T | . | C | 0.60 | . | * | F | 1.73 | 0.91 |
| Leu | 178 | . | . | . | . | . | . | . | C | 1.21 | . | . | F | 1.70 | 0.61 |
| Ser | 179 | . | . | . | . | . | T | . | C | 0.36 | . | * | F | 0.83 | 0.97 |
| Ser | 180 | . | . | B | . | . | T | . | . | 0.31 | . | * | F | 0.46 | 0.53 |
| Ser | 181 | . | . | B | . | . | T | . | . | 0.44 | * | . | F | 0.44 | 1.11 |
| Tyr | 182 | . | . | B | . | . | T | . | . | −0.33 | * | . | F | 0.57 | 1.28 |
| Val | 183 | . | . | B | B | . | . | . | . | −0.33 | . | . | . | −0.60 | 0.79 |
| Gln | 184 | . | . | B | B | . | . | . | . | −0.38 | . | . | . | −0.60 | 0.49 |
| Pro | 185 | . | . | B | B | . | . | . | . | −0.03 | * | . | F | −0.45 | 0.31 |
| Leu | 186 | . | . | B | . | . | . | . | . | −0.08 | * | . | F | 0.30 | 0.83 |
| Leu | 187 | . | . | B | . | . | . | . | . | 0.17 | * | . | F | 0.55 | 0.47 |
| Gly | 188 | . | . | . | . | T | . | . | . | 1.02 | * | . | F | 1.80 | 0.53 |
| Lys | 189 | . | . | . | . | T | . | . | . | 0.36 | * | * | F | 2.20 | 1.03 |
| Gly | 190 | . | . | . | . | T | T | . | . | −0.24 | * | * | F | 2.50 | 0.67 |
| Glu | 191 | . | . | . | . | T | T | . | . | −0.02 | * | * | F | 2.25 | 0.56 |
| Asn | 192 | . | . | B | . | . | T | . | . | 0.58 | * | * | F | 1.60 | 0.28 |
| Cys | 193 | . | . | B | . | . | T | . | . | 1.03 | . | * | . | 0.60 | 0.44 |
| Leu | 194 | . | . | B | . | . | . | . | . | 0.99 | . | * | . | 0.75 | 0.50 |
| Ala | 195 | A | . | . | . | . | T | . | . | 1.38 | * | * | . | 0.70 | 0.54 |
| Pro | 196 | A | . | . | . | . | T | . | . | 1.07 | * | * | F | 1.00 | 2.00 |
| Arg | 197 | A | . | . | . | . | T | . | . | 0.77 | * | * | F | 1.30 | 3.51 |
| Gln | 198 | A | . | . | . | . | T | . | . | 0.62 | * | * | F | 1.30 | 4.65 |
| Lys | 199 | A | A | . | . | . | . | . | . | 1.48 | * | * | F | 0.90 | 2.48 |
| Thr | 200 | A | A | . | . | . | . | . | . | 2.11 | * | * | F | 0.90 | 2.53 |
| Ser | 201 | A | A | . | . | . | . | . | . | 1.51 | * | * | F | 0.90 | 2.92 |
| Leu | 202 | . | A | B | . | . | . | . | . | 0.81 | * | * | F | 0.90 | 1.21 |
| Lys | 203 | . | A | B | . | . | . | . | . | 0.60 | * | . | F | 0.45 | 0.84 |
| Lys | 204 | . | A | B | . | . | . | . | . | −0.03 | * | * | F | 0.45 | 0.97 |
| Leu | 205 | A | A | . | . | . | . | . | . | −0.53 | * | . | . | 0.45 | 1.19 |
| Ala | 206 | A | A | . | . | . | . | . | . | −0.53 | * | . | . | 0.30 | 0.49 |
| Pro | 207 | A | A | . | . | . | . | . | . | 0.24 | * | . | . | −0.30 | 0.33 |
| Ala | 208 | A | A | . | . | . | . | . | . | −0.14 | * | . | . | −0.60 | 0.54 |
| Leu | 209 | A | . | . | . | . | . | T | . | −1.00 | * | . | . | −0.20 | 0.53 |
| Ser | 210 | . | . | B | . | . | . | T | . | −0.86 | * | . | . | −0.20 | 0.28 |
| His | 211 | . | . | B | . | . | . | T | . | −0.61 | . | . | . | −0.20 | 0.15 |
| Gly | 212 | . | . | B | . | . | . | . | . | −0.40 | . | . | . | −0.20 | 0.18 |
| Leu | 213 | . | . | B | . | . | . | . | . | −0.02 | . | . | . | 0.84 | 0.23 |
| Cys | 214 | . | . | . | . | T | . | . | . | 0.44 | . | * | . | 0.98 | 0.27 |
| Gly | 215 | . | . | . | . | T | . | . | . | 0.86 | * | . | F | 2.07 | 0.27 |
| Glu | 216 | . | . | B | . | . | T | . | . | 0.68 | * | . | F | 2.21 | 0.63 |
| Pro | 217 | . | . | . | . | T | T | . | . | 0.21 | * | . | F | 3.40 | 1.82 |
| Gly | 218 | . | . | . | . | T | T | . | . | 0.72 | * | * | F | 3.06 | 1.52 |
| Arg | 219 | . | . | . | . | . | T | . | C | 1.50 | * | * | F | 2.52 | 1.17 |
| Pro | 220 | . | . | . | . | . | . | . | C | 1.24 | * | * | F | 1.98 | 1.49 |
| Leu | 221 | . | . | B | . | . | . | . | . | 0.93 | * | * | F | 1.14 | 1.49 |
| Ser | 222 | . | . | B | . | . | . | . | . | 0.33 | * | * | F | 0.80 | 1.10 |
| Arg | 223 | . | . | B | . | . | . | . | . | 0.47 | * | * | . | −0.10 | 0.58 |
| Met | 224 | . | . | B | . | . | . | . | . | −0.23 | * | * | . | 0.05 | 1.10 |

TABLE III-continued (PGRP-W)

| Res | | | | | | | Pos. | | | | | | | |
|---|---|---|---|---|---|---|---|---|---|---|---|---|---|---|
| | | I | II | III | IV | V | VI | VII | VIII | IX | X | XI | XII | XIII | XIV |
| Thr | 225 | . | . | B | . | . | . | . | 0.02 | * | * | . | −0.10 | 0.83 |
| Leu | 226 | . | . | B | . | . | . | . | 0.59 | * | * | . | 0.50 | 0.84 |
| Pro | 227 | A | . | . | . | . | . | . | 0.54 | * | * | . | −0.25 | 1.34 |
| Ala | 228 | A | . | . | . | . | T | . | −0.46 | . | * | . | 0.10 | 0.92 |
| Lys | 229 | A | . | . | . | . | T | . | −0.74 | . | * | . | −0.20 | 0.78 |
| Tyr | 230 | . | . | B | . | . | T | . | −1.32 | . | * | . | −0.20 | 0.35 |
| Gly | 231 | . | . | B | . | . | T | . | −0.54 | . | * | . | −0.20 | 0.24 |
| Ile | 232 | . | . | B | B | . | . | . | −0.64 | . | * | . | −0.60 | 0.17 |
| Ile | 233 | . | . | B | B | . | . | . | −0.64 | . | * | . | −0.60 | 0.15 |
| Ile | 234 | . | . | B | B | . | . | . | −1.03 | * | * | . | −0.60 | 0.16 |
| His | 235 | . | . | B | B | . | . | . | −0.68 | * | * | . | −0.60 | 0.22 |
| Thr | 236 | . | . | B | . | . | T | . | −0.64 | * | * | . | 0.10 | 0.62 |
| Ala | 237 | . | . | . | . | T | T | . | −0.42 | * | * | . | 0.65 | 1.27 |
| Gly | 238 | . | . | . | . | T | T | . | 0.47 | * | . | F | 1.25 | 0.50 |
| Arg | 239 | . | . | . | . | T | T | . | 0.47 | * | * | F | 1.25 | 0.56 |
| Thr | 240 | . | . | . | B | T | . | . | 0.20 | * | . | F | 0.25 | 0.39 |
| Cys | 241 | . | . | . | B | T | . | . | 0.51 | * | . | . | 1.01 | 0.52 |
| Asn | 242 | . | . | . | B | T | . | . | 1.10 | * | . | . | 1.32 | 0.45 |
| Ile | 243 | . | . | B | B | . | . | . | 0.78 | . | * | F | 1.38 | 0.54 |
| Ser | 244 | . | . | B | . | . | T | . | 0.78 | * | * | F | 2.09 | 0.54 |
| Asp | 245 | . | . | . | . | T | T | . | 0.28 | * | * | F | 3.10 | 0.65 |
| Glu | 246 | A | . | . | . | . | T | . | 0.13 | * | * | . | 2.24 | 0.77 |
| Cys | 247 | A | . | . | . | . | T | . | −0.72 | * | * | . | 1.93 | 0.47 |
| Arg | 248 | A | . | . | B | . | . | . | 0.28 | * | * | . | 0.92 | 0.21 |
| Leu | 249 | A | . | . | B | . | . | . | 0.58 | * | * | . | 0.61 | 0.24 |
| Leu | 250 | A | . | . | B | . | . | . | −0.31 | * | * | . | 0.30 | 0.74 |
| Val | 251 | A | . | . | B | . | . | . | −0.31 | * | * | . | 0.30 | 0.27 |
| Arg | 252 | A | . | . | B | . | . | . | 0.06 | * | * | . | −0.30 | 0.56 |
| Asp | 253 | . | . | B | B | . | . | . | −0.76 | * | * | F | 0.45 | 0.91 |
| Ile | 254 | . | . | B | B | . | . | . | −0.19 | * | * | F | 0.60 | 1.06 |
| Gln | 255 | . | . | B | B | . | . | . | −0.27 | * | * | F | −0.15 | 0.85 |
| Ser | 256 | . | . | B | B | . | . | . | 0.59 | * | . | . | −0.60 | 0.35 |
| Phe | 257 | . | . | B | B | . | . | . | 0.59 | * | . | . | −0.60 | 0.85 |
| Tyr | 258 | . | . | B | B | . | . | . | −0.22 | * | * | . | 0.01 | 0.96 |
| Ile | 259 | . | . | B | B | . | . | . | 0.71 | . | * | . | 0.32 | 0.59 |
| Asp | 260 | . | . | . | B | T | . | . | 0.41 | . | . | . | 1.78 | 1.36 |
| Arg | 261 | . | . | . | . | T | . | . | 0.04 | . | . | F | 2.44 | 1.16 |
| Leu | 262 | . | . | . | . | T | T | . | 0.74 | . | . | F | 3.10 | 0.89 |
| Lys | 263 | . | . | . | . | T | T | . | 0.10 | . | . | F | 2.79 | 0.89 |
| Ser | 264 | . | . | B | . | . | T | . | 0.64 | . | . | F | 2.08 | 0.32 |
| Cys | 265 | . | . | . | . | T | T | . | 0.40 | . | * | . | 1.72 | 0.38 |
| Asp | 266 | . | . | B | . | . | T | . | 0.29 | . | * | . | 1.01 | 0.30 |
| Ile | 267 | . | . | B | . | . | T | . | 0.40 | * | . | . | 0.10 | 0.36 |
| Gly | 268 | . | . | B | . | . | T | . | −0.46 | * | * | . | −0.20 | 0.58 |
| Tyr | 269 | . | . | B | . | . | T | . | −1.01 | . | * | . | −0.20 | 0.29 |
| Asn | 270 | . | . | B | B | . | . | . | −0.69 | . | * | . | −0.60 | 0.30 |
| Phe | 271 | . | . | B | B | . | . | . | −0.69 | . | * | . | −0.60 | 0.33 |
| Leu | 272 | . | . | B | B | . | . | . | 0.20 | . | * | . | −0.60 | 0.33 |
| Val | 273 | . | . | B | B | . | . | . | 0.20 | . | . | . | −0.30 | 0.35 |
| Gly | 274 | . | . | B | . | . | T | . | −0.14 | . | . | F | 0.25 | 0.40 |
| Gln | 275 | . | . | B | . | . | T | . | −1.03 | . | . | F | 0.25 | 0.49 |
| Asp | 276 | . | . | . | . | . | T | C | −0.58 | . | . | F | 0.45 | 0.46 |
| Gly | 277 | . | . | . | . | . | T | C | 0.23 | . | . | F | 0.45 | 0.73 |
| Ala | 278 | . | . | B | B | . | . | . | 0.74 | . | . | . | 0.30 | 0.73 |
| Ile | 279 | . | . | B | B | . | . | . | 0.23 | . | . | . | 0.30 | 0.43 |
| Tyr | 280 | . | . | B | B | . | . | . | −0.11 | . | . | . | −0.60 | 0.32 |
| Glu | 281 | . | . | B | B | . | . | . | −0.40 | . | . | . | −0.60 | 0.32 |
| Gly | 282 | . | . | . | B | T | . | . | −0.06 | . | * | . | −0.20 | 0.48 |
| Val | 283 | . | . | B | B | . | . | . | −0.32 | . | * | . | −0.60 | 0.49 |
| Gly | 284 | . | . | . | B | T | . | . | 0.57 | * | * | . | −0.20 | 0.21 |
| Trp | 285 | . | . | B | B | . | . | . | 0.47 | . | * | . | −0.60 | 0.37 |
| Asn | 286 | . | . | B | B | . | . | . | 0.17 | . | . | . | −0.60 | 0.49 |
| Val | 287 | . | . | B | . | . | T | . | 0.21 | . | * | F | −0.05 | 0.66 |
| Gln | 288 | . | . | B | . | . | T | . | 0.76 | . | * | F | −0.05 | 0.84 |
| Gly | 289 | . | . | . | . | T | T | . | 0.89 | . | * | F | 0.65 | 0.76 |
| Ser | 290 | . | . | . | . | T | T | . | 0.83 | . | * | F | 1.14 | 1.57 |
| Ser | 291 | . | . | . | . | . | . | C | 0.59 | . | * | F | 1.53 | 0.90 |
| Thr | 292 | . | . | . | . | . | T | C | 1.44 | . | * | F | 1.62 | 1.42 |
| Pro | 293 | . | . | . | . | . | T | C | 1.44 | . | . | F | 2.56 | 1.78 |
| Gly | 294 | . | . | . | . | T | T | . | 0.90 | . | . | F | 3.40 | 2.21 |
| Tyr | 295 | . | . | B | . | . | T | . | 0.61 | . | . | F | 2.36 | 1.07 |
| Asp | 296 | . | A | B | . | . | . | . | 0.10 | . | . | F | 1.47 | 0.70 |
| Asp | 297 | . | A | B | B | . | . | . | 0.07 | . | * | F | 0.53 | 0.59 |

TABLE III-continued (PGRP-W)

| Res | I | II | III | IV | V | VI | VII | VIII | IX | X | XI | XII | XIII | XIV |
|---|---|---|---|---|---|---|---|---|---|---|---|---|---|---|
| Ile | 298 | . | A | B | B | . | . | . | −0.61 | * | * | . | 0.04 | 0.37 |
| Ala | 299 | . | A | B | B | . | . | . | −0.58 | . | * | . | 0.30 | 0.16 |
| Leu | 300 | . | A | B | B | . | . | . | −1.03 | . | * | . | −0.60 | 0.13 |
| Gly | 301 | . | A | B | B | . | . | . | −1.63 | . | * | . | −0.60 | 0.17 |
| Ile | 302 | . | . | B | B | . | . | . | −1.98 | . | * | . | −0.60 | 0.16 |
| Thr | 303 | . | . | B | B | . | . | . | −1.40 | . | * | . | −0.60 | 0.19 |
| Phe | 304 | . | . | B | B | . | . | . | −1.51 | . | * | . | −0.60 | 0.28 |
| Met | 305 | . | . | B | B | . | . | . | −1.01 | . | * | . | −0.60 | 0.35 |
| Gly | 306 | . | . | B | B | . | . | . | −1.01 | . | * | . | −0.60 | 0.35 |
| Thr | 307 | . | . | B | B | . | . | . | −1.01 | . | * | . | −0.60 | 0.40 |
| Phe | 308 | . | . | B | B | . | . | . | −0.91 | . | . | F | −0.45 | 0.28 |
| Thr | 309 | . | . | . | B | T | . | . | −0.42 | . | . | F | −0.05 | 0.44 |
| Gly | 310 | . | . | . | . | . | . | C | 0.18 | . | . | F | −0.05 | 0.48 |
| Ile | 311 | . | . | . | . | . | . | C | −0.07 | . | . | F | −0.05 | 0.88 |
| Pro | 312 | . | . | . | . | . | T | C | −0.34 | . | . | F | 0.45 | 0.62 |
| Pro | 313 | . | . | . | . | . | T | C | −0.23 | . | . | F | 0.45 | 0.63 |
| Asn | 314 | . | . | . | . | . | T | C | −0.73 | . | . | . | 0.00 | 0.91 |
| Ala | 315 | A | . | . | . | . | T | . | −0.39 | . | . | . | −0.20 | 0.48 |
| Ala | 316 | A | A | . | . | . | . | . | −0.09 | . | . | . | −0.30 | 0.54 |
| Ala | 317 | A | A | . | . | . | . | . | −0.47 | . | . | . | −0.30 | 0.34 |
| Leu | 318 | A | A | . | . | . | . | . | −0.26 | . | . | . | −0.30 | 0.34 |
| Glu | 319 | A | A | . | . | . | . | . | −0.26 | * | . | . | −0.30 | 0.58 |
| Ala | 320 | A | A | . | . | . | . | . | −0.48 | * | . | . | 0.30 | 0.97 |
| Ala | 321 | A | A | . | . | . | . | . | −0.78 | * | . | . | 0.30 | 0.97 |
| Gln | 322 | A | A | . | . | . | . | . | −0.19 | * | . | . | 0.30 | 0.39 |
| Asp | 323 | A | A | . | . | . | . | . | −0.04 | * | . | . | −0.30 | 0.67 |
| Leu | 324 | A | A | . | . | . | . | . | −0.63 | * | . | . | −0.30 | 0.36 |
| Ile | 325 | A | A | . | . | . | . | . | −0.64 | * | . | . | −0.30 | 0.21 |
| Gln | 326 | A | A | . | . | . | . | . | −0.91 | * | . | . | −0.60 | 0.12 |
| Cys | 327 | A | A | B | . | . | . | . | −0.87 | * | . | . | −0.60 | 0.11 |
| Ala | 328 | . | A | B | . | . | . | . | −1.21 | * | . | . | −0.60 | 0.32 |
| Met | 329 | . | A | B | . | . | . | . | −0.64 | . | * | . | −0.30 | 0.18 |
| Val | 330 | . | A | B | . | . | . | . | −0.57 | . | * | . | −0.60 | 0.53 |
| Lys | 331 | . | A | B | . | . | . | . | −0.88 | . | * | . | −0.60 | 0.43 |
| Gly | 332 | . | A | B | . | . | . | . | −0.42 | . | * | . | −0.60 | 0.63 |
| Tyr | 333 | . | . | B | . | . | . | . | 0.17 | . | * | . | −0.25 | 1.31 |
| Leu | 334 | . | . | B | . | . | . | . | 0.52 | . | * | F | 0.20 | 1.05 |
| Thr | 335 | . | . | B | . | . | T | . | 0.57 | . | * | F | 0.10 | 1.67 |
| Pro | 336 | . | . | B | . | . | T | . | −0.29 | . | * | F | −0.05 | 0.88 |
| Asn | 337 | . | . | B | . | . | T | . | −0.80 | . | . | . | −0.20 | 0.88 |
| Tyr | 338 | . | . | B | . | . | T | . | −0.90 | . | . | . | −0.20 | 0.45 |
| Leu | 339 | . | . | B | B | . | . | . | −0.12 | . | . | . | −0.60 | 0.29 |
| Leu | 340 | . | . | B | B | . | . | . | −0.11 | . | . | . | −0.60 | 0.24 |
| Val | 341 | . | . | B | B | . | . | . | 0.10 | . | . | . | −0.60 | 0.21 |
| Gly | 342 | . | . | B | B | . | . | . | −0.76 | . | . | . | −0.30 | 0.42 |
| His | 343 | . | . | 3 | . | . | T | . | −1.10 | * | . | . | 0.10 | 0.38 |
| Ser | 344 | . | . | B | . | . | T | . | −0.18 | * | . | . | 0.10 | 0.52 |
| Asp | 345 | . | . | B | . | . | T | . | 0.32 | * | . | F | 1.30 | 1.03 |
| Val | 346 | . | . | B | . | . | T | . | 0.37 | * | . | . | 0.85 | 1.09 |
| Ala | 347 | . | . | B | B | . | . | . | 0.41 | * | . | . | 0.51 | 0.67 |
| Arg | 348 | . | . | B | B | . | . | . | 0.23 | * | . | F | 0.87 | 0.54 |
| Thr | 349 | . | . | B | B | . | . | . | 0.19 | * | . | F | 0.63 | 1.12 |
| Leu | 350 | . | . | B | B | . | . | . | 0.19 | * | . | F | 1.44 | 1.10 |
| Ser | 351 | . | . | . | . | . | T | C | 0.46 | * | . | F | 2.10 | 0.97 |
| Pro | 352 | . | . | . | . | . | T | C | 0.23 | * | * | F | 1.29 | 0.68 |
| Gly | 353 | . | . | . | . | T | T | . | −0.12 | * | . | F | 0.98 | 0.68 |
| Gln | 354 | . | . | B | . | . | T | . | 0.19 | * | * | F | 0.37 | 0.79 |
| Ala | 355 | . | . | B | . | . | . | . | 0.11 | * | . | . | −0.19 | 0.82 |
| Leu | 356 | . | . | B | B | . | . | . | −0.48 | * | . | . | −0.60 | 0.56 |
| Tyr | 357 | . | . | B | B | . | . | . | −0.57 | * | . | . | −0.60 | 0.24 |
| Asn | 358 | . | . | B | B | . | . | . | −0.53 | * | . | . | −0.60 | 0.31 |
| Ile | 359 | . | . | B | B | . | . | . | −0.12 | * | . | . | −0.60 | 0.55 |
| Ile | 360 | . | . | B | B | . | . | . | −0.44 | * | . | . | −0.60 | 0.37 |
| Ser | 361 | . | . | B | B | . | . | . | 0.33 | * | . | . | −0.60 | 0.35 |
| Thr | 362 | . | . | B | B | . | . | . | −0.12 | * | * | . | −0.60 | 0.69 |
| Trp | 363 | . | . | . | . | . | T | C | −0.08 | * | * | . | 0.00 | 0.85 |
| Pro | 364 | . | . | . | . | . | T | C | 0.78 | * | . | . | 0.15 | 1.27 |
| His | 365 | . | . | . | . | T | T | . | 1.28 | . | * | . | 0.35 | 1.20 |
| Phe | 366 | . | . | . | . | T | T | . | 1.19 | . | . | . | 0.35 | 1.45 |
| Lys | 367 | . | . | . | . | T | . | . | 1.11 | . | . | . | 0.45 | 1.20 |
| His | 368 | . | . | . | . | T | . | . | 1.01 | . | . | . | 0.45 | 1.13 |

TABLE IV (PGRP-C)

| Res | I | II | III | IV | V | VI | VII | VIII | IX | X | XI | XII | XIII | XIV |
|---|---|---|---|---|---|---|---|---|---|---|---|---|---|---|
| Met | 1 | . | . | B | . | . | . | . | 0.97 | * | . | . | 1.64 | 1.91 |
| Ser | 2 | . | . | B | . | . | T | . | 0.76 | . | . | . | 2.07 | 2.00 |
| Arg | 3 | . | . | B | . | . | T | . | 0.33 | . | . | . | 2.30 | 1.55 |
| Arg | 4 | . | . | B | . | . | T | . | −0.09 | . | . | . | 1.77 | 1.29 |
| Ser | 5 | . | . | B | . | . | T | . | −0.29 | . | . | . | 1.39 | 0.79 |
| Met | 6 | . | A | B | . | . | . | . | 0.02 | . | . | . | 0.76 | 0.41 |
| Leu | 7 | . | A | B | . | . | . | . | −0.27 | . | . | . | −0.37 | 0.22 |
| Leu | 8 | . | A | B | . | . | . | . | −1.19 | . | . | . | −0.60 | 0.17 |
| Ala | 9 | . | A | B | . | . | . | . | −1.51 | . | . | . | −0.60 | 0.14 |
| Trp | 10 | . | A | B | . | . | . | . | −1.51 | . | . | . | −0.60 | 0.26 |
| Ala | 11 | . | A | B | . | . | . | . | −1.72 | . | . | . | −0.60 | 0.42 |
| Leu | 12 | . | . | B | . | . | T | . | −1.72 | * | * | . | −0.20 | 0.34 |
| Pro | 13 | . | . | B | . | . | T | . | −0.80 | * | * | . | −0.20 | 0.27 |
| Ser | 14 | . | . | B | . | . | T | . | −1.02 | * | * | . | 0.10 | 0.52 |
| Leu | 15 | . | . | B | . | . | T | . | −1.08 | * | * | . | −0.20 | 0.52 |
| Leu | 16 | . | A | B | . | . | . | . | −1.08 | * | * | . | −0.30 | 0.33 |
| Arg | 17 | . | A | B | . | . | . | . | −0.86 | * | * | . | −0.30 | 0.25 |
| Leu | 18 | . | A | B | . | . | . | . | −0.64 | . | * | . | −0.60 | 0.31 |
| Gly | 19 | . | A | . | . | . | . | C | −0.34 | . | * | . | −0.10 | 0.65 |
| Ala | 20 | . | A | . | . | . | . | C | 0.16 | . | * | . | 0.50 | 0.57 |
| Ala | 21 | . | A | . | . | . | . | C | 0.97 | . | * | . | 0.65 | 1.00 |
| Gln | 22 | . | A | B | . | . | . | . | 0.86 | . | * | F | 1.21 | 1.75 |
| Glu | 23 | . | A | B | . | . | . | . | 1.46 | . | . | F | 1.52 | 2.90 |
| Thr | 24 | . | A | . | . | T | . | . | 1.21 | . | . | F | 2.23 | 4.44 |
| Glu | 25 | . | A | . | . | T | . | . | 1.13 | . | . | F | 2.54 | 2.59 |
| Asp | 26 | . | . | . | . | T | T | . | 1.06 | . | . | F | 3.10 | 0.80 |
| Pro | 27 | . | . | . | . | T | T | . | 0.76 | . | . | F | 2.49 | 0.30 |
| Ala | 28 | . | . | . | . | T | T | . | 0.54 | . | . | . | 2.33 | 0.23 |
| Cys | 29 | . | . | . | . | T | T | . | −0.03 | . | . | . | 1.72 | 0.21 |
| Cys | 30 | . | . | B | B | . | . | . | −0.89 | . | . | . | −0.29 | 0.10 |
| Ser | 31 | . | . | B | B | . | . | . | −1.10 | . | . | . | −0.60 | 0.07 |
| Pro | 32 | . | . | B | B | . | . | . | −0.78 | . | . | . | −0.60 | 0.20 |
| Ile | 33 | . | . | B | B | . | . | . | −0.19 | . | . | . | 0.00 | 0.75 |
| Val | 34 | . | . | B | . | . | T | . | 0.48 | . | * | F | 1.45 | 0.90 |
| Pro | 35 | . | . | B | . | . | T | . | 0.86 | . | * | F | 1.90 | 1.01 |
| Arg | 36 | . | . | . | . | T | T | . | 1.20 | . | * | F | 2.00 | 1.51 |
| Asn | 37 | . | . | . | . | . | T | C | 0.82 | * | * | F | 3.00 | 4.07 |
| Glu | 38 | . | A | . | . | T | . | . | 0.90 | * | * | F | 2.50 | 2.66 |
| Trp | 39 | . | A | . | . | T | . | . | 1.17 | * | * | F | 2.20 | 1.12 |
| Lys | 40 | . | A | . | . | . | . | C | 1.08 | * | * | . | 1.10 | 0.70 |
| Ala | 41 | . | A | . | . | . | . | C | 0.97 | * | * | . | 0.80 | 0.54 |
| Leu | 42 | . | A | . | . | . | . | C | 0.30 | * | . | . | 0.50 | 0.90 |
| Ala | 43 | A | A | . | . | . | . | . | −0.29 | * | * | . | 0.30 | 0.24 |
| Ser | 44 | A | A | . | . | . | . | . | 0.00 | * | . | . | −0.30 | 0.24 |
| Glu | 45 | A | A | . | . | . | . | . | −0.08 | * | . | . | −0.30 | 0.50 |
| Cys | 46 | A | A | . | . | . | . | . | −0.30 | * | . | . | 0.30 | 0.68 |
| Ala | 47 | A | A | . | . | . | . | . | 0.21 | . | . | . | −0.30 | 0.42 |
| Gln | 48 | . | A | B | . | . | . | . | −0.01 | . | . | . | −0.30 | 0.32 |
| His | 49 | . | A | B | . | . | . | . | 0.08 | * | * | . | −0.60 | 0.50 |
| Leu | 50 | . | A | B | . | . | . | . | −0.73 | * | * | . | −0.60 | 0.76 |
| Ser | 51 | . | A | B | . | . | . | . | 0.04 | * | * | . | −0.60 | 0.36 |
| Leu | 52 | . | . | B | . | . | . | . | 0.39 | * | * | . | −0.10 | 0.52 |
| Pro | 53 | . | . | B | B | . | . | . | −0.47 | * | * | . | −0.60 | 0.99 |
| Leu | 54 | . | . | B | B | . | . | . | −1.29 | . | * | . | −0.60 | 0.55 |
| Arg | 55 | . | . | B | B | . | . | . | −1.33 | . | * | . | −0.60 | 0.49 |
| Tyr | 56 | . | . | B | B | . | . | . | −1.33 | . | * | . | −0.60 | 0.24 |
| Val | 57 | . | . | B | B | . | . | . | −0.56 | . | * | . | −0.60 | 0.39 |
| Val | 58 | . | . | B | B | . | . | . | −0.66 | . | * | . | −0.60 | 0.27 |
| Val | 59 | . | . | B | B | . | . | . | −0.43 | . | * | . | −0.60 | 0.25 |
| Ser | 60 | . | . | B | . | . | . | . | −0.89 | . | . | . | −0.40 | 0.34 |
| His | 61 | . | . | B | . | . | . | . | −0.94 | . | . | . | −0.40 | 0.45 |
| Thr | 62 | . | . | B | . | . | . | . | −0.39 | . | . | . | −0.10 | 0.81 |
| Ala | 63 | . | . | . | . | T | . | . | −0.20 | . | . | F | 0.45 | 0.81 |
| Gly | 64 | . | . | . | . | T | T | . | 0.66 | . | . | F | 0.65 | 0.32 |
| Ser | 65 | . | . | . | . | T | T | . | 0.64 | . | . | F | 0.65 | 0.35 |
| Ser | 66 | . | . | . | . | T | T | . | 0.47 | . | . | F | 0.65 | 0.51 |
| Cys | 67 | . | . | . | . | T | T | . | 0.19 | . | . | F | 0.65 | 0.79 |
| Asn | 68 | . | . | . | . | T | . | . | 0.48 | . | . | F | 0.45 | 0.60 |
| Thr | 69 | . | . | . | . | . | . | C | 0.16 | . | . | F | 0.25 | 0.60 |
| Pro | 70 | . | . | . | . | T | T | . | 0.46 | . | . | F | 0.65 | 0.60 |
| Ala | 71 | . | . | . | . | T | T | . | 0.76 | . | . | F | 0.65 | 0.64 |
| Ser | 72 | . | . | B | . | . | T | . | 1.42 | . | * | F | 0.25 | 0.77 |
| Cys | 73 | . | . | B | . | . | T | . | 0.83 | * | * | F | 0.25 | 0.86 |

TABLE IV-continued (PGRP-C)

| Res | | Pos. | | | | | | | | | | | | |
|---|---|---|---|---|---|---|---|---|---|---|---|---|---|---|
| | I | II | III | IV | V | VI | VII | VIII | IX | X | XI | XII | XIII | XIV |
| Gln | 74 | . | A | B | . | . | . | . | 1.26 | . | * | F | −0.15 | 0.86 |
| Gln | 75 | . | A | B | . | . | . | . | 1.47 | * | * | F | 0.60 | 1.26 |
| Gln | 76 | . | A | B | . | . | . | . | 1.20 | * | * | F | 0.60 | 3.79 |
| Ala | 77 | . | A | B | . | . | . | . | 1.50 | * | . | F | 0.60 | 1.62 |
| Arg | 78 | . | A | B | . | . | . | . | 2.13 | * | . | F | 0.60 | 1.62 |
| Asn | 79 | . | A | B | . | . | . | . | 1.89 | * | . | . | 0.45 | 1.28 |
| Val | 80 | . | A | B | . | . | . | . | 1.86 | * | . | . | −0.15 | 1.98 |
| Gln | 81 | . | A | B | . | . | . | . | 1.26 | * | * | . | −0.15 | 1.37 |
| His | 82 | . | A | B | . | . | . | . | 1.89 | * | * | . | −0.60 | 0.85 |
| Tyr | 83 | . | . | B | . | . | . | . | 1.47 | * | . | . | −0.25 | 2.28 |
| His | 84 | . | . | B | . | . | . | . | 0.66 | . | . | . | 0.05 | 1.90 |
| Met | 85 | . | . | B | B | . | . | . | 1.17 | . | . | . | −0.45 | 1.15 |
| Lys | 86 | . | . | B | B | . | . | . | 0.88 | . | . | . | −0.60 | 0.73 |
| Thr | 87 | . | . | . | B | T | . | . | 0.24 | . | . | . | −0.20 | 0.56 |
| Leu | 88 | . | . | . | B | T | . | . | 0.49 | . | * | . | −0.20 | 0.30 |
| Gly | 89 | . | . | . | B | T | . | . | −0.33 | . | . | . | 0.10 | 0.25 |
| Trp | 90 | . | . | B | B | . | . | . | −0.08 | . | . | . | −0.60 | 0.13 |
| Cys | 91 | . | . | B | B | . | . | . | −0.37 | . | . | . | −0.60 | 0.16 |
| Asp | 92 | . | . | B | . | . | T | . | −0.06 | . | * | . | −0.20 | 0.25 |
| Val | 93 | . | . | B | . | . | T | . | 0.06 | * | . | . | −0.20 | 0.38 |
| Gly | 94 | . | . | . | . | . | T | . | −0.41 | . | * | . | −0.20 | 0.61 |
| Tyr | 95 | . | . | B | . | . | T | . | −1.01 | . | * | . | −0.20 | 0.30 |
| Asn | 96 | . | . | B | B | . | . | . | −0.69 | . | * | . | −0.60 | 0.29 |
| Phe | 97 | . | . | B | B | . | . | . | −0.69 | . | * | . | −0.60 | 0.29 |
| Leu | 98 | . | . | B | B | . | . | . | 0.17 | . | * | . | −0.60 | 0.32 |
| Ile | 99 | . | . | B | B | . | . | . | 0.17 | . | . | . | 0.30 | 0.33 |
| Gly | 100 | . | . | B | . | . | T | . | −0.40 | . | . | . | 0.10 | 0.38 |
| Glu | 101 | . | . | B | . | . | T | . | −1.26 | . | . | F | 0.85 | 0.38 |
| Asp | 102 | . | . | . | . | T | T | . | −0.80 | . | . | F | 1.25 | 0.40 |
| Gly | 103 | . | . | . | . | . | T | C | 0.01 | . | . | F | 1.05 | 0.63 |
| Leu | 104 | . | . | B | . | . | . | . | 0.56 | * | * | . | 0.50 | 0.63 |
| Val | 105 | . | . | B | . | . | . | . | 1.01 | * | * | . | 0.78 | 0.37 |
| Tyr | 106 | . | . | B | . | . | . | . | 0.67 | * | * | . | 1.06 | 0.74 |
| Glu | 107 | . | . | B | . | . | . | . | 0.38 | * | . | F | 1.49 | 0.89 |
| Gly | 108 | . | . | . | . | T | T | . | 0.72 | . | . | F | 1.92 | 1.25 |
| Arg | 109 | . | . | . | . | T | T | . | 0.83 | . | * | F | 2.80 | 1.29 |
| Gly | 110 | . | . | . | . | T | T | . | 1.38 | . | . | F | 2.37 | 0.64 |
| Trp | 111 | . | . | . | . | T | T | . | 1.28 | . | * | . | 1.04 | 0.94 |
| Asn | 112 | . | . | . | . | . | . | C | 0.69 | . | . | . | 0.36 | 0.47 |
| Phe | 113 | . | . | B | . | . | . | . | 1.00 | . | . | . | −0.12 | 0.48 |
| Thr | 114 | . | . | . | . | . | . | C | 0.59 | . | . | . | −0.20 | 0.63 |
| Gly | 115 | . | . | . | . | . | . | C | 0.59 | . | * | . | −0.20 | 0.52 |
| Ala | 116 | . | . | . | . | . | . | C | 0.84 | . | * | . | −0.20 | 0.60 |
| His | 117 | . | . | . | . | . | T | C | 0.03 | . | . | . | 0.30 | 0.56 |
| Ser | 118 | . | . | . | . | . | T | C | 0.44 | . | . | . | 0.00 | 0.47 |
| Gly | 119 | . | . | . | . | . | T | C | 0.76 | . | . | . | 0.00 | 0.49 |
| His | 120 | . | . | . | . | . | T | C | 0.89 | . | . | . | 0.00 | 0.58 |
| Leu | 121 | . | . | . | . | T | . | . | 0.88 | . | . | . | 0.00 | 0.67 |
| Trp | 122 | . | . | . | . | . | . | C | 0.61 | . | . | . | −0.20 | 0.67 |
| Asn | 123 | . | . | . | . | . | . | C | 0.02 | . | . | . | −0.20 | 0.66 |
| Pro | 124 | . | . | . | B | B | . | . | 0.02 | . | * | . | −0.60 | 0.56 |
| Met | 125 | . | . | . | B | T | . | . | −0.83 | * | * | . | −0.20 | 0.52 |
| Ser | 126 | . | . | B | B | . | . | . | −0.32 | . | * | . | −0.60 | 0.23 |
| Ile | 127 | . | . | B | B | . | . | . | −0.73 | . | * | . | −0.60 | 0.20 |
| Gly | 128 | . | . | B | B | . | . | . | −1.33 | . | * | . | −0.60 | 0.17 |
| Ile | 129 | . | . | B | B | . | . | . | −1.47 | . | * | . | −0.60 | 0.13 |
| Ser | 130 | . | . | B | B | . | . | . | −0.87 | . | * | . | −0.60 | 0.18 |
| Phe | 131 | . | . | B | B | . | . | . | −0.81 | . | * | . | −0.60 | 0.29 |
| Met | 132 | . | . | B | . | . | T | . | −0.52 | . | * | . | −0.20 | 0.66 |
| Gly | 133 | . | . | . | . | T | T | . | −0.18 | * | * | . | 0.20 | 0.48 |
| Asn | 134 | . | . | . | . | T | T | . | 0.82 | * | * | . | 0.20 | 0.93 |
| Tyr | 135 | . | . | . | . | T | T | . | 0.27 | * | * | . | 1.25 | 1.85 |
| Met | 136 | . | . | . | . | T | . | . | 0.76 | * | * | . | 1.31 | 1.39 |
| Asp | 137 | . | . | . | . | T | . | . | 1.04 | * | * | . | 1.57 | 1.33 |
| Arg | 138 | . | . | B | . | . | . | . | 1.18 | * | * | F | 1.58 | 1.23 |
| Val | 139 | . | . | B | . | . | T | . | 1.18 | * | . | F | 2.04 | 1.92 |
| Pro | 140 | . | . | B | . | . | T | . | 0.83 | . | . | F | 2.60 | 1.99 |
| Thr | 141 | . | . | . | . | . | T | C | 0.54 | . | * | F | 2.24 | 1.03 |
| Pro | 142 | . | . | B | . | . | T | . | 0.66 | . | * | F | 0.73 | 0.97 |
| Gln | 143 | . | A | B | . | . | . | . | −0.04 | * | * | F | 1.12 | 1.23 |
| Ala | 144 | . | A | B | . | . | . | . | 0.22 | * | . | . | 0.56 | 0.86 |
| Ile | 145 | . | A | B | . | . | . | . | 0.43 | * | . | . | −0.30 | 0.56 |
| Arg | 146 | . | A | B | . | . | . | . | 0.40 | * | . | . | 0.30 | 0.56 |

TABLE IV-continued (PGRP-C)

| Res | I | II | III | IV | V | VI | VII | VIII | IX | X | XI | XII | XIII | XIV |
|---|---|---|---|---|---|---|---|---|---|---|---|---|---|---|
| | | | | | | | | | Pos. | | | | | |
| Ala | 147 | . | A | B | . | . | . | . | −0.20 | * | . | . | −0.30 | 0.55 |
| Ala | 148 | . | A | B | . | . | . | . | −1.01 | * | . | . | −0.30 | 0.65 |
| Gln | 149 | . | A | B | . | . | . | . | −1.01 | * | * | . | −0.30 | 0.27 |
| Gly | 150 | . | A | B | . | . | . | . | −0.79 | * | * | . | −0.60 | 0.27 |
| Leu | 151 | . | A | B | . | . | . | . | −1.24 | * | . | . | −0.60 | 0.14 |
| Leu | 152 | . | A | B | . | . | . | . | −1.51 | . | . | . | −0.60 | 0.08 |
| Ala | 153 | . | A | B | . | . | . | . | −1.51 | . | . | . | −0.60 | 0.06 |
| Cys | 154 | . | A | B | . | . | . | . | −1.51 | . | . | . | −0.60 | 0.08 |
| Gly | 155 | . | A | B | . | . | . | . | −1.51 | . | . | . | −0.60 | 0.16 |
| Val | 156 | . | A | B | . | . | . | . | −1.29 | . | . | . | −0.60 | 0.16 |
| Ala | 157 | . | A | B | . | . | . | . | −1.29 | * | * | . | −0.60 | 0.29 |
| Gln | 158 | . | A | B | . | . | . | . | −0.59 | * | * | . | −0.60 | 0.25 |
| Gly | 159 | . | A | B | . | . | . | . | −0.22 | * | * | . | −0.30 | 0.65 |
| Ala | 160 | . | A | B | . | . | . | . | 0.12 | * | * | F | 0.45 | 0.86 |
| Leu | 161 | . | A | B | . | . | . | . | 0.73 | * | * | F | 0.45 | 0.80 |
| Arg | 162 | . | . | B | . | . | T | . | 0.47 | * | * | F | 0.40 | 1.26 |
| Ser | 163 | . | . | B | . | . | T | . | −0.34 | * | * | F | 0.25 | 0.93 |
| Asn | 164 | . | . | B | . | . | T | . | 0.04 | . | * | F | −0.05 | 0.93 |
| Tyr | 165 | . | . | B | . | . | T | . | 0.29 | . | * | . | 0.70 | 0.95 |
| Val | 166 | . | . | B | B | . | . | . | 1.07 | . | * | . | −0.12 | 0.70 |
| Leu | 167 | . | . | B | B | . | . | . | 1.07 | * | * | . | −0.24 | 0.59 |
| Lys | 168 | . | . | B | B | . | . | . | 1.37 | * | . | F | 0.39 | 0.74 |
| Gly | 169 | . | . | B | . | . | . | . | 0.51 | * | * | F | 1.82 | 1.67 |
| His | 170 | . | . | B | B | . | . | . | 0.76 | * | . | F | 1.80 | 1.50 |
| Arg | 171 | . | . | B | B | . | . | . | 1.72 | * | . | F | 1.62 | 1.30 |
| Asp | 172 | . | . | B | B | . | . | . | 2.22 | * | . | F | 1.44 | 2.57 |
| Val | 173 | . | . | B | B | . | . | . | 1.37 | * | . | F | 1.26 | 2.72 |
| Gln | 174 | . | . | B | B | . | . | . | 1.41 | * | . | F | 1.08 | 1.15 |
| Arg | 175 | . | . | B | B | . | . | . | 1.23 | * | . | F | 0.57 | 0.92 |
| Thr | 176 | . | . | B | B | . | . | . | 0.78 | * | . | F | 0.24 | 1.92 |
| Leu | 177 | . | . | . | B | . | . | C | 0.78 | * | . | F | 1.16 | 1.10 |
| Ser | 178 | . | . | . | . | . | T | C | 1.63 | * | . | F | 1.53 | 0.90 |
| Pro | 179 | . | . | . | . | . | T | C | 0.82 | * | . | F | 1.20 | 1.08 |
| Gly | 180 | . | . | . | . | T | T | . | 0.47 | * | . | F | 0.98 | 1.08 |
| Asn | 181 | . | . | . | . | T | T | . | 0.74 | . | . | F | 0.86 | 1.26 |
| Gln | 182 | . | A | B | . | . | . | . | 0.74 | * | . | F | −0.06 | 1.11 |
| Leu | 183 | . | A | B | . | . | . | . | 0.16 | * | . | . | −0.48 | 0.93 |
| Tyr | 184 | . | A | B | . | . | . | . | 0.37 | * | . | . | −0.60 | 0.40 |
| His | 185 | . | A | B | . | . | . | . | 0.71 | * | . | . | −0.60 | 0.40 |
| Leu | 186 | . | A | B | . | . | . | . | 0.42 | * | . | . | −0.60 | 0.79 |
| Ile | 187 | . | A | B | . | . | . | . | 0.21 | * | . | . | −0.60 | 0.53 |
| Gln | 188 | . | A | B | . | . | . | . | 0.99 | * | . | . | −0.60 | 0.60 |
| Asn | 189 | . | A | . | . | T | . | . | 0.99 | . | * | . | −0.20 | 0.99 |
| Trp | 190 | . | . | . | . | . | T | C | 1.13 | . | * | . | 0.15 | 2.21 |
| Pro | 191 | . | . | . | . | . | T | C | 1.64 | . | * | . | 0.45 | 2.50 |
| His | 192 | . | . | . | . | T | T | . | 2.32 | . | * | . | 0.86 | 2.09 |
| Tyr | 193 | . | . | . | . | T | T | . | 1.93 | . | . | . | 0.77 | 3.07 |
| Arg | 194 | . | . | . | . | T | . | . | 1.54 | . | . | . | 1.68 | 2.54 |
| Ser | 195 | . | . | . | . | . | . | C | 1.44 | . | . | . | 1.69 | 2.38 |
| Pro | 196 | . | . | . | . | T | . | . | 1.27 | . | * | . | 2.10 | 1.94 |

Among highly preferred fragments in this regard are those that comprise regions of PGRP-K (SEQ ID NO:2), PGRP-W (SEQ ID NO:4), AND PGRP-C (SEQ ID NO:6) that combine several structural features, such as several of the features set out above.

The polypeptides of the present invention could be used as molecular weight markers on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting PGRP-K, PGRP-W, and/or PGRP-C protein expression as described below or as agonists and antagonists capable of enhancing or inhibiting PGRP-K, PGRP-W, and/or PGRP-C protein function. Further, such polypeptides can be used in the yeast two-hybrid system to "capture" PGRP-K, PGRP-W, and/or PGRP-C protein binding proteins which are also candidate agonists and antagonists according to the present invention. The yeast two hybrid system is described in Fields and Song, Nature 340:245–246 (1989).

Epitope-Bearing Portions

In another aspect, the invention provides a peptide or polypeptide comprising an epitope-bearing portion of a polypeptide of the invention. The epitope of this polypeptide portion is an immunogenic or antigenic epitope of a polypeptide of the invention. The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Antigenic epitope-bearing peptides and polypeptides of the invention preferably contain a sequence of at least seven, more preferably at least nine and most preferably between about 15 to about 30 amino acids contained within the amino acid sequences of the polypeptides of the invention. Non-limiting examples of antigenic polypeptides or peptides that can be used to generate PGRP-K specific antibodies include: a polypeptide comprising amino acid residues from about Val-24 to about Ala-35 in FIGS. 1A–B (SEQ ID NO:2); a polypeptide comprising amino acid residues from about Gln-51 to about Gln-58 in FIGS. 1A–B (SEQ ID NO:2); a polypeptide comprising amino acid residues from about Gly-69 to about Ser-72 in FIGS. 1A–B (SEQ ID NO:2); a polypeptide comprising amino acid residues from about Leu-88 to about Gly-100 in FIGS. 1A–B (SEQ ID NO:2); a polypeptide comprising amino acid residues from about His-107 to about Tyr-111 in FIGS. 1A–B (SEQ ID NO:2); a polypeptide comprising amino acid residues from about Gly-122 to about Pro-131 in FIGS. 1A–B (SEQ ID NO:2); a polypeptide comprising amino acid residues from about Gln-146 to about Ile-155 in FIGS. 1A–B (SEQ ID NO:2); a polypeptide comprising amino acid residues from about Leu-159 to about His-170 in FIGS. 1A–B (SEQ ID NO:2); a polypeptide comprising amino acid residues from about Val-172 to about Pro-200 in FIGS. 1A–B (SEQ ID NO:2); a polypeptide comprising amino acid residues from about Gly-211 to about Val-223 in FIGS. 1A–B (SEQ ID NO:2); a polypeptide comprising amino acid residues from about Phe-230 to about Tyr-242 in FIGS. 1A–B (SEQ ID NO:2).

Non-limiting examples of antigenic polypeptides or peptides that can be used to generate PGRP-W specific antibodies include: a polypeptide comprising amino acid residues from about Gly-17 to about Gly-32 in FIGS. 2A–C (SEQ ID NO:4); a polypeptide comprising amino acid residues from about Ile-40 to about Gly-58 in FIGS. 2A–C (SEQ ID NO:4); a polypeptide comprising amino acid residues from about Gly-82 to about Gln-99 in FIGS. 2A–C (SEQ ID NO:4); a polypeptide comprising amino acid residues from about His-104 to about Val-111 in FIGS. 2A–C (SEQ ID NO:4); a polypeptide comprising amino acid residues from about Leu-116 to about Glu-125 in FIGS. 2A–C (SEQ ID NO:4); a polypeptide comprising amino acid residues from about Gly-150 to about Pro-159 in FIGS. 2A–C (SEQ ID NO:4); a polypeptide comprising amino acid residues from about Gln-174 to about Tyr-182 in FIGS. 2A–C (SEQ ID NO:4); a polypeptide comprising amino acid residues from about Leu-186 to about Pro-207 in FIGS. 2A–C (SEQ ID NO:4); a polypeptide comprising amino acid residues from about Val-214 to about Met-225 in FIGS. 2A–C (SEQ ID NO:4); a polypeptide comprising amino acid residues from about Thr-237 to about Val-252 in FIGS. 2A–C (SEQ ID NO:4); a polypeptide comprising amino acid residues from about Tyr-259 to about Ile-268 in FIGS. 2A–C (SEQ ID NO:4); a polypeptide comprising amino acid residues from. about Gly-290 to about Ala-300 in FIGS. 2A–C (SEQ ID NO:4); a polypeptide comprising amino acid residues from about His-344 to about Gln-355 in FIGS. 2A–C (SEQ ID NO:4); a polypeptide comprising amino acid residues from about Trp-364 to about His-369 in FIGS. 2A–C (SEQ ID NO:4).

Non-limiting examples of antigenic polypeptides or peptides that can be used to generate PGRP-C specific antibodies include: a polypeptide comprising amino acid residues from about Met-1 to about Met-6 in FIG. 3 (SEQ ID NO:6); a polypeptide comprising amino acid residues from about Ala-20 to about Cys-29 in FIG. 3 (SEQ ID NO:6); a polypeptide comprising amino acid residues from about Ile-33 to about Ala-43 in FIG. 3 (SEQ ID NO:6); a polypeptide comprising amino acid residues from about Ala-63 to about Asn-79 in FIG. 3 (SEQ ID NO:6); a polypeptide comprising amino acid residues from about Ile-99 to about Asn-112 in FIG. 3 (SEQ ID NO:6); a polypeptide comprising amino acid residues from about Gly-133 to about Arg-146 in FIG. 3 (SEQ ID NO:6); a polypeptide comprising amino acid residues from about Ala-160 to about Tyr-165 in FIG. 3 (SEQ ID NO:6); a polypeptide comprising amino acid residues from about Lys-168 to about Asn-181 in FIG. 3 (SEQ ID NO:6); and a polypeptide comprising amino acid residues from about Trp-190 to about Pro-196 in FIG. 3 (SEQ ID NO:6). These polypeptide fragments have been determined to bear antigenic epitopes of the PGRP-K, PGRP-W, and PGRP-C proteins, respectively, by the analysis of the Jameson-Wolf antigenic index, as shown in FIGS. 6, 8, and 10, above.

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2): 76–82 (1998); Hansson, et al., J. Mol. Biol. 287:265–76 (1999); and Lorenzo and Blasco, Biotechniques 24(2): 308–13 (1998) (each of these patents and publications are hereby incorporated by reference in its entirety). In one embodiment, alteration of polynucleotides corresponding to SEQ ID NO:X and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Fusion Proteins

As one of skill in the art will appreciate, PGRP-K, PGRP-W, and/or PGRP-C polypeptides of the present invention and the epitope-bearing fragments thereof described above can be combined with parts of the constant domain of immunoglobulins (agG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., Nature 331:84–86 (1988)). Fusion proteins that have a disulfide-linked dimeric structure due to the IgG part can also be more efficient in binding and neutralizing other molecules than the monomeric PGRP-K, PGRP-W, and/or PGRP-C proteins or protein fragments alone (Fountoulakis et al., J. Biochem. 270:3958–3964 (1995)).

Detection of Disease States

Cells which express either the PGRP-K, PGRP-W and/or PGRP-C polypeptides are believed to have a potent cellular response to infection include, for example, keratinocyte cells, wound-healing tissues, vascular tissues, endothelial tissues, and tissues of the immune, nervous, and endocrine systems. Furthermore, it is believed that cells which express either the PGRP-K, PGRP-W and/or PGRP-C polypeptides regulate apoptosis and/or the proliferation of keratinocytes, epidermal cells, and epithelial cells, as well as mediating the recognition of pathogens (e.g., bacteria) and the processing and presentation of antigens to the immune system. By "a potent cellular response to infection" is intended any genotypic, phenotypic, and/or morphologic change to a cell, cell line, tissue, tissue culture or patient that is induced by infection from bacterial (Gram positive and negative), viral, fungal, parasitic, etc. As indicated, such cellular responses include not only normal physiological responses infection (e.g., antigenic processing and presentation, immune response), but also diseases associated with aberrant immune system recognition, aberrant antigen processing and presentation in the immune system, aberrant immune system responses to infection, activation, survival, migration and differentiation of immune cells, as well as infections of immuno-compromised individuals, and aberrant regulation of the proliferation/apoptosis of keratinocytes and/or other cells in the body (e.g., immune system cells).

Thus, it is believed that certain tissues in mammals with certain diseases and infections (e.g., bacterial infection of immuno-compromised individuals), diseases associated with increased or decreased cell survival, secretion, activation, migration, differentiation, and proliferation; diseases associated with the defects of wound healing, keratinocyte and cartilage proliferation, cellular immunity, immune dysfunction, and endocrine dysfunction; express significantly altered (e.g., enhanced or decreased) levels of either the PGRP-K, PGRP-W and/or PGRP-C polypeptides and mRNAs encoding the PGRP-K, PGRP-W and/or PGRP-C polypeptides when compared to a corresponding "standard" mammal, i.e., a mammal of the same species not having the disease. Diseases associated with defects in the proliferation of keratinocytes or cartilagenous tissues, include, for example, skin or cartilagenous cancers (such as Chondrosarcomas, basal cell carcinomas, squamous cell carcinomas, melanomas, Chondromatosis, Dyschondroplasia). Diseases associated with immune dysfunction and decreased cellular immunity include, for example, bacterial infections (e.g., cutaneous infection due to Mycobacterium gordonae in an AIDS patient) and diseases associated with bacterial infection of the skin (e.g., boils, cellulitis, erysipelas, impetigo).

Further, it is believed that altered levels of either the PGRP-K, PGRP-W and/or PGRP-C polypeptide can be detected in certain body fluids (e.g., lymph, sera, plasma, urine, and spinal fluid) from mammals with the disorder when compared to sera from mammals of the same species not having the disorder. Thus, the invention provides a diagnostic method useful during diagnosis, which involves assaying the expression level of the gene encoding the PGRP-K, PGRP-W and/or PGRP-C polypeptide(s) in mammalian cells or body fluid and comparing the gene expression level with a standard PGRP-K, PGRP-W and/or PGRP-C gene expression level, whereby an increase or decrease in the gene expression level over the standard is indicative of the disease.

By "assaying" the expression level of the gene encoding either the "PGRP-K, PGRP-W and/or PGRP-C polypeptide" is intended qualitatively or quantitatively measuring or estimating the level of the PGRP-K, PGRP-W and/or PGRP-C polypeptide(s) or the level of the mRNA encoding either the PGRP-K, PGRP-W and/or PGRP-C polypeptide (s) in a first biological sample either directly (e.g., by determining or estimating absolute polypeptide or mRNA level) or relatively (e.g., by comparing to either the PGRP-K, PGRP-W and/or PGRP-C polypeptide(s) level or mRNA level in a second biological sample). Preferably, the PGRP-K, PGRP-W and/or PGRP-C protein level or mRNA level in the first biological sample is measured or estimated and compared to a standard PGRP-K, PGRP-W and/or PGRP-C protein level or mRNA level, the standard being taken from a second biological sample obtained from an individual not having the disease state. As will be appreciated in the art, once a standard PGRP-K, PGRP-W and/or PGRP-C protein level or mRNA level is known, it can be used repeatedly as a standard for comparison.

By "biological sample" is intended any biological sample obtained from an individual, cell line, tissue culture, or other source which contains PGRP-K, PGRP-W and/or PGRP-C protein or mRNA. Biological samples include mammalian body fluids (such as lymph, sera, plasma, urine, synovial fluid and spinal fluid), and keratinocytes, wound-healing tissues, human chondrosarcoma, and other tissues. Methods for obtaining tissue biopsies and body fluids from mammals are well known in the art. Where the biological sample is to include mRNA, a tissue biopsy is the preferred source. Where a diagnosis has already been made according to conventional methods, the present invention is useful as a prognostic indicator, whereby patients exhibiting altered PGRP-K, PGRP-W and/or PGRP-C gene expression win experience a worse clinical outcome relative to patients expressing the gene at a normal level.

Nucleic acids for diagnosis may be obtained from a biological sample of a subject, such as from blood, urine, saliva, tissue biopsy or autopsy material, using techniques known in the art. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled PGRP-K, PGRP-W, and/or PGRP-C nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (see, e.g., Myers et al., Science 230:1242 (1985)). Sequence changes at specific locations may also be revealed by nuclease protection assays, such as RNase and S1 protection or the chemical cleavage method (see Cotton et al., Proc. Natl. Acad. Sci. USA 85:4397–4401 (1985)). In another embodiment, an array of oligonucleotides probes comprising either PGRP-K, PGRP-W, and/or PGRP-C polynucleotide sequences or fragments thereof, can be constructed to conduct efficient screening of e.g., genetic mutations. Array technology methods are well known and have general applicability and can be used to address a variety of questions in molecular genetics including gene expression, genetic linkage, and genetic variability (see for example, Chee et al., Science 274:610–613 (1996)). The diagnostic assays offer a process for diagnosing or determining a susceptibility to specific diseases through detection of mutations in the PGRP-K, PGRP-W and/or PGRP-C genes by the methods described herein or otherwise known in the art.

In addition, specific diseases can be diagnosed by methods comprising determining from a sample derived from a subject an abnormally decreased or increased level of PGRP-K, PGRP-W and/or PGRP-C polypeptides or mRNAs. Decreased or increased expression can be measured at the RNA level using any of the methods well known in the art, which include, but are not limited to, Northern blot analysis, (Harada et al., Cell 63:303–312 (1990)), S1 nuclease mapping (Fijita et al., Cell 49:357–367 (1987)), RNAse protection, the polymerase chain reaction (PCR), reverse transcription in combination with the polymerase chain reaction (RT-PCR) (Makino et al., Technique 2:295–301 (1990), reverse transcription in combination with the ligase chain reaction (RT-LCR) and other hybridization methods.

Assaying PGRP-K, PGRP-W, and/or PGRP-C polypeptide levels in a biological sample can be by any techniques known in the art, which include, but are not limited to, radioimmunoassays, competitive-binding assays, Western Blot analysis and enzyme linked immunosorbent assays (ELISAs) and other antibody-based techniques. For example, PGRP-K, PGRP-W, and/or PGRP-C polypeptide expression in tissues can be studied with classical immuno-histological methods (Jalkanen et al., J. Cell. Biol. 101:976–985 (1985); Jalkanen et al., J. Cell. Biol. 105:3087–3096 (1987)).Suitable labels are known in the art and include enzyme labels, such as, Glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

Antibodies

Further polypeptides of the invention relate to antibodies and T-cell antigen receptors (TCR) which immunospecifically bind a polypeptide, polypeptide fragment, or variant of SEQ ID NOs: 2, 4, and/or 6, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdfv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g.,. by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $5\times10^{-3}$ M, $5\times10^{-4}$ M, $5\times10^{-4}$ M, $5\times10^{-5}$ M, $5\times10^{-5}$ M, $5\times10^{-6}$ M, $5\times10^{-6}$ M, $5\times10^{-7}$ M, $5\times10^{-7}$ M, $5\times10^{-8}$ M, $5\times10^{-8}$ M, $5\times10^{-9}$ M, $5\times10^{-9}$ M, $5\times10^{-10}$ M, $5\times10^{-10}$ M, $5\times10^{-11}$ M, $5\times10^{-11}$ M, $5\times10^{-12}$ M, $10^{-12}$ M, $5\times10^{-13}$ M, $5\times10^{-13}$ M, $5\times10^{-14}$ M, $5\times10^{-14}$ M, $5\times10^{-15}$ M, or $5\times10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85 %, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4):1786–1794 (1998); Zhu et al., Cancer Res. 58(15): 3209–3214 (1998); Yoon et al., J. Immunol. 160(7): 3170–3179 (1998); Prat et al, J. Cell. Sci. 111(Pt2):237–247 (1998); Pitard et al., J. Immunol. Methods 205(2):177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al.; Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations), to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples (e.g., Example 16). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, Molecular Immunology 28(4/5) :489–498 (1991); Studnicka et al., Protein Engineering 7(6):805–814 (1994); et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NOs: 2, 4, and/or 6.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio-Techniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRS) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:54454 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as Escherichia coli, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the E. coli expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non- essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5): 155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. Sec, e.g., U.S. Pat. Nos. 5,336,603; 5,622,929; 5,359,046; 5,349,053, 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of SEQ ID NOs: 2, 4, and/or 6 may be fused or conjugated to the above antibody portions to increase the in vivo half life of the polypeptides or for use in immunoassays using methods known in the art. Further, the polypeptides corresponding to SEQ ID NOs: 2, 4, and/or 6 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine-peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g. a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.*, 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-SF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell*, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA; PMSF, aprotinin, sodium vanadate), adding the antibody of interest to the cell lysate, incubating for a period of time (e.g., 14 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives analogs, or nucleic acids, are administered to a human patient for therapy prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $5\times10^{-2}$ M, $5\times10^{-3}$ M, $5\times10^{-3}$ M, $5\times10^{-4}$ M, $5\times10^{-4}$ M, $5\times10^{-5}$ M, $5\times10^{-5}$ M, $5\times10^{-6}$ M, $5\times10^{-6}$ M, $5\times10^{-7}$ M, $5\times10^{-7}$ M, $5\times10^{-8}$ M, $5\times10^{-8}$ M, $5\times10^{-9}$ M, $5\times10^{-9}$ M, $5\times10^{-10}$ M, $5\times10^{-10}$ M, $5\times10^{-11}$ M, $5\times10^{-11}$ M, $5\times10^{-12}$ M, $5\times10^{-12}$ M, $5\times10^{-13}$ M, $5\times10^{-13}$ M, $5\times10^{-14}$ M, $5\times10^{-14}$ M, $5\times10^{-15}$ M, $5\times10^{-15}$ M, $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342:435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition. can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J.Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/g to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell . Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (355), tritium (3H), indium (12In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface- bound recombinant antigens, and a reporter-labeled anti-human antibody for detecting surface-bound anti-antigen antibody.

Formulations

The PGRP-K, PGRP-W, or PGRP-C polypeptide compositions (preferably containing a polypeptide which is a soluble form of the extracellular domain), respectively, will be formulated and dosed in a fashion consistent with good medical practice, taking into account the clinical condition of the individual patient (especially the side effects of treatment with either PGRP-K, PGRP-W, or PGRP-C polypeptide alone), the site of delivery of the PGRP-K, PGRP-W, and/or PGRP-C polypeptide composition, the method of administration, the scheduling of administration, and other factors known to practitioners. The "effective amount" of PGRP-K, PGRP-W, and/or PDRP-C polypeptide for purposes herein is thus determined by such considerations.

As a general proposition, the total pharmaceutically effective amount of PGRP-K, PGRP-W, and/or PGRP-C polypeptide administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the PGRP-K, PGRP-W, or PGRP-C polypeptide is typically administered at a dose rate of about 1 μg/kg/hour to about 50 μg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the PGRP-K, PGRP-W, or PGRP-C of the invention may be administered orally, rectally, parenterally, intracistemally, intravaginally, intraperitoneally, topically (as by powders, ointments, drops or trasdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The PGRP-K, PGRP-W and PGRP-C polypeptides are also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly(2-hydroxyethyl methacrylate) (R. Langer et al., *J. Biomed Mater. Res.* 15:167–277 (1981), and R. Langer, *Chem. Tech.* 12:98–105 (1982)), ethylene vinyl acetate (R. Langer et al., Id.) or poly-D-(−)-3-hydroxybutyric acid (EP 133,988). Sustained-release PGRP-K, PGRP-W, and PGRP-C polypeptide compositions also include liposomally entrapped PGRP-K, PGRP-W, and PGRP-C polypeptides. Liposomes containing PGRP-K, PGRP-W, and/or PGRP-C polypeptides are prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal PGRP-K, PGRP-W, or PGRP-C polypeptide therapy.

For parenteral administration, in one embodiment, the PGRP-K, PGRP-W, and PGRP-C polypeptides are formulated generally by mixing them, respectively, at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting either the PGRP-K, PGRP-W, or PGRP-C polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The PGRP-K, PGRP-W, or PGRP-C polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of PGRP-K, PGRP-W, or PGRP-C polypeptide salts.

PGRP-K, PGRP-W, or PGRP-C polypeptide to be used for therapeutic administration must be sterile. Sterility is readily accomplished by filtration through sterile filtration membranes (e.g., 0.2 micron membranes). Therapeutic PGRP-K, PGRP-W, or PGRP-C polypeptide compositions generally are placed into a container having a sterile access port, for example, an intravenous solution bag or vial having a stopper pierceable by a hypodermic injection needle.

PGRP-K, PGRP-W, or PGRP-C polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous PGRP-K, PGRP-W, or PGRP-C polypeptide solution, and the resulting mixture is lyophilized. The infusion solution is prepared by reconstituting the lyophilized PGRP-K, PGRP-W, or PGRP-C polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Agonists and Antagonists—Assays and Molecules

The invention also provides a method of screening compounds to identify those which enhance or block the action of PGRP-K, PGRP-W, or PGRP-C on cells, such as its interaction with either PGRP-K, PGRP-W, or PGRP-C binding molecules such as receptor molecules. An agonist is a compound which increases the natural biological functions of PGRP-K, PGRP-W, or PGRP-C or which functions in a manner similar to PGRP-K, PGRP-W, or PGRP-C while antagonists decrease or eliminate such functions.

In another aspect of this embodiment the invention provides a method for identifying a receptor protein or other ligand-binding protein which binds specifically to a PGRP-K, PGRP-W, or PGRP-C polypeptide. For example, a cellular compartment, such as a membrane or a preparation thereof, may be prepared from a cell that expresses a molecule that binds PGRP-K, PGRP-W, or PGRP-C. The preparation is incubated with labeled PGRP-K, PGRP-W, or PGRP-C and complexes of PGRP-K, PGRP-W, or PGRP-C, respectively, bound to the receptor or other binding proteins are isolated and characterized according to routine methods known in the art. Alternatively, the PGRP-K, PGRP-W, or PGRP-C polypeptide may be bound to a solid support so that binding molecules solubilized from cells are bound to the column and then eluted and characterized according to routine methods.

In the assay of the invention for agonists or antagonists, a cellular compartments, such as a membrane or a preparation thereof, may be prepared from a cell that expresses a molecule that binds PGRP-K, PGRP-W, or PGRP-C such as a molecule of the immune system, such as a macrophage or a monocyte. The preparation is incubated with labeled PGRP-K, PGRP-W, or PGRP-C in the absence or the presence of a candidate molecule which may be a PGRP-K, PGRP-W, or PGRP-C agonist or antagonist. The ability of the candidate molecule to bind the binding molecule is reflected in decreased binding of the labeled ligand. Molecules which bind gratuitously, i.e., without inducing the effects of PGRP-K, PGRP-W, or PGRP-C on binding the PGRP-K, PGRP-W, or PGRP-C binding molecule, are most likely to be good antagonists. Molecules that bind well and elicit effects that are the same as or closely related to PGRP-K, PGRP-W, or PGRP-C are agonists.

PGRP-K, PGRP-W, or PGRP-C-like effects of potential agonists and antagonists may by measured, for instance, by determining activity of a second messenger system following interaction of the candidate molecule with a cell or appropriate cell preparation, and comparing the effect with that of PGRP-K, PGRP-W, or PGRP-C or molecules that elicit the same effects as PGRP-K, PGRP-W, or PGRP-C. Second messenger systems that may be useful in this regard include but are not limited to AMP guanylate cyclase, ion channel or phosphoinositide hydrolysis second messenger systems.

Another example of an assay for PGRP-K, PGRP-W, or PGRP-C antagonists is a competitive assay that combines PGRP-K, PGRP-W, or PGRP-C and a potential antagonist with membrane-bound receptor molecules or recombinant PGRP-K, PGRP-W, or PGRP-C receptor molecules under appropriate conditions for a competitive inhibition assay. PGRP-K, PGRP-W, or PGRP-C can be labeled, such as by radioactivity, such that the number of PGRP-K, PGRP-W, or PGRP-C molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide. such as a closely related protein or antibody that binds the same sites on a binding molecule, such as a receptor molecule, without inducing PGRP-K, PGRP-W, or PGRP-C induced activities, thereby preventing the action of PGRP-K, PGRP-W, or PGRP-C by excluding PGRP-K, PGRP-W, or PGRP-C from binding.

Other potential antagonists include antisense molecules. Antisense technology can be used to control gene expression through antisense DNA or RNA or through triple-helix formation. Antisense techniques are discussed, for example, in Okano, J. Neurochem. 56: 560 (1991); "Oligodeoxy-nucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). The methods are based on binding of a polynucleotide to a complementary DNA or RNA. For example, the 5' coding portion of a polynucleotide that encodes the PGRP-like domain of one of the polypeptides of the present invention may be used to design an antisense RNA oligonucleotide of from about 10 to 40 base pairs in length. A DNA oligo-nucleotide is designed to be complementary to a region of the gene involved in transcription thereby preventing tran-scription and the production of PGRP-K, PGRP-W, or PGRP-C, respectively. The antisense RNA oligonucleotide hybridizes to the mRNA in vivo and blocks taanslation of the mRNA molecule into either the PGRP-K, PGRP-W, or PGRP-C polypeptide. The oligonucleotides described above can also be delivered to cells such that the antisense RNA or DNA may be expressed in vivo to inhibit production of PGRP-K, PGRP-W, or PGRP-C.

The agonists and antagonists may be employed in a composition with a pharmaceutically acceptable carrier, e.g., as described above.

The antagonists may be employed for instance to inhibit PGRP-K, PGRP-W, or PGRP-C chemotaxis and activation of macrophages and their precursors, and of neutrophils, monocytes, basophils, B lymphocytes and some T-cell subsets, e.g., activated and CD8 cytotoxic T cells and natural killer cells, in certain auto-immune and chronic inflamma-tory and infective diseases. Examples of auto-immune-diseases include multiple sclerosis, and insulin-dependent diabetes. The antagonists may also be employed to treat infectious diseases including silicosis, sarcoidosis, idio-pathic pulmonary fibrosis by preventing the recruitment and activation of mononuclear phagocytes. They may also be employed to treat idiopathic hyper-eosinophilic syndrome by preventing eosinophil production and migration. Endot-oxic shock may also be treated by the antagonists by preventing the migration of macrophages and their produc-tion of the human chemokine polypeptides of the present invention. The antagonists may also be employed for treat-ing atherosclerosis, by preventing monocyte infiltration in the artery wall. The antagonists may also be employed to treat histamine-mediated allergic reactions and immunologi-cal disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated. The antagonists may also be employed to treat chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung. Antagonists may also be employed to treat rheumatoid arthritis by preventing the attraction of monocytes into synovial fluid in the joints of patients. Monocyte influx and activation plays a significant role in the pathogenesis of both degenerative and inflammatory arthropathies. The antago-nists may be employed to interfere with the deleterious cascades attributed primarily to IL-1 and TNF, which pre-vents the biosynthesis of other inflammatory cytokines. In this way, the antagonists may be employed to prevent inflammation. The antagonists may also be employed to inhibit prostaglandin-independent fever induced by chemok-ines. The antagonists may also be employed to treat cases of bone marrow failure, for example, aplastic anemia and myelodysplastic syndrome. The antagonists may also be employed to treat asthma and allergy by preventing eosino-phil accumulation in the lung. The antagonists may also be employed to treat subepithelial basement membrane fibrosis which is a prominent feature of the asthmatic lung.

Antibodies against PGRP-K, PGRP-W, or PGRP-C may be employed to bind to and inhibit PGRP-K, PGRP-W, or PGRP-C activity to treat ARDS, by preventing infiltration of neutrophils into the lung after injury. The antagonists may be employed in a composition with a pharmaceutically accept-able carrier, e.g., as hereinafter described.

Prophylactic and Therapeutic Methods

It is to be understood that although the following discus-sion is specifically directed to human patients, the teachings are also applicable to any animal that expresses PGRP-K, PGRP-W, or PGRP-C.

PGRP-K, PGRP-W, or PGRP-C polypeptides or poly-nucleotides (including PGRP-K, PGRP-W, or PGRP-C fragments, variants, derivatives, and analogs, and PGRP-K, PGRP-W, or PGRP-C agonists and antagonists as described herein) are useful to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, PGRP-K, PGRP-W, or PGRP-C polypeptides or polynucleotides and/or PGRP-K, PGRP-W, or PGRP-C agonists or antagonists may also directly inhibit the infec-tious agent, without necessarily eliciting an immune response.

PGRP-K, PGRP-W, or PGRP-C polypeptides or poly-nucleotides (including PGRP-K, PGRP-W, or PGRP-C fragments, variants, derivatives, and analogs, and PGRP-K, PGRP-W, or PGRP-C agonists and antagonists as described herein) are useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, PGRP-K, PGRP-W, or PGRP-C polynucleotides or polypeptides can be used as a marker or detector of a particular immune system disease or disorder.

Similarly, PGRP-K, PGRP-W, or PGRP-C polypeptides or polynucleotides (including PGRP-K, PGRP-W, or PGRP-C fragments, variants, derivatives, and analogs, and PGRP-K, PGRP-W, or PGRP-C agonists and PGRP-K PGRP-W, or PGRP-C antagonists as described herein) are useful to modulate inflammation. For example, PGRP-K, PGRP-W, or PGRP-C polypeptides. or polynucleotides and/ or PGRP-K, PGRP-W, or PGRP-C agonists and antagonists of the invention may inhibit the proliferation and differentiation of cells involved in an inflammatory response or alternatively may be involved in killing of hematopoietic cells during processes of inflammation or tissue injury. These molecules can be used to treat inflammatory conditions, both chronic and acute conditions, including ischemia-reperfusion injury, arthritis, and/or nephritis. Additionally, these molecules may be used to treat or prevent killing of hematopoietic cells and/or other cells during processes of inflammation or tissue injury.

PGRP-K, PGRP-W, or PGRP-C polypeptides or polynucleotides (including PGRP-K, PGRP-W, or PGRP-C fragments, variants, derivatives, and analogs, and PGRP-K, PGRP-W, or PGRP-C agonists and antagonists as described herein) are useful to treat or detect hyperproliferative disorders, including neoplasms. PGRP-K, PGRP-W, or PGRP-C polypeptides or polynucleotides and/or PGRP-K, PGRP-W, or PGRP-C agonists or antagonists, may inhibit the proliferation of the disorder through direct or indirect interactions. Alternatively, PGRP-K, PGRP-W, or PGRP-C polypeptides or polynucleotides and/or PGRP-K, PGRP-W, or PGRP-C agonists or antagonists may proliferate other cells which can inhibit the hyperproliferative disorder. For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Given the activities modulated by PGRP-K, PGRP-W, or PGRP-C, it is readily apparent that a substantially altered (increased or decreased) level of expression of PGRP-K, PGRP-W, or PGRP-C in an individual compared to the standard or "normal" level produces pathological conditions such as those described above. It will also be appreciated by one of ordinary skill that the PGRP-K, PGRP-W, or PGRP-C agonists of the invention will exert modulating activities on any of its target cells. Therefore, it will be appreciated that conditions caused by a decrease in the standard or normal level of PGRP-K, PGRP-W, or PGRP-C mediated activity in an individual, can be treated by administration of PGRP-K, PGRP-W, or PGRP-C polypeptide or an agonist thereof.

Thus, in one embodiment, the present invention is directed to a method for enhancing (i.e., increasing) PGRP-K, PGRP-W, or PGRP-C mediated activity (e.g., immunity) which involves administering to an individual in need of an increased level of PGRP-K, PGRP-W, or PGRP-C mediated activity, a therapeutically effective amount of PGRP-K, PGRP-W, or PGRP-C polypeptide, fragment, variant, derivative, or analog, or an agonist capable of increasing PGRP-K, PGRP-W, or PGRP-C mediated activity. In specific embodiments, PGRP-K, PGRP-W, or PGRP-C mediated signaling is increased to treat a disease or condition wherein decreased cell survival, secretion, proliferation, migration, and/or differentiation is exhibited.

In another embodiment, the present invention is directed to a method for suppressing (i.e., decreasing) PGRP-K, PGRP-W, or PGRP-C mediated activity (e.g., inflammation), which involves administering to an individual in need of a decreased level of PGRP-K, PGRP-W, or PGRP-C mediated activity, a therapeutically effective amount of PGRP-K, PGRP-W, or PGRP-C polypeptide, fragment, variant, derivative, or analog or an antagonist capable of decreasing PGRP-K, PGRP-W, or PGRP-C mediated activity. In specific embodiments, PGRP-K, PGRP-W, or PGRP-C mediated signaling is decreased to treat a disease or condition wherein increased cell survival, secretion, proliferation, migration and/or differentiation is exhibited.

In addition to treating diseases associated with elevated or decreased levels of PGRP-K, PGRP-W, or PGRP-C mediated activity, the invention encompasses methods of administering PGRP-K, PGRP-W, or PGRP-C agonists or antagonists to elevate or reduce PGRP-K, PGRP-W, or PGRP-C mediated biological activity, respectively.

For treating abnormal conditions related to an underexpression of PGRP-K, PGRP-W, or PGRP-C and its activity, or in which elevated or decreased levels of PGRP-K, PGRP-W, or PGRP-C are desired, several approaches are available. One approach comprises administering to an individual in need of an increased level of PGRP-K, PGRP-W, or PGRP-C mediated activity in the body, a therapeutically effective amount of an isolated PGRP-K, PGRP-W, or PGRP-C polypeptide, fragment, variant, derivative or analog of the invention, or a compound which activates PGRP-K, PGRP-W, or PGRP-C, i.e., an agonist as described above, optionally in combination with a pharmaceutically acceptable carrier. Alternatively, gene therapy may be employed to effect the endogenous production of PGRP-K, PGRP-W, or PGRP-C by the relevant cells in the subject. For example, a polynucleotide of the invention may be engineered for expression in a replication defective retroviral vector using techniques known in the art. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For an overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

Further, treatment can be administered, for example, in the form of gene replacement therapy. Specifically, one or more copies of a PGRP-K, PGRP-W, or PGRP-C nucleotide sequence of the invention that directs the production of a PGRP-K, PGRP-W, or PGRP-C gene product, respectively, exhibiting normal function, may be inserted into the appropriate cells within a patient or animal subject, using vectors which include, but are not limited to, adenovirus, adeno-associated virus, retrovirus and herpesvirus vectors, in addition to other particles that introduce DNA into cells, such as liposomes and gene activated matrices. Because the PGRP-K, PGRP-W, or PGRP-C gene is expressed in epithelial and endothelial tissues, such gene replacement techniques should be capable of delivering PGRP-K, PGRP-W, or PGRP-C gene sequence to these cells within patients, or, alternatively, should involve direct administration of such PGRP-K, PGRP-W, or PGRP-C polynucleotide sequences to the site of the cells in which the PGRP-K, PGRP-W, or PGRP-C gene sequences are to be expressed. Alternatively, targeted homologous recombination can be utilized to correct the defective endogenous PGRP-K, PGRP-W, or PGRP-C gene and/or regulatory sequences thereof (e.g., promoter and enhancer sequences), or alternatively, to "turn on" other dormant PGRP-K, PGRP-W, or PGRP-C activity in the appropriate tissue or cell type.

Additional methods which may be utilized to increase the overall levels of PGRP-K, PGRP-W, or PGRP-C expression and/or PGRP-K, PGRP-W, or PGRP-C activity include the introduction of appropriate PGRP-K, PGRP-W, or PGRP-C-expressing cells, preferably autologous cells, into a patient at positions and in numbers which are sufficient to ameliorate the symptoms of abnormalities in cell growth regulation, cell signaling, and other PGRP-K, PGRP-W, or PGRP-C mediated activities. Such cells may be either recombinant or non-recombinant. Among the cells which can be administered to increase the overall levels of PGRP-K, PGRP-W, or PGRP-C gene expression in a patient are normal cells, which express the PGRP-K, PGRP-W, or PGRP-C gene. Cell-based gene therapy techniques are well known to those skilled in the art, see, e.g., Anderson et al., U.S. Pat. No. 5,399,349; and Mulligan & Wilson, U.S. Pat. No. 5,460,959.

Thus, one embodiment of the invention comprises administering to in individual in need of an increased level of PGRP-K, PGRP-W, or PGRP-C mediated activity a compound that stimulates PGRP-K, -PGRP-W, or PGRP-C mediated activity (agonist), such as for example, an antibody or PGRP-K, PGRP-W, or PGRP-C fragment, variant, derivative or analog of the invention, along with a pharmaceutically acceptable carrier in an amount effective to enhance (i.e., increase) PGRP-K, PGRP-W, or PGRP-C mediated activity.

If the activity of PGRP-K, PGRP-W, or PGRP-C is in excess, several approaches are available to reduce or inhibit PGRP-K, PGRP-W, or PGRP-C activity using molecules derived from the polypeptide and polynucleotide sequences described above. Accordingly, a further aspect of the invention is related to a method for treating an individual in need of a decreased level of PGRP-K, PGRP-W, or PGRP-C mediated activity in the body comprising, administering to such an individual a composition comprising a therapeutically effective amount of a PGRP-K, PGRP-W, or PGRP-C polypeptide, fragment, variant, derivative or analog of the invention which acts as a PGRP-K, PGRP-W, or PGRP-C antagonist or PGRP-K, PGRP-W, or PGRP-C antagonist identified using the methods described herein, optionally, in combination with a pharmaceutically acceptable carrier. Preferably, PGRP-K, PGRP-W, or PGRP-C activity is decreased to treat a disease wherein increased cell survival, secretion, proliferation, migration, and/or differentiation is exhibited. Polypeptides, derivatives, variants and analogs of the invention and other compounds which function as antagonists of PGRP-K, PGRP-W, or PGRP-C can routinely be identified using the assays described infra and other techniques known in the art. Preferred antagonists for use in the present invention are PGRP-K, PGRP-W, or PGRP-C-specific antibodies.

In another approach, PGRP-K, PGRP-W, or PGRP-C activity can be reduced or inhibited by decreasing the level of PGRP-K, PGRP-W, or PGRP-C gene expression, respectively. In one embodiment, this is accomplished through the use of antisense sequences, either internally generated or separately administered (see, for example, O'Connor, J. Neurochem. (1991) 56:560 in Oligodeoxynucleotides as Antisense Inhibitors of Gene Expression, CRC Press, Boca Raton, Fla. (1988). Antisense technology can be used to control gene expression through antisense DNA or RNA or through triple-helix formation. Antisense techniques are discussed, for example, in Okano, J. Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1360 (1991). The methods are based on binding of a polynucleotide to a complementary DNA or RNA. For example, the 5' coding portion of a polynucleotide that encodes a PGRP-K, PGRP-W, or PGRP-C polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the PGRP-K, PGRP-W, or PGRP-C polypeptide. The antisense RNA oligonucleotide hybridizes to the mRNA in vivo and blocks translation of the mRNA molecule into polypeptide.

In one embodiment, the PGRP-K, PGRP-W, or PGRP-C antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the PGRP-K, PGRP-W, or PGRP-C antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding PGRP-K, PGRP-W, or PGRP-C, or fragments thereof, can be by any promoter known in the art to act in vertebrate, preferably human cells. Such promoters can be inducible or constitutive. Such promoters include, but are not limited to, the SV40 early promoter region (Bemoist and Chambon, Nature 29:304–310 (1981), the promoter contained in the 3' long terminal repeat of Rous sarcoma virus (Yamamoto et al., Cell 22:787–797 (1980)), the herpes thymidine promoter (Wagner et al., Proc. Natl. Acad. Sci. U.S.A. 78:1441–1445 (1981)), the regulatory sequences of the metallothionein gene (Brinster et al., Nature 296:3942 (1982)), etc.

The antisense nucleic acids of the invention comprise a sequence complementary to at least a portion of an RNA transcript of a PGRP-K, PGRP-W, or PGRP-C gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded PGRP-K, PGRP-W, or PGRP-C antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a PGRP-K, PGRP-W, or PGRP-C RNA it may contain and still form a stable duplex (or triplex as the case may be), respectively. One skilled in the art can ascertain a tolerable degree of mismatch by use of standard procedures to determine the melting point of the hybridized complex.

Potential PGRP-K, PGRP-W, or PGRP-C antagonists according to the invention also include catalytic RNA, or a ribozyme (See, e.g., PCT International Publication WO 90/11364, published Oct. 4, 1990; Sarver et al., Science 247:1222–1225 (1990). While ribozymes that cleave mRNA at site specific recognition sequences can be used to destroy PGRP-K, PGRP-W, or PGRP-C mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequences of PGRP-K, PGRP-W, or PGRP-C (FIGS. 1A–C; SEQ ID NO:1). Preferably, the ribozyme is engineered so that the cleavage recognition site is located near the 5' end of either the PGRP-K, PGRP-W, or PGRP-C mRNA; i.e., to increase efficiency and minimize the intracellular accumulation of non-functional mRNA transcripts. DNA constructs encoding the ribozyme may be introduced into the cell in the same manner as described above for the introduction of antisense encoding DNA. Since ribozymes, unlike antisense molecules are catalytic, a lower intracellular concentration is required for efficiency.

Endogenous PGRP-K, PGRP-W, or PGRP-P gene expression can also be reduced by inactivating or "knocking out" the PGRP-K, PGRP-W, or PGRP-C gene, respectively, or its promoter using targeted homologous recombination (e.g., see Smithies et al., Nature 317:330–234 (1985); Thomas et al., Cell 51:503–512 (1987); Thompson et al., Cell 5:313–321 (1989); each of which is incorporated by reference herein in its entirety). Such approach can be adapted for use in humans provided the recombinant DNA constructs are directly administered or targeted to the required site in vivo using appropriate viral vectors.

Alternatively, endogenous PGRP-K, PGRP-W, or PGRP-C gene expression can be reduced by targeted deoxyribonucleotide sequences complementary to the regulatory region of the PGRP-K, PGRP-W, or PGRP-C gene (i.e., the PGRP-K, PGRP-W, or PGRP-C promoters and/or enhancers), respectively, to form triple helical structures that prevent transcription of the PGRP-K, PGRP-W, or PGRP-C genes in target cells in the body, see generally, Helene et al., Ann, N.Y. Acad. Sci. 660:27–36 (1992); Helene, C., Anticancer Drug Des., 6(6):569–584 (1991); and Maher, L. J., Bioassays 14(12):807–815 (1992)).

Thus, one embodiment of the invention comprises administering to an individual in need of a decreased level of PGRP-K, PGRP-W, or PGRP-C mediated activity, a PGRP-K, PGRP-W, or PGRP-C inhibitor compound (antagonist), such as for example, an antibody or PGRP-K, PGRP-W, or PGRP-C fragment, variant, derivative or analog of the invention, along with a pharmaceutically acceptable carrier in an amount effective to suppress (i.e., lower) PGRP-K, PGRP-W, or PGRP-C mediated activity.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a PGRP-K, PGRP-W, and/or PGRP-C protein gene. This can be accomplished using a variety of well known techniques and libraries, which generally are available commercially. The genonic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1

Isolation of PGRP-K, PGRP-W, and/or PGRP-C cDNA Clone(s) From the Deposited Sample(s)

The cDNA for PGRP-K (ATCC Accession No: 203564) is inserted into the Sal I and Not I multiple cloning site of pCMVSport 2.0 (Life Technologies). pCMVSport 2.0 contains an ampicillin resistance gene and may be transformed into *E. coli* strain DH10B, available from Life Technologies. (See, for instance, Gruber, C. E., et al., Focus 15:59- (1993).)

The cDNA for PGRP-W (ATCC Accession No: 203563) is inserted into the Sal I and Not I multiple cloning site of pCMVSport 3.0 (Life Technologies). pCMVSport 3.0 contains an ampicillin resistance gene and may be transformed into *E. coli* strain DH10B, available from Life Technologies. (See, for instance, Gruber, C. E., et al., Focus 15:59- (1993).)

The cDNA for PGRP-C (ATCC Accession No: 209683) is inserted into the EcoRI and Xho I multiple cloning site of Uni-Zap XR (Stratagene). Uni-Zap XR contains an ampicillin resistance gene and may be transformed into *E. coli* strain DH10B, available from Life Technologies. (See, for instance, Gruber, C. E., et al., Focus 15:59- (1993).) Two approaches can be used to isolate either PGRP-K, PGRP-W, and/or PGRP-C from the deposited sample. First, a specific polynucleotide of SEQ ID NO:1, SEQ ID NO:3, and SEQ ID NO:5, respectively, with 30–40 nucleotides is synthesized using an Applied Biosystems DNA synthesizer according to the sequence reported. The oligonucleotide is labeled, for instance, with $^{32}$P-g-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host (such as XL-1

Blue (Stratagene)) using techniques known to those of skill in the art, such as those provided by the vector supplier or in related publications or patents. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of either the SEQ ID NO:1, SEQ ID NO:3, or SEQ ID NO:5, respectively, (i.e., within the region of SEQ ID NO:1 bounded by the 5' NT and the 3' NT of the clone) are synthesized and used to amplify the PGRP-K, PGRP-W, and/or PGRP-C cDNAs using the deposited cDNA plasmids as template. The polymerase chain reaction is carried out under routine conditions, for instance, in 25 ul of reaction mixture with 0.5 ug of the above cDNA template. A convenient reaction mixture is 1.5–5 mM $MgCl_2$, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of either the PGRP-K, PGRP-W, or PGRP-C genes which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., Nucleic Acids Res. 21(7):1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of either the PGRP-K, PGRP-W, or PGRP-C gene of interest is used to PCR amplify the 5' portion of the PGRP-K, PGRP-W, or PGRP-C full-length gene, respectively. This amplified product may then be sequenced and used to generate the full length gene.

This above method starts with total RNA isolated from the desired source, although poly-A+ RNA can be used The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the PGRP-K, PGRP-W, or PGRP-C gene, respectively.

Alternatively, a genomic clone comprising the human PGRP-K, PGRP-W, or PGRP-C coding exons can be isolated by screening a human genomic library as discussed infra. Once positive clones have been identified, the DNA inserts contained in the genomic clone can be isolated, and the DNA sequenced. Once the DNA sequence has been determined, the utilization of a number of computer-based DNA sequence analysis programs, such as, for example, BLAST and GRAIL, will allow the identification of the coding exons and the non-coding introns associated with either the PGRP-K, PGRP-W, or PGRP-C gene, respectively, and hence the identification of any 5' portion of the PGRP-K, PGRP-W, or PGRP-C full-length gene which may not have been previously present in the deposited clone.

Example 2

Isolation of PGRP-K, PGRP-W, or PGRP-C Genomic Clones

A human genomic P1 library (Genomic Systems, Inc.) is screened by PCR using primers selected for the cDNA sequences corresponding to SEQ ID NO:1, SEQ ID NO:3, or SEQ ID NO:5, according to the method described in Example 1. (See also, Sambrook.)

Example 3

Chromosomal Mapping of PGRP-K, PGRP-W, or PGRP-C

An oligonucleotide primer set is designed according to the sequence at the 5' end of SEQ ID NO:1, SEQ ID NO:3, or SEQ ID NO:5. This primer preferably spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 4

Bacterial Expression of PGRP-K, PGRP-W, or PGRP-C

PGRP-K, PGRP-W, or PGRP-C polynucleotides encoding PGRP-K, PGRP-W, or PGRP-C polypeptides, respectively, of the invention are amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as Sal I and Not I, at the 5' end of the primers in order to clone the amplified product into the expression vector. For example, Sal I and Not I correspond to the restriction enzyme sites on the bacterial expression vector pQE-9 (Qiagen, Inc., Chatsworth, Calif.). This plasmid vector encodes antibiotic resistance ($Amp^r$), a bacterial origin of replication (ori), an IPTG-regulatable promoter/operator (P/O), a ribosome binding site (RBS), a 6-histidine tag (6-His), and restriction enzyme cloning sites.

To clone either the PGRP-K, PGRP-W, or PGRP-C polypeptide in a bacterial vector, a 5' primer including a restriction site shared by the bacterial vector of interest, and including a number of nucleotides of the amino terminal coding sequence of the sequence of interest, is designed and synthesized. Likewise, a 3' primer including a restriction site shared by the bacterial vector of interest, and including nucleotides complementary to the 3' end of the coding sequence of the sequence of interest, is designed and synthesized. It would be obvious to one skilled in the art as to how to design the primers of interest. The primers are synthesized using an Applied Biosystems DNA synthesizer according to the sequence reported.

For example, specifically, to clone the PGRP-K polypeptide in a bacterial vector, the 5' primer is easily designed by one skilled in the art to clone the PGRP-K polypeptide in a bacterial vector, the 5' primer has the sequence 5' GCA GCACATATGGATTCCTCCTGGA ACA AAA CAC AAG CTAAAC 3' (SEQ ID NO: 8) containing the underlined NdeI restriction site followed by a number of nucleotides of the amino terminal coding sequence of the full-length PGRP-K sequence in SEQ ID NO:1. One of ordinary skill in the art would appreciate, of course, that the point in the protein coding sequence where the 5' primer begins may be varied to amplify a DNA segment encoding any desired portion of the complete PGRP-K protein shorter or longer than the full-length form of the protein. The 3' primer has the sequence 5' GCAGCAGGTACCTTAGTGTTTGAAATG AGGCCAGGTGCTGATGATG 3' (SEQ ID NO: 9) containing the underlined Asp718 restriction site followed by a number of nucleotides complementary to the 3' end of the coding sequence of the PGRP-K DNA sequence of SEQ ID NO:1. PGRP-W and PGRP-C can also be cloned into a bacterial vector using primers and restriction sites specific to those proteins.

The pQE-9 vector is digested with NdeI and Asp718 and the amplified fragment (of either PGRP-K, PGRP-W, or PGRP-C) is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, which expresses the lacI repressor and also confers kanamycin resistance (Kan'). Transformants are identified by their ability to grow on LB plates and ampiclilin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g).

In addition to the above expression vector, the present invention further includes an expression vector comprising phage operator and promoter elements operatively linked to a PGRP-K, PGRP-W, or PGRP-C polynucleotide, called pHE4a. (ATCC Accession Number 209645, deposited Feb. 25, 1998.) This vector contains: 1) a neomycinphosphotransferase gene as a selection marker, 2) an *E. coli* origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHE4a by restricting the vector with NdeI and KpnI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 5

Cloning and Expression of PGRP-K, PGRP-W, or PGRP-C in a Baculovirus Expression System In this example, the plasmid shuttle vector pA2 is used to insert either the PGRP-K, PGRP-W, or PGRP-C polynucleotide into a baculovirus to express PGRP-K, PGRP-W, or PGRP-C, respectively. This expression vector contains the strong polyhedrin promoter of the *Autographa californica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that expresses the cloned PGRP-K, PGRP-W, or PGRP-C polynucleotide, respectively.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the PGRP-K, PGRP-W, or PGRP-C cDNA sequence contained in the deposited clones, including the AUG initiation codon and any naturally associated leader sequence, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

To clone either the PGRP-K, PGRP-W, or PGRP-C polypeptide in the baculovirus vector of interest, a 5' primer including a restriction site shared by the baculovirus vector of interest, an efficient signal for initiation of translation in eukaryotic cells (Kozak, M., *J. Mol. Biol.* 196:947–950

(1987)), and including a number of nucleotides of the amino terminal coding sequence of the sequence of interest, is designed and synthesized. Likewise, a 3' primer including a restriction site shared by the bacterial vector of interest, and including nucleotides complementary to the 3' sequence of the sequence of interest, is designed and synthesized. It would be obvious to one skilled in the art as to how to design the primers of interest. The primers are synthesized using an Applied Biosystems DNA synthesizer according to the sequence reported.

For example, specifically, the cDNA sequence encoding the PGRP-K protein in the deposited clone shown in SEQ ID NO:1, is amplified using PCR oligonucleotide primers corresponding to the 5' and 3' sequences of the gene. The 5' primer has the sequence 5' GCAGCA GGATCCGCCATCATGGGGACGCTGCCATGGCTTCTT GCCTTC 3' (SEQ ID NO: 10) containing the BamHI restriction enzyme site, an efficient signal for initiation of translation in eukaryotic cells (Kozak, M., *J. Mol. Biol.* 196:947–950 (1987)), followed by a number of nucleotides of the sequence of the PGRP-K protein shown in FIGS. 1A–B. The 3' primer has the sequence 5' GCAGCA GGTACCTTATTGATATCCAATGTCACAAAAGTTCCGT GTG 3' (SEQ ID NO: 11) containing the KpnI restriction site followed by a number of nucleotides complementary to the 3' sequence in FIGS. 1A–B.

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB 101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transfected with 1.0 ug of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One ug of BaculoGold™ virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of $^{35}$S-methionine and 5 uCi $^{35}$S-cysteine (available from Amersham) are added. The cells are further incubated for 16 hours and then are harvested by centrifugation. The proteins are analyzed by SDS-PAGE followed by autoradiography (if radiolabeled).

Microsequencing of the amino acid sequence of the amino terminus of purified protein may be used to determine the amino terminal sequence of the produced PGRP-K, PGRP-W, or PGRP-C polypeptide.

Example 6

Expression of PGRP-K, PGRP-W, or PGRP-C in Mammalian Cells

PGRP-K, PGRP-W, or PGRP-C polypeptides can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2DHFR (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, PGRP-K, PGRP-W, or PGRP-C polypeptides can be expressed in stable cell lines containing either the PGRP-K, PGRP-W, or PGRP-C polynucleotide integrated into a chromosome, respectively. The cotransfection with a selectable marker such as DHFR, gpt, neomycin, hygromycin allows the identification and isolation of the transfected cells.

The transfected PGRP-K, PGRP-W, or PGRP-C gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357–1370 (1978); Hamlin, J. L. and, Ma C., Biochem. et Biophys. Acta, 1097:107–143 (1990); Page, M. J. and Sydenham M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-DHFR (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985).) Multiple cloning sites, e.g., with the restriction enzyme cleavage sites BamHI, Xbal and Asp718, facilitate the cloning of either PGRP-K, PGRP-W, or PGRP-C. The vectors also contain the 3' intron, the polyadenylation and termination signal of the rat preproinsulin gene, and the mouse DHFR gene under control of the SV40 early promoter.

Specifically, the plasmid pC4 is digested with BamHI and KpnI and then dephosphorylated using calf intestinal phosphates by procedures known in the art. The vector is then isolated from a 1% agarose gel.

The cDNA sequence encoding either the PGRP-K, PGRP-W, or PGRP-C protein in the respective deposited clone is amplified using PCR oligonucleotide primers corresponding to the 5' and 3' sequences of the gene. The 5' primer sequence contains an appropriate restriction site, an efficient signal for initiation of translation in eukaryotic cells (Kozak, M., J. Mol. Biol. 196:947–950 (1987)), followed by a number of nucleotides of the sequence of the PGRP-K, PGRP-W, or PGRP-C sequence. The 3' primer sequence contains an appropriate restriction site followed by a number of nucleotides complementary to the 3' sequence of the PGRP-K, PGRP-W, or PGRP-C sequence.

For example, specifically, the PGRP-K 5' primer has the sequence 5' GCAGCAGGATCCGCCATCATG GGGACG CTGCCATGGCTTCTTGCCTTC 3' (SEQ ID NO: 12) containing the BamHI restriction enzyme site, an efficient signal for initiation of translation in eukaryotic cells (Kozak, M.,J. Mol. Biol. 196:947–950 (1987)), followed by a number of nucleotides of the sequence of the PGRP-K protein shown in FIGS. 1A–B. In this embodiment, the 3' primer has the sequence. 5' GCAGCAGGTACCTTATTGATATCCAAT GTCACAAAAGTTCCGTGTG 3' (SEQ ID NO: 13) containing the KpnI restriction site followed by a number of nucleotides complementary to the 3' sequence in FIGS. 1A–B. It would be obvious to one skilled in the art as to how to design the primers of interest. The primers are synthesized using an Applied Biosystems DNA synthesizer according to the sequence reported.

If a naturally occurring signal sequence is used to produce a secreted protein, the vector does not need a second signal peptide. Alternatively, if a naturally occurring signal sequence is not used, the vector can be modified to include a heterologous signal sequence in an effort to secrete the protein from the cell. (See, e.g., WO 96/34891.)

The amplified fragment is then digested with the BamHI and KpnI and purified on a 1% agarose gel using a commercially available kit ("Geneclean," BIO 101 Inc., La Jolla, Calif.). The isolated fragment and the dephosphorylated vector are then ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary cells lacking an active DHFR gene is used for transfection. Five μg of the expression plasmid pC4 is cotransfected with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MN supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100–200 uM. Expression of EITBER PGRP-K, PGRP-W, OR PGRP-C is analyzed, for instance, by SDS-PAGE and Western blot or by reversed phase HPLC analysis.

Example 7

Construction of N-Terminal and/or C-Terminal Deletion Mutants

The following general approach may be used to clone a N-terminal or C-terminal deletion PGRP-K, PGRP-W, or PGRP-C deletion mutant. Generally, two oligonucleotide primers of about 15–25 nucleotides are derived from the desired 5' and 3' positions of a polynucleotide of SEQ ID NO:1. The 5' and 3' positions of the primers are determined based on the desired PGRP-K, PGRP-W, or PGRP-C polynucleotide fragment. An initiation and stop codon are added to the 5' and 3' primers respectively, if necessary, to express the PGRP-K, PGRP-W, or PGRP-C polypeptide fragment encoded by the polynucleotide fragment. Preferred PGRP-K, PGRP-W, or PGRP-C polynucleotide fragments are those encoding the N-terminal and C-terminal deletion mutants disclosed above in the "Polynucleotide and Polypeptide Fragments" section of the Specification.

Additional nucleotides containing restriction sites to facilitate cloning of the PGRP-K, PGRP-W, or PGRP-C polynucleotide fragment in a desired vector may also be added to the 5' and 3' primer sequences. The PGRP-K, PGRP-W, or PGRP-C polynucleotide fragment is amplified from genomic DNA or from the deposited cDNA clone using the appropriate PCR oligonucleotide primers and conditions discussed herein or known in the art. The PGRP-K, PGRP-W, or PGRP-C polypeptide fragments encoded by the PGRP-K, PGRP-W, or PGRP-C polynucleotide fragments, respectively, of the present invention may be expressed and purified in the same general manner as the full length polypeptides, although routine modifications may be necessary due to the differences in chemical and physical properties between a particular fragment and full length polypeptide.

As a means of exemplifying but not limiting the present invention, the polynucleotide encoding the PGRP-K polypeptide fragment Met-1 to Ile-155 is amplified and cloned as follows: A 5' primer is generated comprising a restriction enzyme site followed by an initiation codon in frame with the polynucleotide sequence encoding the N-terminal portion of the polypeptide fragment beginning with Met-1. A complementary 3' primer is generated comprising a restriction enzyme site followed by a stop codon in frame with the polynucleotide sequence encoding C-terminal portion of the PGRP-K polypeptide fragment ending with Ile-155.

The amplified polynucleotide fragment and the expression vector are digested with restriction enzymes which recognize the sites in the primers. The digested polynucleotides are then ligated together. The PGRP-K polynucleotide fragment is inserted into the restricted expression vector, preferably in a manner which places the PGRP-K polypeptide fragment coding region downstream from the promoter. The ligation mixture is transformed into competent *E. coli* cells using standard. procedures and as described in the Examples herein. Plasmid DNA is isolated from resistant colonies and the identity of the cloned DNA confirmed by restriction analysis, PCR and DNA sequencing.

Example 8

Protein Fusions of PGRP-K, PGRP-W, or PGRP-C

PGRP-K, PGRP-W, or PGRP-C polypeptides are preferably fused to other proteins. These fusion proteins can be used for a variety of applications. For example, fusion of PGRP-K, PGRP-W, or PGRP-C polypeptides to His-tag, HA-tag, protein A, IgG domains, and maltose binding protein facilitates purification. (See Example 5; see also EP A 394,827; Traunecker, et al., Nature 331:84–86 (1988).) Similarly, fusion to IgG-1, IgG-3, and albumin increases the halflife time in vivo. Nuclear localization signals fused to PGRP-K, PGRP-W, or PGRP-C polypeptides can target the protein(s) to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and the PGRP-K, PGRP-W, or PGRP-C polynucleotide, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)
Human IgG Fc Region:

GGGATCCGGAGCCCAAATCTTCTGACAAAACTC
ACACATGCCCACCGTGCCCAGCACCTGAAT
TCGAGGGTGCACCGTCAGTCTTCCTCTTCC
CCCCAAAACCCAAGGACACCCTCATGATCT
CCCGGACTCCTGAGGTCACATGCGTGGTGG
TGGACGTAAGCCACGAAGACCCTGAGGTCA
AGTTCAACTGGTACGTGGACGGCGTGGAGG
TGCATAATGCCAAGACAAAGCCGCGGGAGG
AGCAGTACAACAGCACGTACCGTGTGGTCA
GCGTCCTCACCGTCCTGCACCAGGACTGGC
TGAATGGCAAGGAGTACAAGTGCAAGGTCT
CCAACAAAGCCCTCCCAACCCCCATCGAGA
AAACCATCTCCAAAGCCAAAGGGCAGCCCC
GAGAACCACAGGTGTACACCCTGCCCCCAT
CCCGGGATGAGCTGACCAAGAACCAGGTCA
GCCTGACCTGCCTGGTCAAAGGCTTCTATC
CAAGCGACATCGCCGTGGAGTGGGAGAGCA
ATGGGCAGCCGGAGAACAACTACAAGACCA
CGCCTCCCGTGCTGGACTCCGACGGCTCCT
TCTTCCTCTACAGCAAGCTCACCGTGGACA
AGAGCAGGTGGCAGCAGGGGAACGTCTTCT
CATGCTCCGTGATGCATGAGGCTCTGCACA
ACCACTACACGCAGAAGAGCCTCTCCCTGT
CTCCGGGTAAATGAGTGCGACGGCCGCGAC
TCTAGAGGAT (SEQ ID NO:14)

Example 9

Production of an Antibody

The antibodies of the present invention can be prepared by a variety of methods. (See, Current Protocols, Chapter 2.) For example, cells expressing PGRP-K, PGRP-W, or PGRP-C will be administered to an animal to induce the production of sera containing polyclonal antibodies. In a preferred method, a preparation of PGRP-K, PGRP-W, or PGRP-C protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with the PGRP-K, PGRP-W, or PGRP-C polypeptide or, more preferably, with a secreted PGRP-K, PGRP-W, or PGRP-C polypeptide-expressing cell. Such cells may be cultured in any suitable tissue culture medium; however, it is preferable to culture cells in Earle's modified Eagle's medium supplemented with 10% fetal bovine serum (inactivated at about 56 degree C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225–232 (1981).) The hybridoma cells obtained through such a selection are then assayed to identify clones which secrete antibodies capable of binding the PGRP-K, PGRP-W, or PGRP-C polypeptide, respectively.

Alternatively, additional antibodies capable of binding to the PGRP-K, PGRP-W, or PGRP-C polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the PGRP-K, PGRP-W, or PGRP-C specific antibody can be blocked by PGRP-K, PGRP-W, or PGRP-C, respectively. Such antibodies comprise anti-idiotypic antibodies to the PGRP-K, PGRP-W, or PGRP-C specific antibody and can be used to immunize an animal to induce formation of further PGRP-K, PGRP-W, or PGRP-C specific antibodies, respectively.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted PGRP-K, PGRP-W, or PGRP-C protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., Bio-Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 10

Method of Detecting Abnormal Levels of PGRP-K, PGRP-W, or PGRP-C in a Biological Sample PGRP-K, PGRP-W, or PGRP-C polypeptides can be detected in a biological sample, and if an increased or decreased level of PGRP-K, PGRP-W, or PGRP-C is detected, the respective polypeptide is a marker for a particular phenotype. Methods of detection are numerous, and thus, it is understood that one skilled in the art can modify the following assay to fit their particular needs.

For example, antibody-sandwich ELISAs are used to detect PGRP-K, PGRP-W, or PGRP-C in a sample, preferably a biological sample. Wells of a microtiter plate are coated with specific antibodies to PGRP-K, PGRP-W, or PGRP-C, respectively, at a final concentration of 0.2 to 10 ug/ml. The antibodies are either monoclonal or polyclonal and are produced by the method described in Example 11. The wells are blocked so that non-specific binding of PGRP-K, PGRP-W, or PGRP-C to their respective well is reduced.

The coated wells are then incubated for >2 hours at RT with a sample containing PGRP-K, PGRP-W, or PGRP-C. Preferably, serial dilutions of the sample should be used to validate results. The plates are then washed three times with deionized or distilled water to remove unbounded PGRP-K, PGRP-W, or PGRP-C.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot the PGRP-K, PGRP-W, or PGRP-C polypeptide concentration on the X-axis (log scale) and fluorescence or absorbance of the Y-axis (linear scale). Interpolate the concentration of PGRP-K, PGRP-W, or PGRP-C in the sample using the standard curve.

Example 11

Formulating a Polypeptide

The PGRP-K, PGRP-W, or PGRP-C composition will be formulated and dosed in a fashion consistent with good medical practice, taking into account the clinical condition of the individual patient (especially the side effects of treatment with either the PGRP-K, PGRP-W, or PGRP-C polypeptide alone), the site of delivery, the method of administration, the scheduling of administration, and other factors known to practitioners. The "effective amount" for purposes herein is thus determined by such considerations.

As a general proposition, the total pharmaceutically effective amount of PGRP-K, PGRP-W, or PGRP-C administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, PGRP-K, PGRP-W, or PGRP-C is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing PGRP-K, PGRP-W, or PGRP-C are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

PGRP-K, PGRP-W, or PGRP-C is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547–556 (1983)), poly (2- hydroxyethyl methacrylate) (R. Langer et al., J. Biomed. Mater. Res. 15:167–277 (1981), and R. Langer, Chem. Tech. 12:98–105 (1982)), ethylene vinyl acetate (R. Langer et al.) or poly-D-(-)-3-hydroxybutyric acid (EP 133,988). Sustained-release compositions also include liposomally entrapped PGRP-K, PGRP-W, or PGRP-C polypeptides. Liposomes containing either the PGRP-K, PGRP-W, or PGRP-C are prepared by methods known per se: DE 3,218,121; Epstein et al., Proc. Natl. Acad. Sci. USA 82:3688–3692 (1985); Hwang et al., Proc. Natl. Acad. Sci. USA 77:40304034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, PGRP-K, PGRP-W, or PGRP-C is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting either PGRP-K, PGRP-W, or PGRP-C uniformly and intimately with liquid carriers or finely divided solid carriers, or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

PGRP-K, PGRP-W, or PGRP-C is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

PGRP-K, PGRP-W, or PGRP-C used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

PGRP-K, PGRP-W, or PGRP-C polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous PGRP-K, PGRP-W, or PGRP-C polypeptide solution, respectively, and the resulting mixture is lyophilized. The infusion solution is prepared by reconstituting the lyophilized PGRP-K, PGRP-W, or PGRP-C polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, PGRP-K, PGRP-W, or PGRP-C may be employed in conjunction with other therapeutic compounds.

Example 12

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) PGRP-K, PGRP-W, or PGRP-C sequences into an animal to increase or decrease the expression of the PGRP-K, PGRP-W, or PGRP-C polypeptide, respectively. The PGRP-K, PGRP-W, or PGRP-C polynucleotide may be operatively linked to a promoter or any other genetic elements necessary for the expression of either the PGRP-K, PGRP-W, or PGRP-C polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al. (1997) Cardiovasc. Res. 35(3):470–479, Chao J et al. (1997) Pharmacol. Res. 35(6):517–522, Wolff J. A. (1997) Neuromuscul. Disord. 7(5):314–318, Schwartz B. et al. (1996) Gene Ther. 3(5):405–411, Tsurumi Y. et al. (1996) Circulation 94(12):3281–3290 (incorporated herein by reference).

The PGRP-K, PGRP-W, or PGRP-C polynucleotide constructs may be delivered by any method that delivers injectable materials to the cells of an animal, such as, injection into the interstitial space of tissues (heart, muscle, skin, lung, liver, intestine and the like). The PGRP-K, PGRP-W, or PGRP-C polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the PGRP-K, PGRP-W, or PGRP-C polynucleotides may also be delivered in liposome formulations (such as those taught in Felgner P. L. et al. (1995) Ann. NY Acad. Sci. 772:126–139 and Abdallah B. et al. (1995) Biol. Cell 85(1):1–7) which can be prepared by methods well known to those skilled in the art.

The PGRP-K, PGRP-W, or PGRP-C polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The PGRP-K, PGRP-W, or. PGRP-C polynucleotide constructs can be delivered to the interstitial space of tissues within the an animal, including of pancreas, kidney, muscle, skeletal muscle, skin, brain, lung, liver, spleen, bone marrow, thymus, heart, lymph, blood, bone, cartilage, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked PGRP-K, PGRP-W, or PGRP-C polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked PGRP-K, PGRP-W, or PGRP-C polynucleotide constructs can be delivered to arteries during angioplasty by the catheter used in the procedure.

The dose response effects of injected PGRP-K, PGRP-W, or PGRP-C polynucleotide in muscle in vivo is determined as follows. Suitable PGRP-K, PGRP-W, or PGRP-C template DNA for production of mRNA coding for PGRP-K, PGRP-W, or PGRP-C polypeptides, respectively, is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The PGRP-K, PGRP-W, or PGRP-C template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for PGRP-K, PGRP-W, or PGRP-C protein expression. A time course for PGRP-K, PGRP-W, or PGRP-C protein expression may be done in a similar fashion except that quadriceps from different mice are harvested at different times. Persistence of PGRP-K, PGRP-W, or PGRP-C DNA in muscle following injection may be determined by Southern blot analysis after preparing total cellular DNA and HIRT supernatants from injected and control mice. The results of the above experimentation in mice will be used to extrapolate proper dosages and other treatment parameters in humans and other animals using PGRP-K, PGRP-W, or PGRP-C naked DNA.

Example 13

Peptidoglycan Binding Assay

Insoluble peptidoglycan is prepared from *Micrococcus luteus* as has been described in the art (Araki, Y., Nakatani, T., Nakayama, K. and Ito, E., 1972, J. Biol. Chem., 247:6312–632).

The peptidoglycan binding assay is performed by incubating 0.32 mgs of peptidoglycan in 280 uls of 10 mM maleate buffer, pH 6.5/0.15 M NaCl with 3–6 ugs of a PGRP in 40 uls of 1 M imidazole/0.5 M NaCl/20 mM Tris-HCl, pH 7.9, for 30 min. at 4° C. One-sixteenth of the supernatant and of the pellet was removed for analysis. The protein was separated for the peptidoglycan by boiling in 2% SDS/PAGE loading buffer, subjected to electrophoresis on an SDS/15% polyacrylamide gel, and stained with Coomassie brilliant blue.

It can be appreciated by those skilled in the art that the above assay may be altered and/or refined to a degree to enhance visualization of the binding, while essentially maintaining the general scheme of the assay. Further peptidoglycan binding assays are described by Yoshida et al., JBC, 271 (23): 13854 (1996), which is incorporated in its entirety by reference herein by reference.

Example 14

Measurement of Apoptosis Ability of PGRP-K, PGRP-W, or PGRP-C

In a first incubation step, anti-histone antibody is fixed adsorptively on the wall of a microtiter plate module. Subsequently, non-specific binding sites on the wall are saturated by treatment with incubation buffer (e.g., blocking solution). During the second incubation step, the nucleosomes contained in the appropriate cell (e.g., WEHI 164 cells) sample treated with the PGRP-K, PGRP-W, or PGRP-C bind via their histone components to the immobilized anti-histone antibody. In the third incubation step, anti-DNA-peroxidase reacts with the DNA-part of the nucleosomes. After removal of all unbound peroxidase conjugate by a washing step, the amount of peroxidase retained in the immunocomplex is determined photometrically with ABTS (2,2'-azino-di-[3-ethylbenzthiazoline sulfonate]), as a substrate. Anti-histone antibody reacts with the histones H1, H2A, H2B, H3 and H4 from the sample. Anti-DNA POD antibody binds to single- and double-stranded DNA. Therefore, the ELISA allows the detection on mono- and oligonucleosomes and may be applied to measure apoptotic cell death. The level of cell death is measured by the amount of cytoplasmic histone-associated DNA fragments which are indicated as the absorbance A405 nm/A490. (See Boehringer mannheim Catalogue, 0990 C 93 2 1541170).

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference.

Moreover, the sequence submitted herewith in paper and computer readable form are herein incorporated by reference in their entireties.

What is claimed is:

1. An isolated protein comprising amino acid residues 52 to 135 of SEQ ID NO:4.

2. The isolated protein of claim 1 which comprises amino acid residues 18 to 368 of SEQ ID NO:4.

3. The isolated protein of claim 1 which comprises amino acid residues 2 to 368 of SEQ ID NO:4.

4. The isolated protein of claim 1 which comprises amino acid residues 1 to 368 of SEQ ID NO:4.

5. The protein of claim 1 which comprises a heterologous polypeptide sequence.

6. A composition comprising the protein of claim 1 and a pharmaceutically acceptable carrier.

7. An isolated protein produced by the method comprising:
   (a) expressing the protein of claim 1 by a cell; and
   (b) recovering said protein.

8. An isolated protein comprising the amino acid sequence of the secreted portion of the polypeptide encoded by the cDNA contained in ATCC Deposit No. 203563.

9. The isolated protein of claim 8 which comprises the amino acid sequence of the complete polypeptide encoded by the cDNA contained in ATCC Deposit No. 203563, excepting the N-terminal methionine.

10. The isolated protein of claim 8 which comprises the amino acid sequence of the complete polypeptide encoded by the cDNA contained in ATCC Deposit No. 203563.

11. The protein of claim 8 which comprises a heterologous polypeptide sequence.

12. A composition comprising the protein of claim 8 and a pharmaceutically acceptable carrier.

13. An isolated protein produced by the method comprising:
   (a) expressing the protein of claim 8 by a cell; and
   (b) recovering said protein.

14. An isolated protein comprising a polypeptide sequence which is at least 90% identical to amino acid residues 18 to 368 of SEQ ID NO:4, wherein said isolated protein possesses peptidoglycan binding activity.

15. The isolated protein of claim 14 wherein said polypeptide sequence is at least 90% identical to amino acid residues 1 to 368 of SEQ ID NO:4.

16. The isolated protein of claim 14 wherein said polypeptide sequence is at least 95% identical to amino acid residues 18 to 368 of SEQ ID NO:4.

17. The isolated protein of claim 14 wherein said polypeptide sequence is at least 95% identical to amino acid residues 1 to 368 of SEQ ID NO:4.

18. The protein of claim 14 which comprises a heterologous polypeptide sequence.

19. A composition comprising the protein of claim 14 and a pharmaceutically acceptable carrier.

20. An isolated protein produced by the method comprising:
   (a) expressing the protein of claim 14 by a cell; and
   (b) recovering said protein.

21. An isolated protein comprising a polypeptide sequence which is at least 90% identical to amino acid residues 52 to 135 of SEQ ID NO:4, wherein said isolated protein possesses peptidoglycan binding activity.

22. The isolated protein of claim 21 wherein said polypeptide sequence is at least 95% identical to amino acid residues 52 to 135 of SEQ ID NO:4.

23. The protein of claim 21 which comprises a heterologous polypeptide sequence.

24. A composition comprising the protein of claim 21 and a pharmaceutically acceptable carrier.

25. An isolated protein produced by the method comprising:
   (a) expressing the protein of claim 21 by a cell; and
   (b) recovering said protein.

26. An isolated protein comprising a polypeptide sequence which is at least 90% identical to the secreted portion of the polypeptide encoded by the cDNA contained in ATCC Deposit No. 203563, wherein said isolated protein possesses peptidoglycan binding activity.

27. The isolated protein of claim 26 wherein said polypeptide sequence is at least 90% identical to the complete polypeptide encoded by the cDNA contained in ATCC Deposit No. 203563.

28. The isolated protein of claim 26 wherein said polypeptide sequence is at least 95% identical to the secreted portion of the polypeptide encoded by the cDNA contained in ATCC Deposit No. 203563.

29. The isolated protein of claim 26 wherein said polypeptide sequence is at least 95% identical to the complete polypeptide encoded by the cDNA contained in ATCC Deposit No. 203563.

30. The protein of claim 26 which comprises a heterologous polypeptide sequence.

31. A composition comprising the protein of claim 26 and a pharmaceutically acceptable carrier.

32. An isolated protein produced by the method comprising:
   (a) expressing the protein of claim 26 by a cell; and
   (b) recovering said protein.

33. An isolated protein comprising at least 30 contiguous amino acid residues of amino acid residues 52 to 135 of SEQ ID NO:4, wherein said isolated protein possesses peptidoglycan binding activity.

34. The isolated protein of claim 33 which comprises at least 50 contiguous amino acid residues of amino acid residues 52 to 135 of SEQ ID NO:4.

35. The protein of claim 33 which comprises a heterologous polypeptide sequence.

36. A composition comprising the protein of claim 33 and a pharmaceutically acceptable carrier.

37. An isolated protein produced by the method comprising:
(a) expressing the protein claim 33 by a cell; and
(b) recovering said protein.

38. An isolated protein comprising at least 30 contiguous amino acid residues of amino acid residues 18 to 368 of SEQ ID NO:4, wherein said isolated protein possesses peptidoglycan binding activity.

39. The isolated protein of claim 38 which comprises at least 50 contiguous amino acid residues of amino acid residues 18 to 368 of SEQ ID NO:4.

40. The protein of claim 38 which comprises a heterologous polypeptide sequence.

41. A composition comprising the protein of claim 38 and a pharmaceutically acceptable carrier.

42. An isolated protein produced by the method comprising:
(a) expressing the protein of claim 38 by a cell; and
(b) recovering said protein.

43. An isolated protein comprising at least 30 contiguous amino acid residues of the secreted portion of the polypeptide encoded by the cDNA contained in ATCC Deposit No. 203563, wherein said isolated protein possesses peptidoglycan binding activity.

44. The isolated protein of claim 43 which comprises at least 50 contiguous amino acid residues of the secreted portion of the polypeptide encoded by the cDNA contained in ATCC Deposit No. 203563.

45. The protein of claim 43 which comprises a heterologous polypeptide sequence.

46. A composition comprising the protein of claim 43 and pharmaceutically acceptable carrier.

47. An isolated protein produced by the method comprising:
(a) expressing the protein of claim 43 by a cell; and
(b) recovering said protein.

48. An isolated protein comprising at least 30 contiguous amino acid residues of amino acid residues 1 to 368 of SEQ ID NO:4, wherein said isolated protein possesses peptidoglycan binding activity.

49. The isolated protein of claim 48 which comprises at least 50 contiguous amino acid residues of amino acid residues 1 to 368 of SEQ ID NO:4.

50. The protein of claim 48 which comprises a heterologous polypeptide sequence.

51. A composition comprising the protein of claim 48 and a pharmaceutically acceptable carrier.

52. An isolated protein produced by the method comprising:
(a) expressing the protein of claim 48 by a cell; and
(b) recovering said protein.

53. An isolated protein comprising at least 30 contiguous amino acid residues of the complete polypeptide encoded by the cDNA contained in ATCC Deposit No. 203563, wherein said isolated protein possesses peptidoglycan binding activity.

54. The isolated protein of claim 53 which comprises at least 50 contiguous amino acid residues of the complete polypeptide encoded by the cDNA contained in ATCC Deposit No. 203563.

55. The protein of claim 53 which comprises a heterologous polypeptide sequence.

56. A composition comprising the protein of claim 53 and pharmaceutically acceptable carrier.

57. An isolated protein produced by the method comprising:
(a) expressing the protein of claim 53 by a cell; and
(b) recovering said protein.

58. An isolated protein comprising at least 30 contiguous amino acid residues of amino acid residues 18 to 368 of SEQ ID NO:4, wherein said isolated protein possesses peptidoglycan binding activity.

59. The isolated protein of claim 58 which comprises at least 50 contiguous amino acid residues of amino acid residues 18 to 368 of SEQ ID NO:4.

60. The protein of claim 58 which comprises a heterologous polypeptide sequence.

61. A composition comprising the protein of claim 58 and a pharmaceutically acceptable carrier.

62. An isolated protein produced by the method comprising:
(a) expressing the protein of claim 58 by a cell; and (b) recovering said protein.

63. An isolated protein comprising a polypeptide sequence selected from the group consisting of:
(a) amino acid residues 17 to 32 of SEQ ID NO:4;
(b) amino acid residues 40 to 58 of SEQ ID NO:4;
(c) amino acid residues 82 to 99 of SEQ ID NO:4;
(d) amino acid residues 104 to 111 of SEQ ID NO:4;
(e) amino acid residues 150 to 159 of SEQ ID NO:4;
(f) amino acid residues 174 to 182 of SEQ ID NO:4;
(g) amino acid residues 186 to 207 of SEQ ID NO:4;
(h) amino acid residues 214 to 225 of SEQ ID NO:4;
(i) amino acid residues 237 to 252 of SEQ ID NO:4;
(j) amino acid residues 259 to 268 of SEQ ID NO:4;
(k) amino acid residues 290 to 300 of SEQ ID NO:4; and
(l) amino acid residues 344 to 355 of SEQ ID NO:4.

64. The isolated protein of claim 63 which comprises polypeptide sequence (a).

65. The isolated protein of claim 63 which comprises polypeptide sequence (b).

66. The isolated protein of claim 63 which comprises polypeptide sequence (c).

67. The isolated protein of claim 63 which comprises polypeptide sequence (d).

68. The isolated protein of claim 67 which further comprises polypeptide sequence (c).

69. The isolated protein of claim 63 which comprises polypeptide sequence (e).

70. The isolated protein of claim 63 which comprises polypeptide sequence (f).

71. The isolated protein of claim 63 which comprises polypeptide sequence (g).

72. The isolated protein of claim 63 which comprises polypeptide sequence (h).

73. The isolated protein of claim 63 which comprises polypeptide sequence (i).

74. The isolated protein of claim 63 which comprises polypeptide sequence (j).

75. The isolated protein of claim 63 which comprises polypeptide sequence (k).

76. The isolated protein of claim 63 which comprises polypeptide sequence (l).

77. The protein of claim 63 which comprises a heterologous polypeptide sequence.

78. A composition comprising the protein of claim 63 and a pharmaceutically acceptable carrier.

79. An isolated protein produced by the method comprising:
(a) expressing the protein of claim 63 by a cell; and
(b) recovering said protein.

* * * * *

SEQUENCE LISTING

```
<160> NUMBER OF SEQ ID NOS: 14

<210> SEQ ID NO 1
<211> LENGTH: 1182
<212> TYPE: DNA
<213> ORGANISM: Homo sapiens

<400> SEQUENCE: 1
ctgggctgga acagcacaga acccacaggg ctgccgtcca cactctcccg gtcagagtcc        60
tgggaccaca tggggacgct gccatggctt cttgccttct tcattctggg tctccaggct       120
tgggatactc ccaccatcgt ctcccgcaag gagtgggggg caagaccgct cgcctgcagg       180
gccctgctga ccctgcctgt ggcctacatc atcacagacc agctcccagg gatgcagtgc       240
cagcagcaga gcgtttgcag ccagatgctg cggggggttgc agtcccattc cgtctacacc       300
ataggctggt gcgacgtggc gtacaacttc ctggttgggg atgatggcag ggtgtatgaa       360
ggtgttggct ggaacatcca aggcttgcac acccagggct acaacaacat ttccctgggc       420
atcgccttct ttggcaataa gataagcagc agtcccagcc ctgctgcctt atcagctgca       480
gagggtctga tctcctatgc catccagaag ggtcacctgt cgcccaggta tattcagcca       540
cttcttctga aagaagagac ctgcctggac cctcaacatc cagtgatgcc caggaaggtt       600
tgccccaaca tcatcaaacg atctgcttgg gaagccagag agacacactg ccctaaaatg       660
aacctcccag ccaaatatgt catcatcatc cacaccgctg gcacaagctg cactgtatcc       720
acagactgcc agactgtcgt ccgaaacata cagtccttc acatggacac acggaactt        780 tgtgacattg gatatcaata aggccaggcg tggcggcgat tacgtctgta atcccaggac       840
tttgggaggc caaggcgggc agatcacttc aggccaggaa ttcaagagca gcctggccaa       900
tatggcgaaa ctctgtctct actgaaaaca aacaaacaaa caaacaaaca aacaaagaaa      960
caacaaaaat tagccgggtg tggtggcaca cgcctgtagt cccagctact caggaggctg      1020
aggcataaga attgcttgaa ccctggaggc ggaggttgca gtgagctgag attgggccac     1080
cgcactccag tctgggagac agagtgagac tgtctcaaaa caacaacaaa aaaatcccta    1140
acataatctc aaaaaaaaaa aaaaaaaaaa aaaaaaaaaa aa                        1182

<210> SEQ ID NO 2
<211> LENGTH: 243
```

-continued

```
<212> TYPE: PRT
<213> ORGANISM: Homo sapiens

<400> SEQUENCE: 2

Met Gly Thr Leu Pro Trp Leu Leu Ala Phe Phe Ile Leu Gly Leu Gln
  1               5                  10                  15

Ala Trp Asp Thr Pro Thr Ile Val Ser Arg Lys Glu Trp Gly Ala Arg
             20                  25                  30

Pro Leu Ala Cys Arg Ala Leu Leu Thr Leu Pro Val Ala Tyr Ile Ile
         35                  40                  45

Thr Asp Gln Leu Pro Gly Met Gln Cys Gln Gln Ser Val Cys Ser
     50                  55                  60

Gln Met Leu Arg Gly Leu Gln Ser His Ser Val Tyr Thr Ile Gly Trp
 65                 70                  75                  80

Cys Asp Val Ala Tyr Asn Phe Leu Val Gly Asp Gly Arg Val Tyr
                 85                  90                  95

Glu Gly Val Gly Trp Asn Ile Gln Gly Leu His Thr Gln Gly Tyr Asn
            100                 105                 110

Asn Ile Ser Leu Gly Ile Ala Phe Phe Gly Asn Lys Ile Ser Ser Ser
            115                 120                 125

Pro Ser Pro Ala Ala Leu Ser Ala Ala Glu Gly Leu Ile Ser Tyr Ala
130                 135                 140

Ile Gln Lys Gly His Leu Ser Pro Arg Tyr Ile Gln Pro Leu Leu Leu
145                 150                 155                 160

Lys Glu Glu Thr Cys Leu Asp Pro Gln His Pro Val Met Pro Arg Lys
                165                 170                 175

Val Cys Pro Asn Ile Ile Lys Arg Ser Ala Trp Glu Ala Arg Glu Thr
            180                 185                 190

His Cys Pro Lys Met Asn Leu Pro Ala Lys Tyr Val Ile Ile Ile His
        195                 200                 205

Thr Ala Gly Thr Ser Cys Thr Val Ser Thr Asp Cys Gln Thr Val Val
    210                 215                 220

Arg Asn Ile Gln Ser Phe His Met Asp Thr Arg Asn Phe Cys Asp Ile
225                 230                 235                 240

Gly Tyr Gln

<210> SEQ ID NO 3
<211> LENGTH: 1876
<212> TYPE: DNA
<213> ORGANISM: Homo sapiens

<400> SEQUENCE: 3
gggcaagctg actgcaccct gacctgctgg gctgggacag cacaggaccc acagatatct      60
gctgccatcc acactctcca gattggtgtc ctgggaccac gtggggatgc tgctgtggct     120
tcttgtcttc tctgctctgg gtatccaggc ctgggtgat tcctcctgga acaaaacaca     180
agctaaacag gtatcagagg ggctccagta cctatttgag aacatctccc agctcactga     240
aaaagatgtc tccaccacgg tctctcgcaa ggcatggggg gcagaagctg ttggctgcag     300
tattcagctg accacgccag tgaatgtcct tgttatacac catgtccctg gactggagtg     360
tcacgaccag acagtctgca gccagagact gcgggaactg caggcccatc atgtccacaa     420
caacagtggg tgtgatgtgg cctacaactt cctggttggg gatgatggca gggtgtatga     480
aggtgttggc tggaatatcc aaggagtgca cacccaaggc tacaacaaca tctccctggg     540
ctttgccttc ttcggcacta agaaaggcca cagtcccagc cctgctgccc tgtcggccat     600
```

```
ggaaaaccta atcacctatg ctgtccagaa gggccacctg tcatccagtt atgttcagcc    660
acttcttggg aaaggcgaga actgcctggc ccctcggcag aagacaagcc tgaagaagct    720
tgccccggca ttgtcccacg gtctgtgtgg ggagccaggg agaccactgt ccaggatgac    780
tctcccagcg aagtatggca tcattatcca cactgccggg aggacctgca acatttctga    840
tgagtgccgc ctgctggtcc gggacatcca gtctttctac atagacaggc tcaagtcatg    900
cgacattggt tataacttcc tggtgggcca ggatggcgcc atttatgaag ggtgggctg     960 gaatgtccaa ggctcctcca ccctggcta cgatgacatt gccctgggca ttaccttcat   1020
gggcaccttc acaggtatac cacccaatgc tgcagcacta gaggcagccc aagacctgat   1080
ccagtgtgcc atggtcaaag gtacctgac tcccaactac ctgctggtgg ccacagtga    1140 tgtggcccga accttgtctc ctgggcaggc tttgtacaac atcatcagca cctggcctca   1200
tttcaaacac tgagagaagc cccaggtcct tctgagactg cttccctcc cctgtcaggt    1260 ctctcctgtc ctaaccatcc agcttggctc aacacctttt gccctcctcc cctgccacac   1320
agtcctgtgc ctccttttc aggttgggat gatcatgcct ctcctgccaa catcctccaa    1380
gggcctccaa actcatagct ggacattcac agccctctga gtctgagtcc agatttcttc   1440
tctccttact tcctctccct tggaaaccca actcctcagc caggtgagac aatgggctgg   1500
ttcttgtttc atttctctct ctctctccat tcccctctgc ctggtgagcc ttcccctggt   1560
gtctgcctgg cagcccccac cacccaccta tcacccctca cccataactc aggtcaacgt   1620
gaccaacctt ccttgcttac ataaaactt gtatatattt ggatgtagcc cttatttaat    1680
ggctgtcatt atttatagat atgtctatcc ttgctacttg gttgtgagtt tctccagggg   1740
aggaactgtg ttttattcat ctctatgtcc tctgtttctc agcagtgtct gaaatttaat   1800
gggttctact gatgtttatt agagaaatgg atgaataaat gaatgaagag atccaaaaaa   1860
aaaaaaaaaa aaaaaa                                                   1876
```

<210> SEQ ID NO 4
<211> LENGTH: 368
<212> TYPE: PRT
<213> ORGANISM: Homo sapiens

<400> SEQUENCE: 4

```
Met Leu Leu Trp Leu Leu Val Phe Ser Ala Leu Gly Ile Gln Ala Trp
 1               5                  10                  15

Gly Asp Ser Ser Trp Asn Lys Thr Gln Ala Lys Gln Val Ser Glu Gly
                20                  25                  30

Leu Gln Tyr Leu Phe Glu Asn Ile Ser Gln Leu Thr Glu Lys Asp Val
            35                  40                  45

Ser Thr Thr Val Ser Arg Lys Ala Trp Gly Ala Glu Ala Val Gly Cys
        50                  55                  60

Ser Ile Gln Leu Thr Thr Pro Val Asn Val Leu Val Ile His His Val
    65                  70                  75                  80

Pro Gly Leu Glu Cys His Asp Gln Thr Val Cys Ser Gln Arg Leu Arg
                85                  90                  95

Glu Leu Gln Ala His His Val His Asn Asn Ser Gly Cys Asp Val Ala
            100                 105                 110

Tyr Asn Phe Leu Val Gly Asp Asp Gly Arg Val Tyr Glu Gly Val Gly
        115                 120                 125

Trp Asn Ile Gln Gly Val His Thr Gln Gly Tyr Asn Asn Ile Ser Leu
    130                 135                 140
```

-continued

```
Gly Phe Ala Phe Phe Gly Thr Lys Lys Gly His Ser Pro Ser Pro Ala
145                 150                 155                 160

Ala Leu Ser Ala Met Glu Asn Leu Ile Thr Tyr Ala Val Gln Lys Gly
                165                 170                 175

His Leu Ser Ser Ser Tyr Val Gln Pro Leu Leu Gly Lys Gly Glu Asn
            180                 185                 190

Cys Leu Ala Pro Arg Gln Lys Thr Ser Leu Lys Lys Leu Ala Pro Ala
        195                 200                 205

Leu Ser His Gly Leu Cys Gly Glu Pro Gly Arg Pro Leu Ser Arg Met
    210                 215                 220

Thr Leu Pro Ala Lys Tyr Gly Ile Ile Ile His Thr Ala Gly Arg Thr
225                 230                 235                 240

Cys Asn Ile Ser Asp Glu Cys Arg Leu Leu Val Arg Asp Ile Gln Ser
                245                 250                 255

Phe Tyr Ile Asp Arg Leu Lys Ser Cys Asp Ile Gly Tyr Asn Phe Leu
            260                 265                 270

Val Gly Gln Asp Gly Ala Ile Tyr Glu Gly Val Gly Trp Asn Val Gln
        275                 280                 285

Gly Ser Ser Thr Pro Gly Tyr Asp Asp Ile Ala Leu Gly Ile Thr Phe
    290                 295                 300

Met Gly Thr Phe Thr Gly Ile Pro Pro Asn Ala Ala Ala Leu Glu Ala
305                 310                 315                 320

Ala Gln Asp Leu Ile Gln Cys Ala Met Val Lys Gly Tyr Leu Thr Pro
                325                 330                 335

Asn Tyr Leu Leu Val Gly His Ser Asp Val Ala Arg Thr Leu Ser Pro
            340                 345                 350

Gly Gln Ala Leu Tyr Asn Ile Ile Ser Thr Trp Pro His Phe Lys His
        355                 360                 365
```

<210> SEQ ID NO 5
<211> LENGTH: 749
<212> TYPE: DNA
<213> ORGANISM: Homo sapiens

<400> SEQUENCE: 5

```
gatcccccgg gctgcaggaa ttcggcacga gccggaccct gccgccctgc cactatgtcc      60
cgccgctcta tgctgcttgc ctgggctctc cccagcctcc ttcgactcgg agcggctcag     120
gagacagaag acccggcctg ctgcagcccc atagtgcccc ggaacgagtg gaaggccctg     180
gcatcagagt gcgcccagca cctgagcctg cccttacgct atgtggtggt atcgcacacg     240
gcgggcagca gctgcaacac ccccgcctcg tgccagcagc aggcccggaa tgtgcagcac     300
taccacatga agacactggg ctggtgcgac gtgggctaca acttcctgat tggagaagac     360
gggctcgtat acgagggccg tggctggaac ttcacgggtg cccactcagg tcacttatgg     420
aaccccatgt ccattggcat cagcttcatg ggcaactaca tggatcgggt gcccacaccc     480
caggccatcc gggcagccca gggtctactg gcctgcggtg tggctcaggg agccctgagg     540
tccaactatg tgctcaaagg acaccgggat gtgcagcgta cactctctcc aggcaaccag     600
ctctaccacc tcatccagaa ttggccacac taccgctccc cctgaggccc tgctgatccg     660
caccccattc ctcccctccc atggccaaaa accccactgt ctccttctcc aataaagatg     720
tagctcaaaa aaaaaaaaaa aaaaaaaaa                                       749
```

<210> SEQ ID NO 6

```
<211> LENGTH: 196
<212> TYPE: PRT
<213> ORGANISM: Homo sapiens

<400> SEQUENCE: 6

Met Ser Arg Arg Ser Met Leu Leu Ala Trp Ala Leu Pro Ser Leu Leu
 1               5                  10                  15

Arg Leu Gly Ala Ala Gln Glu Thr Glu Asp Pro Ala Cys Cys Ser Pro
             20                  25                  30

Ile Val Pro Arg Asn Glu Trp Lys Ala Leu Ala Ser Glu Cys Ala Gln
         35                  40                  45

His Leu Ser Leu Pro Leu Arg Tyr Val Val Ser His Thr Ala Gly
     50                  55                  60

Ser Ser Cys Asn Thr Pro Ala Ser Cys Gln Gln Ala Arg Asn Val
 65                  70                  75                  80

Gln His Tyr His Met Lys Thr Leu Gly Trp Cys Asp Val Gly Tyr Asn
                 85                  90                  95

Phe Leu Ile Gly Glu Asp Gly Leu Val Tyr Glu Gly Arg Gly Trp Asn
                100                 105                 110

Phe Thr Gly Ala His Ser Gly His Leu Trp Asn Pro Met Ser Ile Gly
            115                 120                 125

Ile Ser Phe Met Gly Asn Tyr Met Asp Arg Val Pro Thr Pro Gln Ala
        130                 135                 140

Ile Arg Ala Ala Gln Gly Leu Leu Ala Cys Gly Val Ala Gln Gly Ala
145                 150                 155                 160

Leu Arg Ser Asn Tyr Val Leu Lys Gly His Arg Asp Val Gln Arg Thr
                165                 170                 175

Leu Ser Pro Gly Asn Gln Leu Tyr His Leu Ile Gln Asn Trp Pro His
            180                 185                 190

Tyr Arg Ser Pro
        195

<210> SEQ ID NO 7
<211> LENGTH: 151
<212> TYPE: PRT
<213> ORGANISM: Homo sapiens

<400> SEQUENCE: 7

Met Leu Phe Ala Cys Ala Leu Leu Ala Leu Leu Gly Leu Ala Thr Ser
 1               5                  10                  15

Cys Ser Phe Ile Val Pro Arg Ser Glu Trp Arg Ala Leu Pro Ser Glu
             20                  25                  30

Cys Ser Ser Arg Leu Gly His Pro Val Arg Tyr Val Val Ile Ser His
         35                  40                  45

Thr Ala Gly Ser Phe Cys Asn Ser Pro Asp Ser Cys Glu Gln Gln Ala
     50                  55                  60

Arg Asn Val Gln His Tyr His Lys Asn Glu Leu Gly Trp Cys Asp Val
 65                  70                  75                  80

Ala Tyr Asn Phe Leu Ile Gly Glu Asp Gly His Val Tyr Glu Gly Arg
                 85                  90                  95

Gly Trp Asn Ile Lys Gly Asp His Thr Gly Pro Ile Trp Asn Pro Met
                100                 105                 110

Ser Ile Gly Ile Thr Phe Met Gly Asn Phe Met Asp Arg Val Arg Lys
            115                 120                 125

Ala Gly Pro Pro Cys Cys Pro Lys Ser Ser Gly Ile Trp Gly Val Ser
        130                 135                 140
```

Gly Leu Pro Glu Ile Gln Leu
145              150

<210> SEQ ID NO 8
<211> LENGTH: 43
<212> TYPE: DNA
<213> ORGANISM: Homo sapiens

<400> SEQUENCE: 8
gcagcacata tggattcctc ctggaacaaa acacaagcta aac          43

<210> SEQ ID NO 9
<211> LENGTH: 46
<212> TYPE: DNA
<213> ORGANISM: Homo sapiens

<400> SEQUENCE: 9
gcagcaggta ccttagtgtt tgaaatgagg ccaggtgctg atgatg        46

<210> SEQ ID NO 10
<211> LENGTH: 48
<212> TYPE: DNA
<213> ORGANISM: Homo sapiens

<400> SEQUENCE: 10
gcagcaggat ccgccatcat ggggacgctg ccatggcttc ttgccttc      48

<210> SEQ ID NO 11
<211> LENGTH: 46
<212> TYPE: DNA
<213> ORGANISM: Homo sapiens

<400> SEQUENCE: 11
gcagcaggta ccttattgat atccaatgtc acaaaagttc cgtgtg        46

<210> SEQ ID NO 12
<211> LENGTH: 48
<212> TYPE: DNA
<213> ORGANISM: Homo sapiens

<400> SEQUENCE: 12
gcagcaggat ccgccatcat ggggacgctg ccatggcttc ttgccttc      48

<210> SEQ ID NO 13
<211> LENGTH: 46
<212> TYPE: DNA
<213> ORGANISM: Homo sapiens

<400> SEQUENCE: 13
gcagcaggta ccttattgat atccaatgtc acaaaagttc cgtgtg        46

<210> SEQ ID NO 14
<211> LENGTH: 733
<212> TYPE: DNA
<213> ORGANISM: Homo sapiens

<400> SEQUENCE: 14
gggatccgga gcccaaatct tctgacaaaa ctcacacatg cccaccgtgc ccagcacctg     60
aattcgaggg tgcaccgtca gtcttcctct tccccccaaa acccaaggac accctcatga   120
tctcccggac tcctgaggtc acatgcgtgg tggtggacgt aagccacgaa gaccctgagg   180
tcaagttcaa ctggtacgtg gacggcgtgg aggtgcataa tgccaagaca aagccgcggg   240

```
aggagcagta caacagcacg taccgtgtgg tcagcgtcct caccgtcctg caccaggact    300
ggctgaatgg caaggagtac aagtgcaagg tctccaacaa agccctccca accccatcg    360 agaaaaccat ctccaaagcc aaagggcagc cccgagaacc acaggtgtac accctgcccc    420
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                      733
```